US012528774B2

(12) United States Patent
Radu et al.

(10) Patent No.: US 12,528,774 B2
(45) Date of Patent: Jan. 20, 2026

(54) THIOSEMICARBAZONE COMPOUNDS AND USES THEREOF

(71) Applicant: The Regents of the University of California, Oakland, CA (US)

(72) Inventors: Caius G. Radu, Los Angeles, CA (US); Michael E. Jung, Los Angeles, CA (US); Daniel Sun, Los Angeles, CA (US); Nagichettiar Satyamurthy, Los Angeles, CA (US); Juno Van Valkenburgh, Los Angeles, CA (US); Roy Pan, Los Angeles, CA (US); Soumya Poddar, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1062 days.

(21) Appl. No.: 17/429,722

(22) PCT Filed: Feb. 21, 2020

(86) PCT No.: PCT/US2020/019249
§ 371 (c)(1),
(2) Date: Aug. 10, 2021

(87) PCT Pub. No.: WO2020/176349
PCT Pub. Date: Sep. 3, 2020

(65) Prior Publication Data

US 2022/0274929 A1 Sep. 1, 2022

Related U.S. Application Data

(60) Provisional application No. 62/810,160, filed on Feb. 25, 2019.

(51) Int. Cl.
*C07D 217/14* (2006.01)
*C07F 1/08* (2006.01)

(52) U.S. Cl.
CPC .............. *C07D 217/14* (2013.01); *C07F 1/08* (2013.01)

(58) Field of Classification Search
CPC ................................ C07D 217/14; C07F 1/08
See application file for complete search history.

(56) References Cited

U.S. PATENT DOCUMENTS

| | | | |
|---|---|---|---|
| 4,269,834 | A | 5/1981 | Nauta |
| 6,248,782 | B1 | 6/2001 | Elford et al. |
| 2007/0135464 | A1 | 6/2007 | Browner et al. |
| 2013/0089626 | A1 | 4/2013 | Pollard et al. |
| 2017/0100352 | A1 | 4/2017 | Elford |

FOREIGN PATENT DOCUMENTS

WO WO-2016/161615 A1 10/2016

OTHER PUBLICATIONS

Liu, Mao-Chin, et al. Journal of medicinal chemistry 38.21 (1995): 4234-4243. (Year: 1995).*
French, F. A., et al. Journal of Medicinal Chemistry 17.2 (1974): 172-181. (Year: 1974).*
International Search Report mailed on Jun. 9, 2020 for PCT Application No. PCT/US2020/019249, filed Feb. 21, 2020, 4 pages.
PubChem 9554793, Create Date: Oct. 23, 2006, 12 pages.
Sun, D. et al. (Mar. 25, 2019). "Evaluation of Potent Isoquinoline-Based Thiosemicarbazone Antiproliferatives Against Solid Tumor Models," *ChemRxiv* 1-37.
Written Opinion mailed on Jun. 9, 2020 for PCT Application No. PCT/US2020/019249, filed Feb. 21, 2020, 7 pages.

* cited by examiner

*Primary Examiner* — Joseph K Mckane
*Assistant Examiner* — Quincy Mckoy
(74) *Attorney, Agent, or Firm* — Mintz, Levin, Cohn, Ferris, Glovsky and Popeo, P.C.

(57) ABSTRACT

Provided, inter alia, are thiosemicarbazone compounds, metal complexes of thiosemicarbazone compounds, pharmaceutical compositions, and methods for treating cancer.

13 Claims, 24 Drawing Sheets

HCT-1

HCT-2

HCT-3

HCT-4

HCT-5

HCT-6

HCT-7

HCT-8

HCT-9

HCT-10

HCT-11

HCT-12

HCT-13

HCT-14

HCT-15

THIOSEMICARBAZONE COMPOUNDS AND USES THEREOF

CROSS-REFERENCE TO RELATED APPLICATIONS

This application is a Section 371 US national phase of International Application No. PCT/US2020/019249 filed Feb. 21, 2020, which claims priority to U.S. Application No. 62/810,160 filed Feb. 25, 2019, the disclosure of which is incorporated by reference herein in its entirety.

STATEMENT REGARDING FEDERALLY SPONSORED RESEARCH OR DEVELOPMENT

This invention was made with government support under grant number CA187678 awarded by the National Institutes of Health. The government has certain rights in the invention.

BACKGROUND

The therapeutic potential of α-N-heterocyclic carboxaldehyde thiosemicarbazones (HCTs) have been investigated since the 1940s, with tuberculostatic activity being first observed in vivo as early as 1946. (Ref 1). This class of compounds was subsequently shown to possess antitumor, antiviral, antibacterial, and antifungal activities, prompting decades of research and development. (Refs 2-7). In particular, isoquinoline-based HCTs such as IQ-1 (HCT-1) (Ref 3) were the subject of early interest due to their efficacy, particularly in terms of 50-day survival rates of tumor-bearing mice. (Ref 5). The research groups of Sartorelli and French spent decades developing isoquinoline HCTs and investigating other HCT scaffolds, eventually turning their attention to pyridyl-based HCT analogs. Notably, in 1992 Sartorelli and coworkers developed 3-aminopyridine-2-carboxaldehyde thiosemicarbazone (3-AP, also known as Triapine), a pyridyl-based HCT. It has since undergone multiple clinical trials for the treatment of various cancers, and it is widely accepted to inhibit ribonucleotide reductase (RNR), a critical enzyme for rapidly proliferating cells such as bacteria and cancer cells. (Refs 8-14). Two other HCT compounds, namely di-2-pyridylketone 4-cyclohexyl-4-methyl-3-thiosemicarbazone (DpC) hydrochloride and 4-(2-pyridinyl)-2-(6,7-dihydro-8(5H)-quinolinylidene)hydrazide-1-piperazinecarbothioic acid (COTI-2) (Refs. 15-16), have been investigated in the clinic. However, despite the early promise, no HCT compounds have yet advanced beyond phase II clinical trials. (Ref 13).

While the mechanisms of action of HCTs are multi-modal and have not yet been fully defined (Refs. 17-25), their biological activities generally stem from the ability to chelate transition metals through their heterocyclic nitrogen, Schiff base nitrogen, and thiosemicarbazone sulfur. The resulting HCT-metal complexes can undergo redox cycles, a property which is reported to generate cytotoxic reactive oxygen species (ROS) through Fenton and/or Haber-Weiss processes. (Ref 26). HCTs are particularly adept at binding copper (Ref 27), which can be either detrimental or beneficial to the compound's biological activity. For instance, physiological concentrations of copper in human plasma (11-18 μM) (Refs 28-29) strongly interfere with the RNR-inhibitory activity of 3-AP (Ref 27), while the cytotoxicities of Dp44mT (Refs 30-31) and NSC-319726 (Ref 32) against glioblastoma and other cancer models are potentiated by copper. Binding of this transition metal is intriguing from an anticancer therapy standpoint, as cancers rely upon higher intracellular levels of copper, relative to healthy cells, to promote angiogenesis, tumor growth, and metastasis. (Refs 33-34). Indeed, several therapeutic strategies have employed small molecules to disrupt copper homeostasis in cancers, either through chelation-mediated copper sequestration, or by increasing intracellular copper to cytotoxic levels through ionophoric modalities. (Refs 32, 35).

The antiproliferative effects of HCTs coupled with their ability to bind copper make them a compelling scaffold from which to develop copper-mediated therapeutics. Additionally, studies investigating the isoquinoline HCT chemical space have not emerged for years, as focus shifted away from this scaffold following the report of 3-AP. (Refs. 3, 5, 6).

There is a need in the art for isoquinoline-based HCTs which overcome the problems associated with previously described compounds. This disclosure is directed to this, as well as other, important ends.

BRIEF SUMMARY

The disclosure provides compounds of Formula (I), pharmaceutically acceptable salts thereof, metal complexes thereof, and pharmaceutically acceptable salts of metal complexes thereof, wherein the compound of Formula (I) is:

(I)

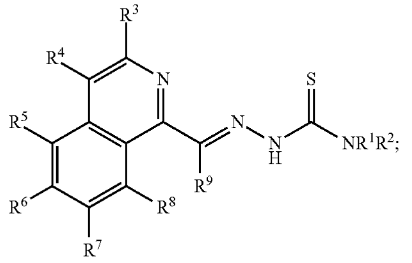

where the substituents are as defined herein. The disclosure provides pharmaceutical compositions compounds of Formula (I), pharmaceutically acceptable salts thereof, metal complexes thereof, or pharmaceutically acceptable salts of metal complexes thereof, and a pharmaceutically acceptable excipient. In aspects, the compound of Formula (I) is a compound of Formula (Ia). The disclosure provides methods of treating cancer in patients by administering to the patients compounds of Formula (I), pharmaceutically acceptable salts thereof, metal complexes thereof, or pharmaceutically acceptable salts of metal complexes thereof. The disclosure provides methods of treating cancer in patients by administering to the patients pharmaceutical compositions comprising compounds of Formula (I), pharmaceutically acceptable salts thereof, metal complexes thereof, or pharmaceutically acceptable salts of metal complexes thereof, and a pharmaceutically acceptable excipient.

The disclosure provides compounds of Formula (II) and pharmaceutically acceptable salts thereof, wherein the compound of Formula (II) is:

(II)

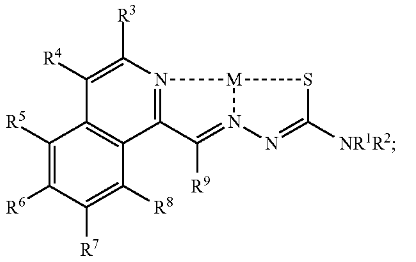

where the substituents are as defined herein. The disclosure provides pharmaceutical compositions compounds of Formula (II) or pharmaceutically acceptable salts thereof, and a pharmaceutically acceptable excipient. In aspects, the compound of Formula (II) is a compound of Formula (IIa). The disclosure provides methods of treating cancer in patients by administering to the patients compounds of Formula (II) or pharmaceutically acceptable salts thereof. The disclosure provides methods of treating cancer in patients by administering to the patients pharmaceutical compositions comprising compounds of Formula (II) or pharmaceutically acceptable salts thereof, and a pharmaceutically acceptable excipient.

These and other embodiments and aspects of the disclosure are described herein.

BRIEF DESCRIPTION OF THE DRAWINGS

FIG. 1A: $IC_{50}$ values in a panel of human and mouse prostate cancer (PC)(cell lines CF-2, LNCaP, 22Rv1, RM-1, MyC CaP); small cell lung carcinoma (SCLC)(cell lines NCI-H1963, NCI-H146, NCI-H526); pancreatic ductal adenocarcinoma (PDAC)(CFPAC1, SW1990, HS766T, PANC0203, PANC0813, ASPC1, HPAFII, PATU8902, PANC0327, PANC1, YAPC, L36PL, XWR200, HUPT4, A13A, SUIT2, DAN-G, BxPC3, HPAC, PSN1, SU8686, KP4662, MIAPACA2, PATU8988T); and leukemia (cell lines KG-1, TF-1, Jurkat, MOLT-4, p185-R, MV4-11) models treated with HCT13+Cu(II) (20 μM) for 72 h measured by CellTiterGlo. FIG. 1G-1U: shows the CellTiterGlo assays of cell viability-proliferation in MIAPACA2 cells treated with each HCT (HCT Numbers 1-15) compound±Cu (II) (20 μM) for 72h (where the open (light-color) circle is the compound alone and the closed (dark-color) circle is the compound+Cu(II)).

FIG. 2A: representative immunoblots of MIAPACA2 PDAC cells treated as indicated for 24h. FIGS. 2B-2C: reactive oxygen species (ROS) measurement using CM-$H_2$DCFDA staining after HCT13 (25 nM)+Cu(II) (20 μM) treatment for 24h; mean fluorescence intensity (MFI); mean±SD, n=2, Student t-test, *P<0.001. FIG. 2D-2E: mitochondrial ROS detection using MitoSOX staining in MIAPACA2 PDAC cells treated with HCT-13 (25 nM)+Cu (II) (20 μM) for 24h; mean±SD, n=2, Student t-test, *P<0.001. FIG. 2F: oxygen consumption rate (OCR) of MIAPACA2 PDAC cells treated with HCT-13 (25 nM)+Cu (II) (20 μM). FIG. 2G: OCR of isolated mitochondria measured with or without HCT-13 (25 nM)+Cu(II) (20 μM). FIG. 2H: viability of 143 BTK parental (wild type, WT) and po cells after 48 h of treatment with the indicated HCT-13 concentrations+Cu(II) (20 μM) treatment, assessed with trypan blue staining; mean±SD, n=2, Student t-test, *P<0.001. FIG. 2I: cell viability by trypan blue staining in MIAPACA2 PDAC cells to interrogate the interaction of HCT-13 (25 nM)+Cu(II) (20 μM) with 2-DG (2 mM) for 48 h; mean±SD, n=2, Student t-test, *P<0.001.

FIG. 3A: Mito Stress Test of MIAPACA2 PDAC cells treated with HCT13 (25 nM)+Cu (II) (20 μM) for 24h. FIG. 3B: electron flow assay in isolated mitochondria treated with HCT-13 (100 nM)+Cu(II) (20 μM) for 1h. FIG. 3C: viability of 143 BTK parental (wild type, WT) and $\rho_0$ cells after 48h of the indicated HCT13 concentration+Cu(II) (20 μM) treatment, assessed with Trypan Blue Staining. FIG. 3D: 48h cell cycle histogram and plots of S-phase arrest plots in 143 BTK WT and 143 BTK $\rho_0$ cells at 24, 48 and 72h following treatment with indicated concentrations of HCT13+Cu(II)(20 μM). (mean±SD, n=2, one-way ANOVA corrected for multiple comparisons by Bonferroni adjustment, * P<0.05;  P<0.01; * P<0.001).

FIG. 4A: experimental design of a synthetic lethality screen using a library of protein kinase inhibitors against HCT13-treated cells in the presence of Cu(II) (20 μM). FIG. 4B: radar plot of screen results. FIG. 4C: z-score values for kinase inhibitors within the DNA damage response/replication stress response (DDR/RSR) pathway module. FIG. 4D: representative immunoblot of replication stress and cell death biomarkers in MIAPACA2 PDAC cells treated with HCT13 (10 nM)+Cu(II) (20 μM). FIG. 4E: Annexin V/PI staining in MIAPACA2 cells to validate the synergistic interaction of HCT13 (25 nM)+Cu(II) (20 μM) with ATRi (250 nM VE-822) treated for 72h. FIG. 4F: trypan blue viability staining in MIAPACA2 cells to validate the synergistic interaction of HCT13 (25 nM) with ATRi (250 nM VE-822) treated for 72h in presence of Cu(II) (20 μM). FIG. 4G shows the nucleotide pool measurements by LC-MS/MS-MRM in MIAPACA-2 cells treated with 25 nM HCT-13+ Cu(II) for 48 hours. (mean±SD, n=2, one-way ANOVA corrected for multiple comparisons by Bonferroni adjustment, * P<0.05;  P<0.01; * P<0.001; **** P<0.0001).

FIG. 5A: rescue of HCT-13 (25 nM)-induced cell death by Uridine (rU) (200 μM), Pyruvate (1 mM), or both following 48h of treatment. FIG. 5B: measurement of DHODH activity using recombinant DHODH assay following treatment with indicated perturbations for 2 min. DHODH inhibitor used: NITD-982-1 μM; HCT-13-100 nM, 1 μM, (100 nM data shown); Cu(II)—20 μM. (mean±SD, n=2, Student t-test, * $P<0.05$).

FIG. 6A: assay quality, as measured by Z-factor (Z') scores (FIG. 6B and FIG. 6C) Annexin V/PI staining and Trypan Blue staining in CFPAC-1 PDAC cells and C4-2 PC cells to validate the synergistic interaction of HCT-13 with ATRi (250 nM VE-822) treated for 72h in presence of Cu(II) (20 μM). (mean±SD, n=2, one-way ANOVA corrected for multiple comparisons by Bonferroni adjustment, * $P<0.05$;  $P<0.01$; * $P<0.001$; **** $P<0.0001$).

FIG. 9A: dose and schedule for the efficacy study in p185 pre-B-ALL mice. FIGS. 9B-9D: bioluminescence images and quantification of whole body radiance of mice treated with HCT-16 (n=5) or vehicle control (n=10). FIG. 9E: dose and schedule for the efficacy study in MV4-11 AML bearing mice. FIGS. 9F-9H: bioluminescence images and quantification of whole body radiance of mice treated with HCT-16 (n=5) or vehicle control (n=5). (mean±SD, n=2, student's paired t-test, * $P<0.05$;  $P<0.01$; * $P<0.001$). q.d.=once/day. For purposes of the disclosure, Cu(HCT-13) is the same as compound HCT-16 (i.e., copper complexed with HCT-13).

DETAILED DESCRIPTION

Figure 1A:
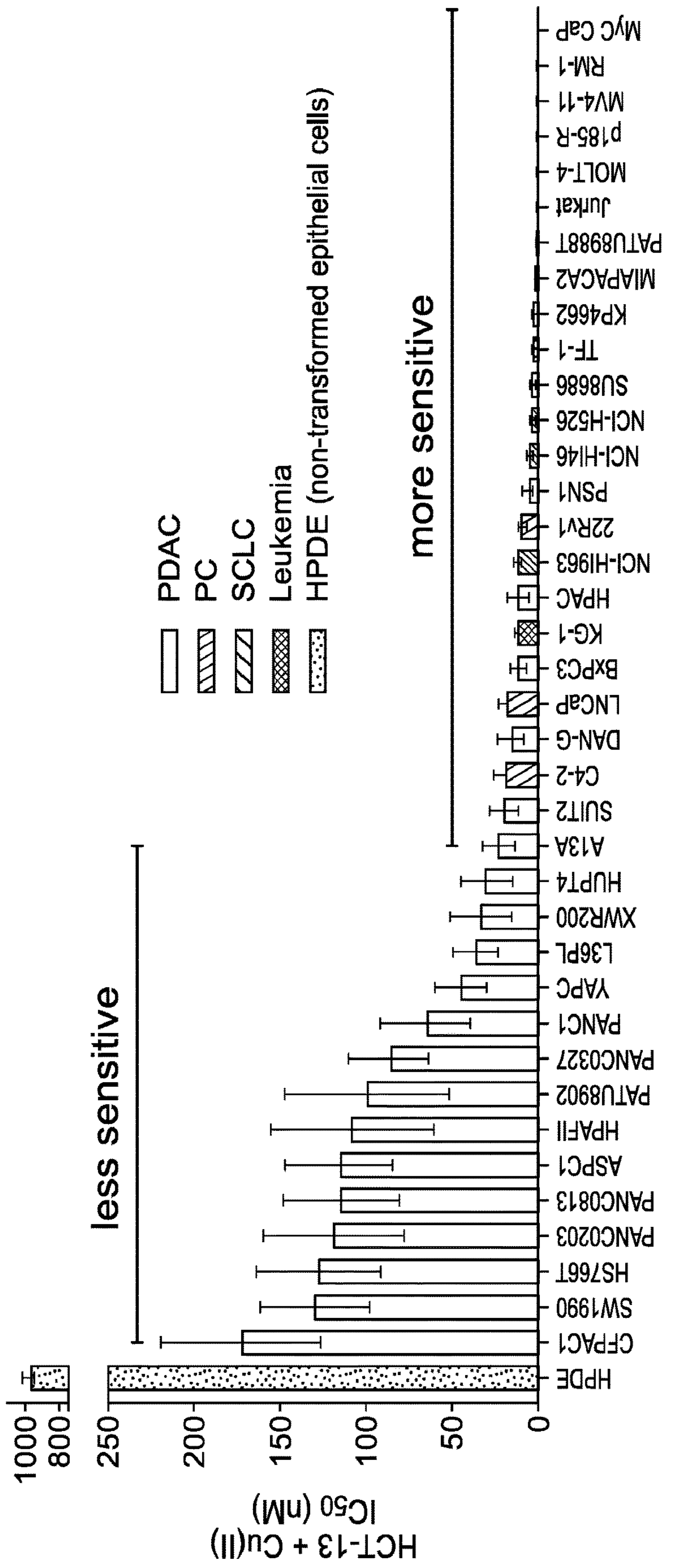
FIGS. 1A-1U show that copper potentiates the toxicity of the disclosed compounds against cancer models.

The inventors discovered a potent class of isoquinoline-based α-N-heterocyclic carboxaldehyde thiosemicarbazone (HCT) compounds, and synthesized a series of antiproliferative agents through iterative rounds of methylation and fluorination modifications, and unexpectedly discovered synergy between isoquinoline fluorination and 4' amine methylation and demonstrated that incubation of these compounds with physiologically relevant levels of metal or metal salts (e.g., $CuCl_2$) further potentiated their activity. The compounds described herein are highly potent against a panel of pancreatic, small cell lung carcinoma, prostate, and leukemia cancer models. The inventors show that the cytotoxicity of the compounds is metal-dependent (e.g., copper-dependent), and induces production of reactive oxygen species (ROS), and promotes mitochondrial dysfunction and S-phase arrest. The inventors identified the DNA damage response/replication stress response (DDR/RSR) pathways as actionable adaptive resistance mechanisms following treatment with the compounds described herein.

Definitions

The abbreviations used herein have their conventional meaning within the chemical and biological arts (e.g., —NMe is $—NCH_3$, and $—NMe_2$ is $N(CH_3)_2$). The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH{=}CHO—CH_3$, $—Si(CH_3)_3$, $—CH_2—CH{=}N—OCH_3$, $—CH{=}CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom. A heteroalkyl moiety may include two optionally different heteroatoms. A heteroalkyl moiety may include three optionally different heteroatoms. A heteroalkyl moiety may include four optionally different heteroatoms. A heteroalkyl moiety may include five optionally different heteroatoms. A heteroalkyl moiety may include up to 8 optionally different heteroatoms. The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

In embodiments, the term "cycloalkyl" means a monocyclic, bicyclic, or a multicyclic cycloalkyl ring system. In aspects, monocyclic ring systems are cyclic hydrocarbon groups containing from 3 to 8 carbon atoms, where such groups can be saturated or unsaturated, but not aromatic. In aspects, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In aspects, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In aspects, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkyl is attached to the parent molecular moiety through any carbon atom contained within the monocyclic cycloalkyl ring. In aspects, cycloalkyl groups are optionally substituted with one or two groups which are independently oxo or thia. In aspects, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkyl is attached to the parent molecular moiety through any carbon atom contained within the base ring. In aspects, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In aspects, a cycloalkenyl is a monocyclic, bicyclic, or a multicyclic cycloalkenyl ring system. In aspects, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In aspects, bicyclic cycloalkenyl rings are bridged monocyclic rings or a fused bicyclic rings. In aspects, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In aspects, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In aspects, the bridged or fused bicyclic cycloalkenyl is attached to the parent molecular moiety through any carbon atom contained within the monocyclic cycloalkenyl ring. In aspects, cycloalkenyl groups are optionally substituted with one or two groups which are independently oxo or thia. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In aspects, the multicyclic cycloalkenyl is attached to the parent molecular moiety through any carbon atom contained within the base ring. In aspects, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In aspects, heterocyclyl groups are optionally substituted with one or two groups which are independently oxo or thia. In embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In aspects, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzooxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "〰" or "-" denotes the point of attachment of a chemical moiety to the remainder of a molecule or chemical formula.

The symbol "-----" denotes a coordinate covalent bond.

The term "oxo" means an oxygen that is double bonded to a carbon atom.

The term "alkylsulfonyl," as used herein, means a moiety having the formula —$S(O_2)$—R', where R' is a substituted or unsubstituted alkyl group as defined above. R' may have a specified number of carbons (e.g., "$C_1$-$C_4$ alkylsulfonyl").

The term "alkylarylene" as an arylene moiety covalently bonded to an alkylene moiety (also referred to herein as an alkylene linker). In aspects, the alkylarylene group has the formula:

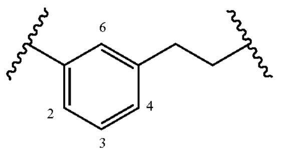

or

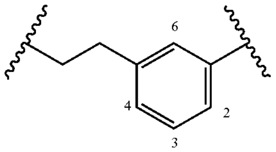

.

An alkylarylene moiety may be substituted (e.g. with a substituent group) on the alkylene moiety or the arylene linker (e.g. at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$— $SO_3H$, —$OSO_3H$, —$SO_2NH_2$, —$NHNH_2$, —$ONH_2$, —$NHC(O)NHNH_2$, substituted or unsubstituted $C_1$-$C_5$ alkyl or substituted or unsubstituted 2 to 5 membered heteroalkyl). In aspects, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O)NR"R"', —NR"C$(O)_2$R', —NR—C(NR'R"R"')=NR"", —NR—C(NR'R")=NR"', —S(O)R', —S$(O)_2$R', —S$(O)_2$NR'R", —NR$SO_2$R', —NR'NR'R"', —ONR'R", —NR'C(O)NR"NR"'R"", —CN, —$NO_2$, —NR'$SO_2$R", —NR'C(O)R", —NR'C(O)—OR", —NR'OR", in a number ranging from zero to (2m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C$(O)_2$R', —NR—C(NR'R"R'")=NR"", —NR—C(NR'R")=NR'", —S(O)R', —$S(O)_2$R', —$S(O)_2$NR'R", —NR$SO_2$R', —NR'NR"R'", —ONR'R", —NR'C(O)NR"NR'"R"", —CN, —$NO_2$, —R', —$N_3$, —CH$(Ph)_2$, fluoro($C_1$-$C_4$)alkoxy, and fluoro($C_1$-$C_4$)alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily. found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—$(CRR')_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-$(CH_2)_r$—B—, wherein A and B are independently —CRR'—, —O—, —NR—, —S—, —S(O)—, —$S(O)_2$—, —$S(O)_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —$(CRR')_s$—X'— $(C"R"R'")_d$—, where s and d are independently integers of from 0 to 3, and X' is —O—, —NR'—, —S—, —S(O)—, —$S(O)_2$—, or —$S(O)_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties: (A) oxo, halogen, —$CCl_3$, —$CBr_3$, —$CF_3$, —$CI_3$, $CHCl_2$, —$CHBr_2$, —$CHF_2$, —$CHI_2$, —$CH_2$Cl, —$CH_2$Br, —$CH_2$F, —$CH_2$I, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —NH$SO_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2$Cl, —$OCH_2$Br, —$OCH_2$I, —$OCH_2$F, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl, heteroalkyl, cycloalkyl, heterocycloalkyl, aryl, heteroaryl, substituted with at least one substituent selected from: (i) oxo, halogen, —$CCl_3$, —$CBr_3$, —$CF_3$, —$CI_3$, —$CHCl_2$, —$CHBr_2$, —$CHF_2$, —$CHI_2$, —$CH_2$Cl, —$CH_2$Br, —$CH_2$F, —$CH_2$I, —CN, —OH, —$NH_2$, —COOH, —$CONH_2$, —$NO_2$, —SH, —$SO_3$H, —$SO_4$H, —$SO_2NH_2$, —$NHNH_2$, —$ONH_2$, —NHC(O)$NHNH_2$, —NHC(O)$NH_2$, —NH$SO_2$H, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2$Cl, —$OCH_2$Br, —$OCH_2$I, —$OCH_2$F, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl, heteroalkyl, cycloalkyl, heterocycloalkyl, aryl, heteroaryl, substituted with at least one substituent selected from: (a) oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl, heteroalkyl, cycloalkyl, heterocycloalkyl, aryl, heteroaryl, substituted with at least one substituent selected from: oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$—$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A “size-limited substituent” or “size-limited substituent group,” as used herein, means a group selected from all of the substituents described above for a “substituent group,” wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A “lower substituent” or“lower substituent group,” as used herein, means a group selected from all of the substituents described above for a “substituent group,” wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In embodiments, each substituted group described in the compounds herein is substituted with at least one substituent group. More specifically, in embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In aspects, at least one or all of these groups are substituted with at least one size-limited substituent group. In aspects, at least one or all of these groups are substituted with at least one lower substituent group.

In embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In aspects of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In aspects, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene.

In aspects, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In aspects, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In aspects, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In aspects, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In aspects, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In aspects, if the substituted moiety is substituted with a plurality of groups selected from substituent groups, size-limited substituent groups, and lower substituent groups; each substituent group, size-limited substituent group, and/or lower substituent group is different.

Certain compounds of the disclosure possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the disclosure. The compounds of the disclosure do not include those that are known in art to be too unstable to synthesize and/or isolate. The disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the disclosure, whether radioactive or not, are encompassed within the scope of the disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^3$ and optionally differently.

A "detectable agent" or "detectable moiety" is a composition detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{32}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, 94Tc, 94Tc, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide nanoparticles, USPIO nanoparticle aggregates, superparamagnetic iron oxide nanoparticles, SPIO nanoparticle aggregates, monochrystalline iron oxide nanoparticles, monochrystalline iron oxide, nanoparticle contrast agents, liposomes or other delivery vehicles containing Gadolinium chelate molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}F$, $^{32}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{68}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{42}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{19}Au$, $^{198}Au$, $^{211}At$, $^{211}Pb$, $^{212}Bi$, $^{212}Pb$, $^{213}Bi$, $^{223}Ra$ and $^{225}Ac$. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, pancreatic ductal adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term "solid tumor" refers to a malignant mass of tissue that does not contain cysts or liquid areas. Exemplary solid tumors include sarcomas, carcinomas, and lymphomas.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cutaneous T-cell lymphoma, peripheral T-cell lymphoma, anaplastic large cell lymphoma, mycosis fungoides, and precursor T-lymphoblastic lymphoma.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the terms "metastasis," "metastatic," and "metastatic cancer" can be used interchangeably and refer to the spread of a proliferative disease or disorder, e.g., cancer, from one organ or another non-adjacent organ or body part. "Metastatic cancer" is also called "Stage IV cancer." Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In aspects, a control is the measurement of the activity of a protein in the absence of a compound as described herein (including embodiments and examples).

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

An "anticancer agent" as used herein refers to a molecule (e.g. compound, peptide, protein, nucleic acid) used to treat cancer through destruction or inhibition of cancer cells or tissues. Anticancer agents may be selective for certain cancers or certain tissues. In aspects, anticancer agents herein may include epigenetic inhibitors and multi-kinase inhibitors.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In aspects, an anti-cancer agent is a chemotherapeutic. In aspects, an anti-cancer agent is an agent identified herein having utility in methods of treating cancer. In aspects, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethlymelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators;

apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride;

elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin I1 (including recombinant interleukin IL, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, inanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

"Radiation therapy" refers to a cancer treatment that uses radiation to kill cancer cells and/or shrink tumors. Radiation therapy includes external beam radiation therapy and internal radiation therapy (e.g., brachytherapy). The radiation therapy can be local or systemic. Exemplary radiation therapy includes intensity modulated radiation therapy, image-guided radiation therapy, 3-dimensional conformal radiation therapy, volumetric modulated radiation therapy, particle therapy (e.g., proton therapy), stereotactic radiosurgery, Gamma Knife®, iodine-131, strontium-89, samarium ($^{153}$Sm) lexidronam, radium-223, and radioimmunotherapy (e.g., anti-CD20 monoclonal antibody conjugated to $^{111}$In, $^{90}$Y, or $^{131}$I). Radiation therapy can optionally be accompanied by radiosensitizing drugs, such as cisplatin, minorazole, cetuximab, and the like.

"Selective" or "selectivity" or the like of a compound refers to the compound's ability to discriminate between molecular targets.

"Specific", "specifically", "specificity", or the like of a compound refers to the compound's ability to cause a particular action, such as inhibition, to a particular molecular target with minimal or no action to other proteins in the cell.

The term "pharmaceutically acceptable salts" is meant to include salts of the active compounds that are prepared with relatively nontoxic acids or bases, depending on the particular substituents found on the compounds described herein. When compounds of the disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al, Journal of Pharmaceutical Science, 1977, 66:1-19). Certain specific compounds of the disclosure contain both basic and acidic functionalities that allow the compounds to be converted into either base or acid addition salts.

Thus, the compounds of the disclosure may exist as salts, such as with pharmaceutically acceptable acids. The disclosure includes such salts. Non-limiting examples of such salts include hydrochlorides, hydrobromides, phosphates, sulfates, methanesulfonates, nitrates, maleates, acetates, citrates, fumarates, propionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the disclosure provides compounds, which are in a prodrug form. Prodrugs of the compounds described herein are those compounds that readily undergo chemical changes under physiological conditions to provide the compounds of the disclosure. Prodrugs of the compounds described herein may be converted in vivo after administration. Additionally, prodrugs can be converted to the compounds of the disclosure by chemical or biochemical methods in an ex vivo environment, such as, for example, when contacted with a suitable enzyme or chemical reagent.

Certain compounds of the disclosure can exist in unsolvated forms as well as solvated forms, including hydrated forms. In general, the solvated forms are equivalent to unsolvated forms and are encompassed within the scope of the disclosure. Certain compounds of the disclosure may exist in multiple crystalline or amorphous forms. In general, all physical forms are equivalent for the uses contemplated by the disclosure and are intended to be within the scope of the disclosure.

As used herein, the term "about" means a range of values including the specified value, which a person of ordinary skill in the art would consider reasonably similar to the specified value. In aspects, about means within a standard deviation using measurements generally acceptable in the art. In aspects, about means a range extending to +/−10% of the specified value. In aspects, about includes the specified value.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In aspects, treating is preventing. In aspects, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In aspects, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In aspects, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In aspects, the administering does not include administration of any active agent other than the recited active agent.

"Co-administer" it is meant that a composition described herein is administered at the same time, just prior to, or just after the administration of one or more additional therapies.

The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the disclosure can be delivered transdermally, by a topical route, or formulated as applicator sticks, solutions, suspensions, emulsions, gels, creams, ointments, pastes, jellies, paints, powders, and aerosols.

"Electronegative" refers to the chemical property of atom, atoms, or moiety that attract electrons (e.g., a bonding pair of electrons) to itself. Electronegativity is affected by the atomic number and the distance between the valence electrons and its nucleus.

"ATR kinase inhibitor" as used herein refers to an inhibitor of ataxia telangiectasia and rad3-related (ATR) kinase, a DNA damage response kinase, with potential antineoplastic activity. ATR, a serine/threonine protein kinase, plays a key role in DNA repair, cell cycle progression, and survival, and is activated by DNA damage caused during DNA replication-associated stress. Exemplary ATR kinase inhibitors include berzosertib, VE-821 (i.e., 3-amino-6-(4-(methylsulfonyl)phenyl)-N-phenylpyrazine-2-carboxamide), ceralasertib (formerly AZD6738), schisandrin B, NU6027 (i.e., 4-cyclohexylmethoxy-2,6-diamino-5-nitrosopyrimidine), dactolisib, AZ20 (i.e., 4{4-[(3R)3-methylmorpholin-4-yl]-6-[1-(methylsulfonyl)cyclopropyl]pyrimidin-2-yl}1-H-indole), caffeine, wortmannin, or an analog of any one of the foregoing.

An "inhibitor" refers to a compound (e.g. compounds described herein) that reduces activity when compared to a control, such as absence of the compound or a compound with known inactivity.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In aspects contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In aspects activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In aspects inhibition means negatively affecting (e.g. decreasing) the concentration or levels of the protein relative to the concentration or level of the protein in the absence of the inhibitor. In aspects inhibition refers to reduction of a disease or symptoms of disease. In aspects, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In aspects, inhibition refers to a reduction of activity of a target protein resulting from a direct interaction (e.g. an inhibitor binds to the target protein). In aspects, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "protecting group" is used in accordance with its ordinary meaning in organic chemistry and refers to a moiety covalently bound to a heteroatom, heterocycloalkyl, or heteroaryl to prevent reactivity of the heteroatom, heterocycloalkyl, or heteroaryl during one or more chemical reactions performed prior to removal of the protecting group. Typically a protecting group is bound to a heteroatom (e.g., O) during a part of a multipart synthesis wherein it is not desired to have the heteroatom react (e.g., a chemical reduction) with the reagent. Following protection the protecting group may be removed (e.g., by modulating the pH). In aspects, the protecting group is an alcohol protecting group. Non-limiting examples of alcohol protecting groups include acetyl, benzoyl, benzyl, methoxymethyl ether (MOM), tetrahydropyranyl (THP), and silyl ether (e.g., trimethylsilyl (TMS)). In aspects, the protecting group is an amine protecting group. Non-limiting examples of amine protecting groups include carbobenzyloxy (Cbz), tert-butyloxycarbonyl (BOC), 9-fluorenylmethyloxycarbonyl (FMOC), acetyl, benzoyl, benzyl, carbamate, p-methoxybenzyl ether (PMB), and tosyl (Ts).

In this disclosure, "comprises," "comprising," "containing" and "having" and the like can have the meaning ascribed to them in U.S. Patent law and can mean "includes," "including," and the like. "Consisting essentially of or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Compounds

The disclosure provides compounds of Formula (I), pharmaceutically acceptable salts of the compound of Formula (I), metal complexes of the compound of Formula (I), and pharmaceutically acceptable salts of metal complexes of the compound of Formula (I), where the compound of Formula (I) is:

(I)

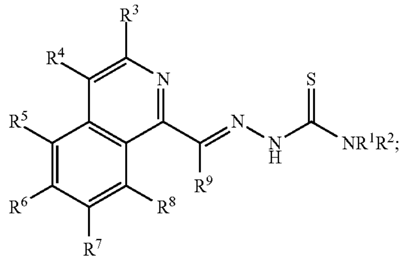

where the substituents are as defined herein. In aspects, the disclosure provides compounds of Formula (I). In aspects, the disclosure provides pharmaceutically acceptable salts of the compound of Formula (I). In aspects, the disclosure provides metal complexes of the compound of Formula (I). In aspects, the disclosure provides pharmaceutically acceptable salts of metal complexes of the compound of Formula (I).

In the compound of Formula (I), $R^1$ and $R^2$ are each independently hydrogen, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, a substituted or unsubstituted heteroaryl, or a substituted or unsubstituted alkylarylene; or $R^1$ and $R^2$ together with the nitrogen atom to which they are attached form a substituted or unsubstituted 3 to 6 membered heterocycloalkyl.

In aspects, $R^1$ and $R^2$ are each independently hydrogen, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, a substituted or unsubstituted heteroaryl, or a substituted or unsubstituted alkylarylene.

In aspects, $R^1$ and $R^2$ together with the nitrogen atom to which they are attached form a substituted or unsubstituted 3 to 6 membered heterocycloalkyl. In aspects, $R^1$ and $R^2$ together with the nitrogen atom to which they are attached form a substituted or unsubstituted 3 to 6 membered heterocycloalkyl, where the nitrogen atom is the only heteroatom in the ring. In aspects, $R^1$ and $R^2$ together with the nitrogen atom to which they are attached form a substituted 3 to 6 membered heterocycloalkyl, where the nitrogen atom is the only heteroatom in the ring. In aspects, $R^1$ and $R^2$ together with the nitrogen atom to which they are attached form an unsubstituted 3 to 6 membered heterocycloalkyl, where the nitrogen atom is the only heteroatom in the ring. In aspects, $R^1$ and $R^2$ together with the nitrogen atom to which they are attached form an unsubstituted 3 membered heterocycloalkyl, where the nitrogen atom is the only heteroatom in the ring. In aspects, $R^1$ and $R^2$ together with the nitrogen atom to which they are attached form an unsubstituted 4 membered heterocycloalkyl, where the nitrogen atom is the only heteroatom in the ring. In aspects, $R^1$ and $R^2$ together with the nitrogen atom to which they are attached form an unsubstituted 5 membered heterocycloalkyl, where the nitrogen atom is the only heteroatom in the ring. In aspects, $R^1$ and $R^2$ together with the nitrogen atom to which they are attached form an unsubstituted 6 membered heterocycloalkyl, where the nitrogen atom is the only heteroatom in the ring.

In the compound of Formula (I), $R^3$, $R^4$, $R^5$, $R^6$, $R^7$, $R^8$, and $R^9$ are each independently hydrogen or an electronegative moiety. In aspects, the electronegative moiety is halogen, —$NH_2$, —OH, —$NO_2$, —SH, —CN, —$N_3$, an alkylamine, selenide, a thioether, an aldehyde, a ketone, a carboxylic acid, a carboxylic ester, an amide, an acyl halide, an ether, a thioether, phosphorous, phosphite, phosphate, a phosphonic acid, a phosphonic ester, a phosphonate, sulfonic acid, a sulfonyl, a sulfonamide, a quaternary ammonium amine, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene. In aspects, the substituted alkyl is an alkyl substituted with one or more fluorine, chlorine, bromine, iodine or a combination thereof. In aspects, the substituted alkyl is —$CF_3$ or —$CF_2CF_3$. In aspects, the sulfonyl is tosyl, nosyl, brosyl, mesyl, or triflyl. In aspects, the electronegative moiety is an alkylamine (e.g., —NH($C_{1-6}$ alkyl); —N($C_{1-6}$ alkyl)($C_{1-6}$ alkyl)). In aspects, the electronegative moiety is halogen. In aspects, the electronegative moiety is chlorine or fluorine. In aspects, the electronegative moiety is fluorine.

In aspects of the compound of Formula (I), $R^1$, $R^2$, $R^3$, $R^4$, $R^5$, $R^6$, $R^7$, $R^8$, and $R^9$ are not concurrently hydrogen. In aspects of the compound of Formula (I), $R^5$ is not —$NHCH_3$ when $R^1$, $R^2$, $R^3$, $R^4$, $R^6$, $R^7$, $R^8$, and $R^9$ are hydrogen. In aspects of the compound of Formula (I), $R^5$ is not —$NH_2$ when $R^1$, $R^2$, $R^3$, $R^4$, $R^6$, $R^7$, $R^8$, and $R^9$ are hydrogen. In aspects of the compound of Formula (I), $R^1$ is not methyl when $R^2$, $R^3$, $R^4$, $R^5$, $R^6$, $R^7$, $R^8$, and $R^9$ are hydrogen.

In embodiments of the compound of Formula (I), $R^1$ and $R^2$ are each independently hydrogen or substituted or unsubstituted alkyl; $R^3$ is hydrogen; $R^4$, $R^5$, and $R^6$ are each independently hydrogen or the electronegative moiety; and $R^7$, $R^8$, and $R^9$ are hydrogen. In aspects, the electronegative moiety is halogen, —$NH_2$, —OH, —$NO_2$, —SH, —CN, —$N_3$, an alkylamine, selenide, a thioether, an aldehyde, a ketone, a carboxylic acid, a carboxylic ester, an amide, an acyl halide, an ether, a thioether, phosphorous, phosphite, phosphate, a phosphonic acid, a phosphonic ester, a phosphonate, sulfonic acid, a sulfonyl, a sulfonamide, a quaternary ammonium amine, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene. In aspects, the substituted alkyl is an alkyl substituted with one or more fluorine, chlorine, bromine, iodine or a combination thereof. In aspects, the substituted alkyl is —$CF_3$ or —$CF_2CF_3$. In aspects, the sulfonyl is tosyl, nosyl, brosyl, mesyl, or triflyl. In aspects, the electronegative moiety is halogen. In aspects, the electronegative moiety is chlorine, fluorine, bromine, or iodine. In aspects, the electronegative moiety is chlorine or fluorine. In aspects, the electronegative moiety is fluorine.

In embodiments of the compound of Formula (I), $R^1$ and $R^2$ are each independently hydrogen or a substituted or unsubstituted $C_1$-$C_4$ alkyl; $R^3$ is hydrogen; $R^4$ is hydrogen or halogen; $R^5$ is hydrogen, halogen, —$NH_2$, or an alkylamine; $R^6$ is hydrogen or halogen; and $R^7$, $R^8$, and $R^9$ are hydrogen.

In embodiments of the compound of Formula (I), $R^1$ and $R^2$ are each independently hydrogen, —$CH_3$, or —$CH_2CH_3$. In aspects, $R^1$ is hydrogen and $R^2$ is a substituted or unsubstituted $C_1$-$C_4$ alkyl. In aspects, $R^1$ is hydrogen and $R^2$ is an unsubstituted $C_1$-$C_4$ alkyl. In aspects, $R^1$ is a substituted or unsubstituted $C_1$-$C_4$ alkyl and $R^2$ is a substituted or unsubstituted $C_1$-$C_4$ alkyl. In aspects, $R^1$ is an unsubstituted $C_1$-$C_4$ alkyl and $R^2$ is an unsubstituted $C_1$-$C_4$ alkyl. In aspects, $R^1$ is hydrogen and $R^2$ is hydrogen. In aspects, $R^1$ is hydrogen and $R^2$ is —$CH_3$. In aspects, $R^1$ is hydrogen and $R^2$ is —$CH_2CH_3$. In aspects, $R^1$ is —$CH_3$ and $R^2$ is —$CH_3$. In aspects, $R^1$ is —$CH_3$ and $R^2$ is —$CH_2CH_3$. In aspects, $R^1$ is —$CH_2CH_3$ and $R^2$ is —$CH_2CH_3$.

In embodiments of the compound of Formula (I), $R^4$ is hydrogen and $R^6$ is hydrogen. In aspects, $R^4$ is hydrogen and $R^6$ is halogen. In aspects, the halogen is chlorine, fluorine, or bromine. In aspects, $R^4$ is halogen and $R^6$ is hydrogen. In aspects, the halogen is chlorine, fluorine, or bromine. In aspects, $R^4$ is halogen and $R^6$ is halogen. In aspects, the halogen is chlorine, fluorine, or bromine. In aspects, $R^4$ is hydrogen and $R^6$ is chlorine or fluorine. In aspects, $R^4$ is chlorine or fluorine, and $R^6$ is hydrogen. In aspects, $R^4$ is chlorine or fluorine and $R^6$ is chlorine or fluorine. In aspects, $R^4$ is hydrogen and $R^6$ is fluorine. In aspects, $R^4$ is fluorine, and $R^6$ is hydrogen. In aspects, $R^4$ is fluorine and $R^6$ is fluorine.

In embodiments of the compound of Formula (I), $R^5$ is hydrogen, halogen, —$NH_2$, —NH($C_1$-$C_4$ alkyl), or —N($C_1$-$C_4$ alkyl)($C_1$-$C_4$ alkyl). In aspects, $R^5$ is hydrogen, halogen, —$NH_2$, —$NHCH_3$, —NH($CH_2CH_3$), or —N($C_1$-$C_2$ alkyl)($C_1$-$C_2$ alkyl). In aspects, $R^5$ is hydrogen, halogen, —$NH_2$ or —$NHCH_3$. In aspects, $R^5$ is hydrogen. In aspects, $R^5$ is halogen. In aspects, $R^5$ is chlorine or fluorine. In aspects, $R^5$ is fluorine. In aspects, $R^5$ is-NH($C_1$-$C_4$ alkyl). In aspects, $R^5$ is —NH($C_1$-$C_2$ alkyl). In aspects, $R^5$ is-N($C_1$-$C_4$ alkyl)($C_1$-$C_4$ alkyl). In aspects, $R^5$ is —N($C_1$-$C_2$ alkyl)($C_1$-$C_2$ alkyl). In aspects, $R^5$ is —$NH_2$. In aspects, $R^5$ is —$NHCH_3$. In aspects, $R^5$ is —NH($CH_2CH_3$). In aspects, $R^5$ is N$(CH_3)_2$. In aspects, $R^5$ is N($CH_3$)($CH_2CH_3$). In aspects, $R^5$ is N($CH_2CH_3$)($CH_2CH_3$).

In embodiments, the compound of Formula (I) is a compound of Formula (Ia), a pharmaceutically acceptable salt of the compound of Formula (Ia), a metal complex of the compound of Formula (Ia), or a pharmaceutically acceptable salt of a metal complex of the compound of Formula (Ia), where the compound of Formula (Ia) is:

(Ia)

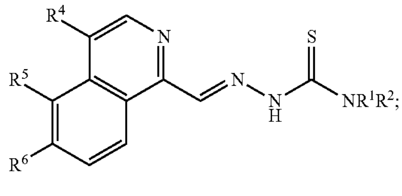

wherein $R^1$ and $R^2$ are each independently hydrogen or an unsubstituted $C_{1-4}$ alkyl; and $R^4$, $R^5$, and $R^6$ are each independently hydrogen, fluorine, chlorine, bromine, iodine, —$NH_2$, —NH($C_{1-4}$ alkyl), or —N($C_{1-4}$ alkyl)($C_{1-4}$ alkyl). In aspects, $R^1$ and $R^2$ are each independently hydrogen, —$CH_3$, or $CH_2CH_3$; and $R^4$, $R^5$, and $R^6$ are each independently hydrogen, fluorine, chlorine, bromine, iodine, —$NH_2$, —$NHCH_3$, —$NHCH_2CH_3$, —N$(CH_3)_2$, —N($CH_3$)($CH_2CH_3$), or —N$(CH_2CH_3)_2$. In aspects, $R^1$ and $R^2$ are each independently hydrogen, —$CH_3$, or $CH_2CH_3$; and $R^4$, $R^5$, and $R^6$ are each independently hydrogen, fluorine, $NH_2$, —$NHCH_3$, —$NHCH_2CH_3$, —N$(CH_3)_2$, —N($CH_3$)($CH_2CH_3$), or —N$(CH_2CH_3)_2$. In aspects, $R^1$ and $R^2$ are each independently hydrogen, —$CH_3$, or $CH_2CH_3$; $R^4$ and $R^6$ are each independently hydrogen, fluorine, chlorine, bromine, or iodine; and $R^5$ is hydrogen, $NH_2$, —$NHCH_3$, —$NHCH_2CH_3$, —N$(CH_3)_2$, —N($CH_3$)($CH_2CH_3$), or —N$(CH_2CH_3)_2$. In aspects, $R^1$ and $R^2$ are each independently hydrogen, —$CH_3$, or $CH_2CH_3$; $R^4$ and $R^6$ are each independently hydrogen or fluorine; and $R^5$ is hydrogen, $NH_2$, $-NHCH_3$, or $-NHCH_2CH_3$. In aspects, at least one of $R^4$, $R^5$, and $R^6$ are hydrogen. In aspects, at least two of $R^4$, $R^5$, and $R^6$ are hydrogen. For the substituents in the compound of Formula (Ia) the following proviso apply: (i) $R^1$, $R^2$, $R^4$, $R^5$, and $R^6$ are not all hydrogen; (ii) $R^5$ is not $-NHCH_3$ when $R^1$, $R^2$, $R^3$, $R^4$, and $R^6$ are hydrogen; (iii) $R^5$ is not $-NH_2$ when $R^1$, $R^2$, $R^3$, $R^4$, and $R^6$ are hydrogen; and (iv) $R^1$ is not methyl when $R^2$, $R^3$, $R^4$, $R^5$, and $R^6$ are hydrogen. In aspects, the disclosure provides compounds of Formula (Ia). In aspects, the disclosure provides pharmaceutically acceptable salts of the compound of Formula (Ia). In aspects, the disclosure provides metal complexes of the compound of Formula (Ia). In aspects, the disclosure provides pharmaceutically acceptable salts of metal complexes of the compound of Formula (Ia).

In embodiments, the compound of Formula (I) is HCT2 (or HCT-2), a pharmaceutically acceptable salt thereof, a metal complex thereof, or a pharmaceutically acceptable salt of a metal complex thereof, where HCT2 is:

(HCT2)

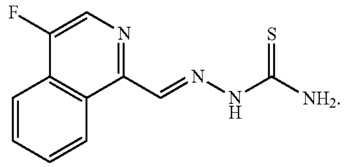

In aspects, the disclosure provides compounds of Formula (HCT2). In aspects, the disclosure provides pharmaceutically acceptable salts of the compound of Formula (HCT2). In aspects, the disclosure provides metal complexes of the compound of Formula (HCT2). In aspects, the disclosure provides pharmaceutically acceptable salts of metal complexes of the compound of Formula (HCT2).

In embodiments, the compound of Formula (I) is HCT3 (or HCT-3), a pharmaceutically acceptable salt thereof, a metal complex thereof, or a pharmaceutically acceptable salt of a metal complex thereof, where HCT3 is:

(HCT3)

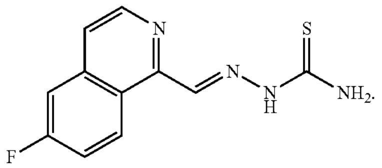

In aspects, the disclosure provides compounds of Formula (HCT3). In aspects, the disclosure provides pharmaceutically acceptable salts of the compound of Formula (HCT3). In aspects, the disclosure provides metal complexes of the compound of Formula (HCT3). In aspects, the disclosure provides pharmaceutically acceptable salts of metal complexes of the compound of Formula (HCT3).

In embodiments, the compound of Formula (I) is HCT7 (or HCT-7), a pharmaceutically acceptable salt thereof, a metal complex thereof, or a pharmaceutically acceptable salt of a metal complex thereof, where HCT7 is:

(HCT7)

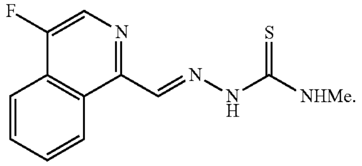

In aspects, the disclosure provides compounds of Formula (HCT7). In aspects, the disclosure provides pharmaceutically acceptable salts of the compound of Formula (HCT7). In aspects, the disclosure provides metal complexes of the compound of Formula (HCT7). In aspects, the disclosure provides pharmaceutically acceptable salts of metal complexes of the compound of Formula (HCT7).

In embodiments, the compound of Formula (I) is HCT8 (or HCT-8), a pharmaceutically acceptable salt thereof, a metal complex thereof, or a pharmaceutically acceptable salt of a metal complex thereof, where HCT8 is:

(HCT8)

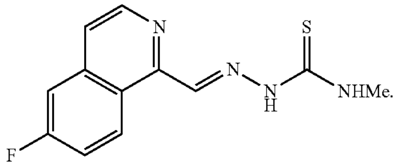

In aspects, the disclosure provides compounds of Formula (HCT8). In aspects, the disclosure provides pharmaceutically acceptable salts of the compound of Formula (HCT8). In aspects, the disclosure provides metal complexes of the compound of Formula (HCT8). In aspects, the disclosure provides pharmaceutically acceptable salts of metal complexes of the compound of Formula (HCT8).

In embodiments, the compound of Formula (I) is HCT9 (or HCT-9), a pharmaceutically acceptable salt thereof, a metal complex thereof, or a pharmaceutically acceptable salt of a metal complex thereof, where HCT9 is:

(HCT9)

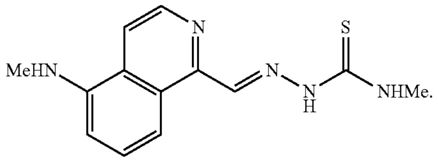

In aspects, the disclosure provides compounds of Formula (HCT9). In aspects, the disclosure provides pharmaceutically acceptable salts of the compound of Formula (HCT9). In aspects, the disclosure provides metal complexes of the compound of Formula (HCT9). In aspects, the disclosure provides pharmaceutically acceptable salts of metal complexes of the compound of Formula (HCT9).

In embodiments, the compound of Formula (I) is HCT10 (or HCT-10), a pharmaceutically acceptable salt thereof, a metal complex thereof, or a pharmaceutically acceptable salt of a metal complex thereof, where HCT10 is:

(HCT10)

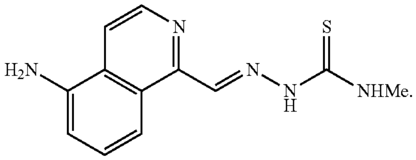

In aspects, the disclosure provides compounds of Formula (HCT10). In aspects, the disclosure provides pharmaceutically acceptable salts of the compound of Formula (HCT10). In aspects, the disclosure provides metal complexes of the compound of Formula (HCT10). In aspects, the disclosure provides pharmaceutically acceptable salts of metal complexes of the compound of Formula (HCT10).

In embodiments, the compound of Formula (I) is HCT11 (or HCT-11), a pharmaceutically acceptable salt thereof, a metal complex thereof, or a pharmaceutically acceptable salt of a metal complex thereof, where HCT11 is:

(HCT11)

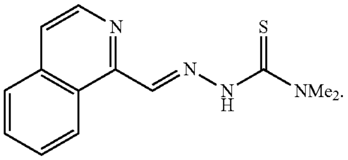

In aspects, the disclosure provides compounds of Formula (HCT11). In aspects, the disclosure provides pharmaceutically acceptable salts of the compound of Formula (HCT11). In aspects, the disclosure provides metal complexes of the compound of Formula (HCT11). In aspects, the disclosure provides pharmaceutically acceptable salts of metal complexes of the compound of Formula (HCT11).

In embodiments, the compound of Formula (I) is HCT12 (or HCT-12), a pharmaceutically acceptable salt thereof, a metal complex thereof, or a pharmaceutically acceptable salt of a metal complex thereof, where HCT12 is:

(HCT12)

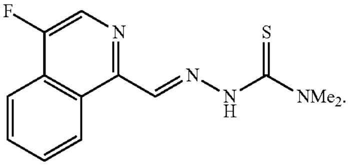

In aspects, the disclosure provides compounds of Formula (HCT12). In aspects, the disclosure provides pharmaceutically acceptable salts of the compound of Formula (HCT12). In aspects, the disclosure provides metal complexes of the compound of Formula (HCT12). In aspects, the disclosure provides pharmaceutically acceptable salts of metal complexes of the compound of Formula (HCT12).

In embodiments, the compound of Formula (I) is HCT13 (or HCT-13), a pharmaceutically acceptable salt thereof, a metal complex thereof, or a pharmaceutically acceptable salt of a metal complex thereof, where HCT13 is:

(HCT13)

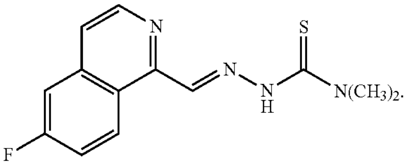

In aspects, the disclosure provides compounds of Formula (HCT13). In aspects, the disclosure provides pharmaceutically acceptable salts of the compound of Formula (HCT13). In aspects, the disclosure provides metal complexes of the compound of Formula (HCT13). In aspects, the disclosure provides pharmaceutically acceptable salts of metal complexes of the compound of Formula (HCT13).

In embodiments, the compound of Formula (I) is HCT14 (or HCT-14), a pharmaceutically acceptable salt thereof, a metal complex thereof, or a pharmaceutically acceptable salt of a metal complex thereof, where HCT14 is:

(HCT14)

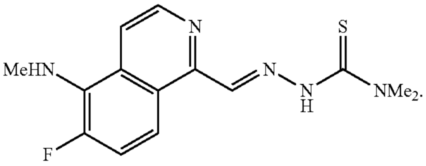

In aspects, the disclosure provides compounds of Formula (HCT14). In aspects, the disclosure provides pharmaceutically acceptable salts of the compound of Formula (HCT14). In aspects, the disclosure provides metal complexes of the compound of Formula (HCT14). In aspects, the disclosure provides pharmaceutically acceptable salts of metal complexes of the compound of Formula (HCT14).

In embodiments, the compound of Formula (I) is HCT15 (or HCT-15), a pharmaceutically acceptable salt thereof, a metal complex thereof, or a pharmaceutically acceptable salt of a metal complex thereof, where HCT15 is:

(HCT15)

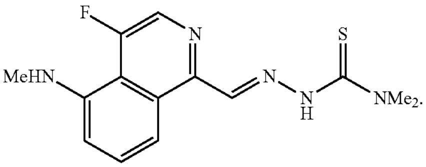

In aspects, the disclosure provides compounds of Formula (HCT15). In aspects, the disclosure provides pharmaceutically acceptable salts of the compound of Formula (HCT15). In aspects, the disclosure provides metal complexes of the compound of Formula (HCT15). In aspects, the disclosure provides pharmaceutically acceptable salts of metal complexes of the compound of Formula (HCT15).

The disclosure provides compounds of Formula (II), and pharmaceutically acceptable salts of the compound of Formula (II), where the compound of Formula (II) is:

(II)

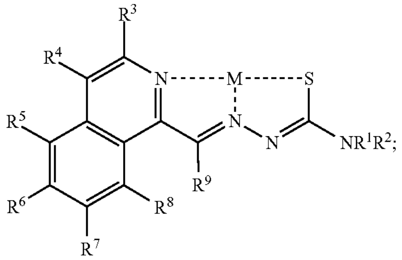

where the substituents are as defined herein. In aspects, the disclosure provides compounds of Formula (II). In aspects, the disclosure provides pharmaceutically acceptable salts of the compound of Formula (II).

In the compound of Formula (II), $R^1$ and $R^2$ are each independently hydrogen, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, a substituted or unsubstituted heteroaryl, or a substituted or unsubstituted alkylarylene; or $R^1$ and $R^2$ together with the nitrogen atom to which they are attached form a substituted or unsubstituted 3 to 6 membered heterocycloalkyl.

In embodiments of the compound of Formula (II), $R^1$ and $R^2$ are each independently hydrogen, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, a substituted or unsubstituted heteroaryl, or a substituted or unsubstituted alkylarylene.

In embodiments of the compound of Formula (II), $R^1$ and $R^2$ together with the nitrogen atom to which they are attached form a substituted or unsubstituted 3 to 6 membered heterocycloalkyl. In aspects, $R^1$ and $R^2$ together with the nitrogen atom to which they are attached form a substituted or unsubstituted 3 to 6 membered heterocycloalkyl, where the nitrogen atom is the only heteroatom in the ring. In aspects, $R^1$ and $R^2$ together with the nitrogen atom to which they are attached form a substituted 3 to 6 membered heterocycloalkyl, where the nitrogen atom is the only heteroatom in the ring. In aspects, $R^1$ and $R^2$ together with the nitrogen atom to which they are attached form an unsubstituted 3 to 6 membered heterocycloalkyl, where the nitrogen atom is the only heteroatom in the ring. In aspects, $R^1$ and $R^2$ together with the nitrogen atom to which they are attached form an unsubstituted 3 membered heterocycloalkyl, where the nitrogen atom is the only heteroatom in the ring. In aspects, $R^1$ and $R^2$ together with the nitrogen atom to which they are attached form an unsubstituted 4 membered heterocycloalkyl, where the nitrogen atom is the only heteroatom in the ring. In aspects, $R^1$ and $R^2$ together with the nitrogen atom to which they are attached form an unsubstituted 5 membered heterocycloalkyl, where the nitrogen atom is the only heteroatom in the ring. In aspects, $R^1$ and $R^2$ together with the nitrogen atom to which they are attached form an unsubstituted 6 membered heterocycloalkyl, where the nitrogen atom is the only heteroatom in the ring.

In the compound of Formula (II), $R^3$, $R^4$, $R^5$, $R^6$, $R^7$, $R^8$, and $R^9$ are each independently hydrogen or an electronegative moiety. In aspects, the electronegative moiety is halogen, $-NH_2$, —OH, $-NO_2$, —SH, —CN, $-N_3$, an alkylamine, selenide, a thioether, an aldehyde, a ketone, a carboxylic acid, a carboxylic ester, an amide, an acyl halide, an ether, a thioether, phosphorous, phosphite, phosphate, a phosphonic acid, a phosphonic ester, a phosphonate, sulfonic acid, a sulfonyl, a sulfonamide, a quaternary ammonium amine, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene. In aspects, the substituted alkyl is an alkyl substituted with one or more fluorine, chlorine, bromine, iodine or a combination thereof. In aspects, the substituted alkyl is $-CF_3$ or $-CF_2CF_3$. In aspects, the sulfonyl is tosyl, nosyl, brosyl, mesyl, or triflyl. In aspects, the electronegative moiety is halogen. In aspects, the electronegative moiety is chlorine, fluorine, bromine, or iodine. In aspects, the electronegative moiety is chlorine or fluorine. In aspects, the electronegative moiety is fluorine.

In embodiments of the compound of Formula (II), M is a metal salt or a metal. In aspects, M is a metal salt. In aspects, the metal salt is a copper salt. In aspects, the metal salt is a zinc salt. In aspects, the metal salt is a cobalt salt. In aspects, the metal salt is a nickel salt. In aspects, the metal salt is a magnesium salt. In aspects, the metal salt is an iron salt. In aspects, the metal salt is a manganese salt. In aspects, the metal salt is a gallium salt. In aspects, the metal salt is a germanium salt. In aspects, the metal salt is a calcium salt. In aspects, the metal salt is copper chloride. In aspects, the metal salt is copper bromide. In aspects, the metal salt is copper fluoride. In aspects, the metal salt is copper iodide. In aspects, the metal salt is copper nitrate. In aspects, the metal salt is copper perchlorate. In aspects, the metal salt is copper sulfate. In aspects, the metal salt is copper acetate. In aspects, the metal salt is copper tartrate. In aspects, M is a metal. In aspects, the metal is copper. In aspects, the metal is zinc. In aspects, the metal is cobalt. In aspects, the metal is nickel. In aspects, the metal is magnesium. In aspects, the metal is iron. In aspects, the metal is manganese. In aspects, the metal is gallium. In aspects, the metal is germanium. In aspects, the metal is calcium.

In aspects of the compound of Formula (II), $R^1$, $R^2$, $R^3$, $R^4$, $R^5$, $R^6$, $R^7$, $R^8$, and $R^9$ are not concurrently hydrogen. In aspects of the compound of Formula (II), $R^5$ is not $-NHCH_3$ when $R^1$, $R^2$, $R^3$, $R^4$, $R^6$, $R^7$, $R^8$, and $R^9$ are hydrogen. In aspects of the compound of Formula (II), $R^5$ is not $-NH_2$ when $R^1$, $R^2$, $R^3$, $R^4$, $R^6$, $R^7$, $R^8$, and $R^9$ are hydrogen. In aspects of the compound of Formula (II), $R^1$ is not methyl when $R^2$, $R^3$, $R^4$, $R^5$, $R^6$, $R^7$, $R^8$, and $R^9$ are hydrogen.

In embodiments of the compound of Formula (II), $R^1$ and $R^2$ are each independently hydrogen or substituted or unsubstituted alkyl; $R^3$ is hydrogen; $R^4$, $R^5$, and $R^6$ are each independently hydrogen or the electronegative moiety; and $R^7$, $R^8$, and $R^9$ are hydrogen. In aspects, the electronegative moiety is halogen, $-NH_2$, —OH, $-NO_2$, —SH, —CN, $-N_3$, an alkylamine, selenide, a thioether, an aldehyde, a ketone, a carboxylic acid, a carboxylic ester, an amide, an acyl halide, an ether, a thioether, phosphorous, phosphite, phosphate, a phosphonic acid, a phosphonic ester, a phosphonate, sulfonic acid, a sulfonyl, a sulfonamide, a quaternary ammonium amine, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene. In aspects, the substituted alkyl is an alkyl substituted with one or more fluorine, chlorine, bromine, iodine or a combination thereof. In aspects, the substituted alkyl is $-CF_3$ or $-CF_2CF_3$. In aspects, the sulfonyl is tosyl, nosyl, brosyl, mesyl, or triflyl. In aspects, the electronegative moiety is halogen. In aspects, the electronegative moiety is chlorine, fluorine, bromine, or iodine. In aspects, the electronegative moiety is chlorine or fluorine. In aspects, the electronegative moiety is fluorine.

In embodiments of the compound of Formula (II), $R^1$ and $R^2$ are each independently hydrogen or a substituted or unsubstituted $C_1$-$C_4$ alkyl; $R^3$ is hydrogen; $R^4$ is hydrogen or halogen; $R^5$ is hydrogen, halogen, $-NH_2$, or an alkylamine; $R^6$ is hydrogen or halogen; and $R^7$, $R^8$, and $R^9$ are hydrogen.

In embodiments of the compound of Formula (II), $R^1$ and $R^2$ are each independently hydrogen, $-CH_3$, or $-CH_2CH_3$. In aspects, $R^1$ is hydrogen and $R^2$ is a substituted or unsubstituted $C_1$-$C_4$ alkyl. In aspects, $R^1$ is hydrogen and $R^2$ is an unsubstituted $C_1$-$C_4$ alkyl. In aspects, $R^1$ is a substituted or unsubstituted $C_1$-$C_4$ alkyl and $R^2$ is a substituted or unsubstituted $C_1$-$C_4$ alkyl. In aspects, $R^1$ is an unsubstituted $C_1$-$C_4$ alkyl and $R^2$ is an unsubstituted $C_1$-$C_4$ alkyl. In aspects, $R^1$ is hydrogen and $R^2$ is hydrogen. In aspects, $R^1$ is hydrogen and $R^2$ is $-CH_3$. In aspects, $R^1$ is hydrogen and $R^2$ is $-CH_2CH_3$. In aspects, $R^1$ is $-CH_3$ and $R^2$ is $-CH_3$. In aspects, $R^1$ is $-CH_3$ and $R^2$ is $-CH_2CH_3$. In aspects, $R^1$ is $-CH_2CH_3$ and $R^2$ is $-CH_2CH_3$.

In embodiments of the compound of Formula (II), $R^4$ is hydrogen and $R^6$ is hydrogen. In aspects, $R^4$ is hydrogen and $R^6$ is halogen. In aspects, the halogen is chlorine, fluorine, or bromine. In aspects, $R^4$ is halogen and $R^6$ is hydrogen. In aspects, the halogen is chlorine, fluorine, or bromine. In aspects, $R^4$ is halogen and $R^6$ is halogen. In aspects, the halogen is chlorine, fluorine, or bromine. In aspects, $R^4$ is hydrogen and $R^6$ is chlorine or fluorine. In aspects, $R^4$ is chlorine or fluorine, and $R^6$ is hydrogen. In aspects, $R^4$ is chlorine or fluorine and $R^6$ is chlorine or fluorine. In aspects, $R^4$ is hydrogen and $R^6$ is fluorine. In aspects, $R^4$ is fluorine, and $R^6$ is hydrogen. In aspects, $R^4$ is fluorine and $R^6$ is fluorine.

In embodiments of the compound of Formula (II), $R^5$ is hydrogen, halogen, $-NH_2$, l-NH($C_1$-$C_4$ alkyl), or $-N(C_1$-$C_4$ alkyl)($C_1$-$C_4$ alkyl). In aspects, $R^5$ is hydrogen, halogen, $-NH_2$, $-NHCH_3$, $-NH(CH_2CH_3)$, or $-N(C_1$-$C_2$ alkyl) ($C_1$-$C_2$ alkyl). In aspects, $R^5$ is hydrogen, halogen, $-NH_2$ or $-NHCH_3$. In aspects, $R^5$ is hydrogen. In aspects, $R^5$ is halogen. In aspects, $R^5$ is chlorine or fluorine. In aspects, $R^5$ is fluorine. In aspects, $R^5$ is-NH($C_1$-$C_4$ alkyl). In aspects, $R^5$ is-NH($C_1$-$C_2$ alkyl). In aspects, $R^5$ is-N($C_1$-$C_4$ alkyl)($C_1$-$C_4$ alkyl). In aspects, $R^5$ is $-N(C_1$-$C_2$ alkyl)($C_1$-$C_2$ alkyl). In aspects, $R^5$ is $-NH_2$. In aspects, $R^5$ is $-NHCH_3$. In aspects, $R^5$ is $-NH(CH_2CH_3)$. In aspects, $R^5$ is $N(CH_3)_2$. In aspects, $R^5$ is $N(CH_3)(CH_2CH_3)$. In aspects, $R^5$ is $N(CH_2CH_3)(CH_2CH_3)$.

In aspects of the compound of Formula (II), $R^1$, $R^2$, $R^3$, $R^5$, $R^6$, $R^7$, $R^8$, and $R^9$ are hydrogen; $R^4$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$, $R^2$, $R^3$, $R^4$, $R^5$, $R^7$, $R^8$, and $R^9$ are hydrogen; $R^6$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ is $-CH_3$; $R^2$, $R^3$, $R^5$, $R^6$, $R^7$, $R^8$, and $R^9$ are hydrogen; $R^4$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ is $-CH_3$; $R^2$, $R^3$, $R^4$, $R^5$, $R^7$, $R^8$, and $R^9$ are hydrogen; $R^6$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ is $-CH_3$; $R^2$, $R^3$, $R^4$, $R^6$, $R^7$, $R^8$, and $R^9$ are hydrogen; $R^5$ is $-NHCH_3$; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ is $-CH_3$; $R^2$, $R^3$, $R^4$, $R^6$, $R^7$, $R^8$, and $R^9$ are hydrogen; $R^5$ is $-NH_2$; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ and $R^2$ are $-CH_3$; $R^3$, $R^4$, $R^5$, $R^6$, $R^7$, $R^8$, and $R^9$ are hydrogen; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ and $R^2$ are $-CH_3$; $R^3$, $R^5$, $R^6$, $R^7$, $R^8$, and $R^9$ are hydrogen; $R^4$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ and $R^2$ are —$CH_3$; $R^3$, $R^4$, $R^5$, $R^7$, $R^8$, and $R^9$ are hydrogen; $R^6$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ and $R^2$ are —$CH_3$; $R^3$, $R^4$, $R^7$, $R^8$, and $R^9$ are hydrogen; $R^5$ is —$NHCH_3$; $R^6$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In aspects of the compound of Formula (II), $R^1$ and $R^2$ are —$CH_3$; $R^3$, $R^6$, $R^7$, $R^8$, and $R^9$ are hydrogen; $R^5$ is —$NHCH_3$; $R^4$ is fluorine; and M is a metal salt selected from the group consisting of a copper salt, a zinc salt, a cobalt salt, a nickel salt, a magnesium salt, an iron salt, a manganese salt, a gallium salt, a germanium salt, and a calcium salt. In aspects, M is a copper salt. In aspects, M is selected from the group consisting of copper chloride, copper bromide, copper fluoride, copper iodide, copper nitrate, copper perchlorate, copper sulfate, copper acetate, or copper tartrate. In aspects, M is copper chloride.

In embodiments, the compound of Formula (II) is a compound of Formula (IIa) or a pharmaceutically acceptable salt thereof:

(IIa)

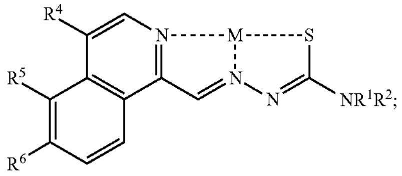

wherein $R^1$ and $R^2$ are each independently hydrogen or an unsubstituted $C_{1-4}$ alkyl; $R^4$, $R^5$, and $R^6$ are each independently hydrogen, fluorine, chlorine, bromine, iodine, —$NH_2$, —NH($C_{1-4}$ alkyl), or —N($C_{1-4}$ alkyl)($C_{1-4}$ alkyl); and M is a copper salt, a zinc salt, a cobalt salt, a nickel salt, a magnesium salt, an iron salt, a manganese salt, a gallium salt, a germanium salt, or a calcium salt. In aspects, $R^1$ and $R^2$ are each independently hydrogen, —$CH_3$, or $CH_2CH_3$; $R^4$, $R^5$, and $R^6$ are each independently hydrogen, fluorine, chlorine, bromine, iodine, —$NH_2$, —$NHCH_3$, —$NHCH_2CH_3$, —$N(CH_3)_2$, —$N(CH_3)(CH_2CH_3)$, or —$N(CH_2CH_3)_2$; and M is a copper salt, a zinc salt, a cobalt salt, a nickel salt, a magnesium salt, an iron salt, a manganese salt, a gallium salt, a germanium salt, or a calcium salt. In aspects, $R^1$ and $R^2$ are each independently hydrogen, —$CH_3$, or $CH_2CH_3$; $R^4$, $R^5$, and $R^6$ are each independently hydrogen, fluorine, $NH_2$, —$NHCH_3$, —$NHCH_2CH_3$, —$N(CH_3)_2$, —$N(CH_3)(CH_2CH_3)$, or —$N(CH_2CH_3)_2$; and M is copper chloride, copper bromide, copper fluoride, copper iodide, copper nitrate, copper perchlorate, copper sulfate, copper acetate, or copper tartrate. In aspects, $R^1$ and $R^2$ are each independently hydrogen, —$CH_3$, or $CH_2CH_3$; $R^4$ and $R^6$ are each independently hydrogen, fluorine, chlorine, bromine, or iodine; $R^5$ is hydrogen, $NH_2$, —$NHCH_3$, —$NHCH_2CH_3$, —$N(CH_3)_2$, —$N(CH_3)(CH_2CH_3)$, or —$N(CH_2CH_3)_2$; and M is a copper salt, a zinc salt, a cobalt salt, a nickel salt, a magnesium salt, an iron salt, a manganese salt, a gallium salt, a germanium salt, or a calcium salt. In aspects, $R^1$ and $R^2$ are each independently hydrogen, —$CH_3$, or $CH_2CH_3$; $R^4$ and $R^6$ are each independently hydrogen or fluorine; and $R^5$ is hydrogen, $NH_2$, —$NHCH_3$, or —$NHCH_2CH_3$; and M is copper chloride, copper bromide, copper fluoride, copper iodide, copper nitrate, copper perchlorate, copper sulfate, copper acetate, or copper tartrate. In aspects, at least one of $R^4$, $R^5$, and $R^6$ are hydrogen. In aspects, at least two of $R^4$, $R^5$, and $R^6$ are hydrogen. For the substituents in the compound of Formula (IIa) one or more of the following provisos may optionally apply: (i) $R^1$, $R^2$, $R^4$, $R^5$, and $R^6$ are not all hydrogen; (ii) $R^5$ is not —$NHCH_3$ when $R^1$, $R^2$, $R^3$, $R^4$, and $R^6$ are hydrogen; (iii) $R^5$ is not —$NH_2$ when $R^1$, $R^2$, $R^3$, $R^4$, and $R^6$ are hydrogen; and (iv) $R^1$ is not methyl when $R^2$, $R^3$, $R^4$, $R^5$, and $R^6$ are hydrogen.

In embodiments, the compound of Formula (II) is a compound of Formula (IIb) or a pharmaceutically acceptable salt thereof:

(IIb)

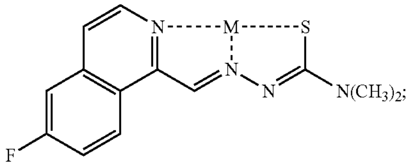

wherein M is a metal or metal salt. In aspects, M is copper, a copper salt, zinc, a zinc salt, cobalt, a cobalt salt, nickel, a nickel salt, magnesium, a magnesium salt, iron, an iron salt, manganese, a manganese salt, gallium, a gallium salt, germanium, a germanium salt, calcium, or a calcium salt. In aspects, M is copper, copper bromide, copper fluoride, copper iodide, copper nitrate, copper perchlorate, copper sulfate, copper acetate, or copper tartrate. In aspects, M is copper. In aspects, M is a copper salt. In aspects, M is copper chloride, copper bromide, copper fluoride, copper iodide, copper nitrate, copper perchlorate, copper sulfate, copper acetate, or copper tartrate. In aspects, M is copper chloride.

In embodiments, the compound of Formula (II) is HCT16 (or Cu[HCT-13]) or a pharmaceutically acceptable salt thereof:

(HCT16)

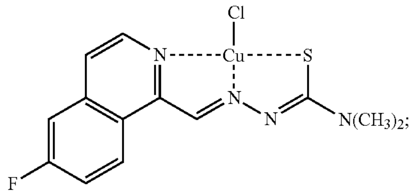

Pharmaceutical Compositions

Provided herein are pharmaceutical compositions comprising a compound described herein and a pharmaceutically acceptable excipient. The provided compositions are suitable for formulation and administration in vitro or in vivo. Suitable carriers and excipients and their formulations are described in Remington: The Science and Practice of Pharmacy, 21st Edition, David B. Troy, ed., Lippicott Williams & Wilkins (2005).

In embodiments, the disclosure provides pharmaceutical compositions comprising the compounds described herein and a pharmaceutically acceptable excipient. In aspects, the pharmaceutical composition comprises a compound of Formula (I) and a pharmaceutically acceptable excipient. In aspects, the pharmaceutical composition comprises a pharmaceutically acceptable salt of compound of Formula (I) and a pharmaceutically acceptable excipient. In aspects, the pharmaceutical composition comprises a metal complex of a compound of Formula (I) and a pharmaceutically acceptable excipient. In aspects, the pharmaceutical composition comprises a pharmaceutically acceptable salt of a metal complex of a compound of Formula (I) and a pharmaceutically acceptable excipient. In aspects, the pharmaceutical composition comprises a compound of Formula (Ia) and a pharmaceutically acceptable excipient. In aspects, the pharmaceutical composition comprises a pharmaceutically acceptable salt of compound of Formula (Ia) and a pharmaceutically acceptable excipient. In aspects, the pharmaceutical composition comprises a metal complex of a compound of Formula (Ia) and a pharmaceutically acceptable excipient. In aspects, the pharmaceutical composition comprises a pharmaceutically acceptable salt of a metal complex of a compound of Formula (Ia) and a pharmaceutically acceptable excipient. In aspects, the pharmaceutical composition comprises a compound of Formula (II) and a pharmaceutically acceptable excipient. In aspects, the pharmaceutical composition comprises a pharmaceutically acceptable salt of compound of Formula (II) and a pharmaceutically acceptable excipient. In aspects, the pharmaceutical composition comprises a compound of Formula (IIa) and a pharmaceutically acceptable excipient. In aspects, the pharmaceutical composition comprises a pharmaceutically acceptable salt of compound of Formula (IIa) and a pharmaceutically acceptable excipient. In aspects, the pharmaceutical composition comprises HCT2 and a pharmaceutically acceptable excipient. In aspects, the pharmaceutical composition comprises a pharmaceutically acceptable salt of HCT2 and a pharmaceutically acceptable excipient. In aspects, the pharmaceutical composition comprises HCT3 and a pharmaceutically acceptable excipient. In aspects, the pharmaceutical composition comprises a pharmaceutically acceptable salt of HCT3 and a pharmaceutically acceptable excipient. In aspects, the pharmaceutical composition comprises HCT7 and a pharmaceutically acceptable excipient. In aspects, the pharmaceutical composition comprises a pharmaceutically acceptable salt of HCT7 and a pharmaceutically acceptable excipient. In aspects, the pharmaceutical composition comprises HCT8 and a pharmaceutically acceptable excipient. In aspects, the pharmaceutical composition comprises a pharmaceutically acceptable salt of HCT8 and a pharmaceutically acceptable excipient. In aspects, the pharmaceutical composition comprises HCT9 and a pharmaceutically acceptable excipient. In aspects, the pharmaceutical composition comprises a pharmaceutically acceptable salt of HCT9 and a pharmaceutically acceptable excipient. In aspects, the pharmaceutical composition comprises HCT10 and a pharmaceutically acceptable excipient. In aspects, the pharmaceutical composition comprises a pharmaceutically acceptable salt of HCT10 and a pharmaceutically acceptable excipient. In aspects, the pharmaceutical composition comprises HCT11 and a pharmaceutically acceptable excipient. In aspects, the pharmaceutical composition comprises a pharmaceutically acceptable salt of HCT11 and a pharmaceutically acceptable excipient. In aspects, the pharmaceutical composition comprises HCT12 and a pharmaceutically acceptable excipient. In aspects, the pharmaceutical composition comprises a pharmaceutically acceptable salt of HCT12 and a pharmaceutically acceptable excipient. In aspects, the pharmaceutical composition comprises HCT13 and a pharmaceutically acceptable excipient. In aspects, the pharmaceutical composition comprises a pharmaceutically acceptable salt of HCT13 and a pharmaceutically acceptable excipient. In aspects, the pharmaceutical composition comprises HCT14 and a pharmaceutically acceptable excipient. In aspects, the pharmaceutical composition comprises a pharmaceutically acceptable salt of HCT14 and a pharmaceutically acceptable excipient. In aspects, the pharmaceutical composition comprises HCT15 and a pharmaceutically acceptable excipient. In aspects, the pharmaceutical composition comprises a pharmaceutically acceptable salt of HCT15 and a pharmaceutically acceptable excipient. In aspects, the pharmaceutical composition comprises HCT16 and a pharmaceutically acceptable excipient. In aspects, the pharmaceutical composition comprises a pharmaceutically acceptable salt of HCT16 and a pharmaceutically acceptable excipient. The pharmaceutically acceptable excipient may be any known in the art as described herein.

The disclosure provides compositions comprising: (i) a compound of Formula (I) and (ii) a metal, a metal salt, or a combination thereof. In aspects, the disclosure provides compositions comprising: (i) a compound of Formula (I); (ii) a metal, a metal salt, or a combination thereof, and (iii) a pharmaceutically acceptable excipient. In aspects, the compositions comprise: (i) a compound of Formula (Ia) and (ii) a metal, a metal salt, or a combination thereof. In aspects, the disclosure provides compositions comprising: (i) a compound of Formula (Ia); (ii) a metal, a metal salt, or a combination thereof; and (iii) a pharmaceutically acceptable excipient. In aspects, the compositions comprise: (i) HCT2 and (ii) a metal, a metal salt, or a combination thereof. In aspects, the disclosure provides compositions comprising: (i) HCT2; (ii) a metal, a metal salt, or a combination thereof; and (iii) a pharmaceutically acceptable excipient. In aspects, the compositions comprise: (i) HCT3 and (ii) a metal, a metal salt, or a combination thereof. In aspects, the disclosure provides compositions comprising: (i) HCT3; (ii) a metal, a metal salt, or a combination thereof; and (iii) a pharmaceutically acceptable excipient. In aspects, the compositions comprise: (i) HCT7 and (ii) a metal, a metal salt, or a combination thereof. In aspects, the disclosure provides compositions comprising: (i) HCT7; (ii) a metal, a metal salt, or a combination thereof; and (iii) a pharmaceutically acceptable excipient. In aspects, the compositions comprise: (i) HCT8 and (ii) a metal, a metal salt, or a combination thereof. In aspects, the disclosure provides compositions comprising: (i) HCT8; (ii) a metal, a metal salt, or a combination thereof; and (iii) a pharmaceutically acceptable excipient. In aspects, the compositions comprise: (i) HCT9 and (ii) a metal, a metal salt, or a combination thereof. In aspects, the disclosure provides compositions comprising: (i) HCT9; (ii) a metal, a metal salt, or a combination thereof; and (iii) a pharmaceutically acceptable excipient. In aspects, the compositions comprise: (i) HCT10 and (ii) a metal, a metal salt, or a combination thereof. In aspects, the disclosure provides compositions comprising: (i) HCT10; (ii) a metal, a metal salt, or a combination thereof, and (iii) a pharmaceutically acceptable excipient. In aspects, the compositions comprise: (i) HCT11 and (ii) a metal, a metal salt, or a combination thereof. In aspects, the disclosure provides compositions comprising: (i) HCT11; (ii) a metal, a metal salt, or a combination thereof, and (iii) a pharmaceutically acceptable excipient. In aspects, the compositions comprise: (i) HCT12 and (ii) a metal, a metal salt, or a combination thereof. In aspects, the disclosure provides compositions comprising: (i) HCT12; (ii) a metal, a metal salt, or a combination thereof, and (iii) a pharmaceutically acceptable excipient. In aspects, the compositions comprise: (i) HCT13 and (ii) a metal, a metal salt, or a combination thereof. In aspects, the disclosure provides compositions comprising: (i) HCT13; (ii) a metal, a metal salt, or a combination thereof, and (iii) a pharmaceutically acceptable excipient. In aspects, the compositions comprise: (i) HCT14 and (ii) a metal, a metal salt, or a combination thereof. In aspects, the disclosure provides compositions comprising: (i) HCT14; (ii) a metal, a metal salt, or a combination thereof, and (iii) a pharmaceutically acceptable excipient. In aspects, the compositions comprise: (i) HCT15 and (ii) a metal, a metal salt, or a combination thereof. In aspects, the disclosure provides compositions comprising: (i) HCT15; (ii) a metal, a metal salt, or a combination thereof, and (iii) a pharmaceutically acceptable excipient. In aspects, component (ii) is a metal. In aspects, component (ii) is a metal selected from the group consisting of copper, zinc, cobalt, nickel, magnesium, iron, manganese, gallium, germanium, calcium, or a combination of two or more thereof. In aspects, component (ii) is copper. In aspects, component (ii) is a metal salt. In aspects, component (ii) is a metal salt selected from the group consisting of a copper salt, a zinc salt, a cobalt salt, a nickel salt, a magnesium salt, an iron salt, a manganese salt, a gallium salt, a germanium salt, a calcium salt, or a combination of two or more thereof. In aspects, component (ii) is a copper salt. In aspects, component (ii) is copper chloride, copper bromide, copper fluoride, copper iodide, copper nitrate, copper perchlorate, copper sulfate, copper acetate, copper tartrate, or a combination of two or more thereof. In aspects, component (ii) is copper chloride. The pharmaceutically acceptable excipient may be any known in the art as described herein.

In aspects, the compositions comprise: (i) compound HCT-13 and (ii) a metal, a metal salt, or a combination thereof. In aspects, the disclosure provides compositions comprising: (i) compound HCT-13; (ii) a metal, a metal salt, or a combination thereof, and (iii) a pharmaceutically acceptable excipient. In aspects, the compositions comprise: (i) compound HCT-13 and (ii) copper. In aspects, the disclosure provides compositions comprising: (i) compound HCT-13; (ii) copper; and (iii) a pharmaceutically acceptable excipient. In aspects, the compositions comprise: (i) compound HCT-13 and (ii) a copper salt. In aspects, the disclosure provides compositions comprising: (i) compound HCT-13; (ii) a copper salt; and (iii) a pharmaceutically acceptable excipient. In aspects, the compositions comprise: (i) compound HCT-13 and (ii) a copper salt selected from the group consisting of copper chloride, copper bromide, copper fluoride, copper iodide, copper nitrate, copper perchlorate, copper sulfate, copper acetate, copper tartrate, and a combination of two or more thereof. In aspects, the disclosure provides compositions comprising: (i) compound HCT-13; (ii) a copper salt selected from the group consisting of copper chloride, copper bromide, copper fluoride, copper iodide, copper nitrate, copper perchlorate, copper sulfate, copper acetate, copper tartrate, and a combination of two or more thereof, and (iii) a pharmaceutically acceptable excipient. In aspects, the compositions comprise: (i) compound HCT-13 and (ii) copper, copper chloride, copper bromide, copper fluoride, copper iodide, copper nitrate, copper perchlorate, copper sulfate, copper acetate, copper tartrate, or a combination of two or more thereof. In aspects, the compositions comprise: (i) compound HCT-13, (ii) copper, copper chloride, copper bromide, copper fluoride, copper iodide, copper nitrate, copper perchlorate, copper sulfate, copper acetate, copper tartrate, or a combination of two or more thereof, and (iii) a pharmaceutically acceptable excipient. In aspects, the compositions comprise: (i) compound HCT-13 and (ii) copper chloride. In aspects, the disclosure provides compositions comprising: (i) compound HCT-13; (ii) copper chloride; and (iii) a pharmaceutically acceptable excipient.

In aspects, the compositions comprise: (i) HCT1 and (ii) a metal, a metal salt, or a combination thereof. In aspects, the disclosure provides compositions comprising: (i) HCT1; (ii) a metal, a metal salt, or a combination thereof, and (iii) a pharmaceutically acceptable excipient. In aspects, the compositions comprise: (i) HCT4 and (ii) a metal, a metal salt, or a combination thereof. In aspects, the disclosure provides compositions comprising: (i) HCT4; (ii) a metal, a metal salt, or a combination thereof, and (iii) a pharmaceutically acceptable excipient. In aspects, the compositions comprise: (i) HCT5 and (ii) a metal, a metal salt, or a combination thereof. In aspects, the disclosure provides compositions comprising: (i) HCT5; (ii) a metal, a metal salt, or a combination thereof, and (iii) a pharmaceutically acceptable excipient. In aspects, the compositions comprise: (i) HCT6 and (ii) a metal, a metal salt, or a combination thereof. In aspects, the disclosure provides compositions comprising: (i) HCT6; (ii) a metal, a metal salt, or a combination thereof, and (iii) a pharmaceutically acceptable excipient. In aspects, component (ii) is a metal. In aspects, component (ii) is a metal selected from the group consisting of copper, zinc, cobalt, nickel, magnesium, iron, manganese, gallium, germanium, calcium, or a combination of two or more thereof. In aspects, component (ii) is copper. In aspects, component (ii) is a metal salt. In aspects, component (ii) is a metal salt selected from the group consisting of a copper salt, a zinc salt, a cobalt salt, a nickel salt, a magnesium salt, an iron salt, a manganese salt, a gallium salt, a germanium salt, a calcium salt, or a combination of two or more thereof. In aspects, component (ii) is a copper salt. In aspects, component (ii) is copper chloride, copper bromide, copper fluoride, copper iodide, copper nitrate, copper perchlorate, copper sulfate, copper acetate, copper tartrate, or a combination of two or more thereof. In aspects, component (ii) is copper chloride. The pharmaceutically acceptable excipient may be any known in the art as described herein.

"Pharmaceutically acceptable excipient" refers to a substance that aids the administration of an active agent to and absorption by a subject and can be included in the compositions of the disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions, alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the disclosure.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In aspects, oral pharmaceutical compositions will comprise an inert diluent or edible carrier, or they may be enclosed in hard or soft shell gelatin capsule, or they may be compressed into tablets, or they may be incorporated directly with the food. For oral therapeutic administration, the active compounds may be incorporated with excipients and used in the form of ingestible tablets, buccal tablets, troches, capsules, elixirs, suspensions, syrups, wafers, and the like. The percentage of the compositions and preparations may, of course, be varied and may conveniently be between about 1 to about 75% of the weight of the unit. The amount of active compounds in such compositions is such that a suitable dosage can be obtained.

For parenteral administration (e.g., intermuscular, subcutaneous, intravenous, etc.) in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion.

Sterile injectable solutions can be prepared by incorporating the active compounds in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Methods of Treating Cancer

In embodiments, the disclosure provides methods of treating cancer in a subject in need thereof by administering to the subject a therapeutically effective amount of any one of the compounds or compositions described herein. The cancer can be any known in the art. In aspects, the disclosure provides methods of treating malignant solid tumors in a subject in need thereof by administering to the subject a therapeutically effective amount of any one of the compounds or compositions described herein. In aspects, the disclosure provides methods of treating sarcomas in a subject in need thereof by administering to the subject a therapeutically effective amount of any one of the compounds or compositions described herein. In aspects, the disclosure provides methods of treating carcinomas in a subject in need thereof by administering to the subject a therapeutically effective amount of any one of the compounds or compositions described herein. In aspects, the disclosure provides methods of treating lymphomas in a subject in need thereof by administering to the subject a therapeutically effective amount of any one of the compounds or compositions described herein. In aspects, the disclosure provides methods of treating small cell lung carcinoma in a subject in need thereof by administering to the subject a therapeutically effective amount of any one of the compounds or compositions described herein. In aspects, the disclosure provides methods of treating pancreatic cancer in a subject in need thereof by administering to the subject a therapeutically effective amount of any one of the compounds or compositions described herein to treat the pancreatic cancer. In aspects, the disclosure provides methods of treating pancreatic ductal adenocarcinoma in a subject in need thereof by administering to the subject a therapeutically effective amount of any one of the compounds or compositions described herein to treat the pancreatic ductal adenocarcinoma. In aspects, the disclosure provides methods of treating prostate cancer in a subject in need thereof by administering to the subject a therapeutically effective amount of any one of the compounds or compositions described herein to treat the prostate cancer. In aspects, the disclosure provides methods of treating leukemia in a subject in need thereof by administering to the subject a therapeutically effective amount of any one of the compounds or compositions described herein to treat the prostate cancer. In aspects, the leukemia is acute myelogenous leukemia, acute lymphoblastic leukemia, T-cell leukemia, and the like. In aspects, the method comprises administering a compound of Formula (I), a pharmaceutically acceptable salt of a compound of Formula (I), a metal complex of a compound of Formula (I), a pharmaceutically acceptable salt of a metal complex of a compound of Formula (I), a pharmaceutical composition of any one of the foregoing, or a composition comprising a compound of Formula (I) and a metal or metal salt. In aspects, the method comprises administering a compound of Formula (Ia), a pharmaceutically acceptable salt of a compound of Formula (Ia), a metal complex of a compound of Formula (Ia), a pharmaceutically acceptable salt of a metal complex of a compound of Formula (Ia), a pharmaceutical composition of any one of the foregoing, or a composition comprising a compound of Formula (Ia) and a metal or metal salt. In aspects, the method comprises administering a compound of Formula (II), or a pharmaceutically acceptable salt of a compound of Formula (II). In aspects, the method comprises administering a compound of Formula (IIa), a pharmaceutically acceptable salt of a compound of Formula (IIa), or a pharmaceutical composition of one of the foregoing. In aspects, the method comprises administering HCT2, a pharmaceutically acceptable salt of HCT2, a metal complex of HCT2, a pharmaceutically acceptable salt of a metal complex of HCT2, a pharmaceutical composition of any one of the foregoing, or a composition comprising HCT2 and a metal or metal salt. In aspects, the method comprises administering HCT3, a pharmaceutically acceptable salt of HCT3, a metal complex of HCT3, a pharmaceutically acceptable salt of a metal complex of HCT3, a pharmaceutical composition of any one of the foregoing, or a composition comprising HCT3 and a metal or metal salt. In aspects, the method comprises administering HCT7, a pharmaceutically acceptable salt of HCT7, a metal complex of HCT7, a pharmaceutically acceptable salt of a metal complex of HCT7, a pharmaceutical composition of any one of the foregoing, or a composition comprising HCT7 and a metal or metal salt. In aspects, the method comprises administering HCT8, a pharmaceutically acceptable salt of HCT8, a metal complex of HCT8, a pharmaceutically acceptable salt of a metal complex of HCT8, a pharmaceutical composition of any one of the foregoing, or a composition comprising HCT8 and a metal or metal salt. In aspects, the method comprises administering HCT9, a pharmaceutically acceptable salt of HCT9, a metal complex of HCT9, a pharmaceutically acceptable salt of a metal complex of HCT9, a pharmaceutical composition of any one of the foregoing, or a composition comprising HCT9 and a metal or metal salt. In aspects, the method comprises administering HCT10, a pharmaceutically acceptable salt of HCT10, a metal complex of HCT10, a pharmaceutically acceptable salt of a metal complex of HCT10, a pharmaceutical composition of any one of the foregoing, or a composition comprising HCT10 and a metal or metal salt. In aspects, the method comprises administering HCT11, a pharmaceutically acceptable salt of HCT11, a metal complex of HCT11, a pharmaceutically acceptable salt of a metal complex of HCT11, a pharmaceutical composition of any one of the foregoing, or a composition comprising HCT11 and a metal or metal salt. In aspects, the method comprises administering HCT12, a pharmaceutically acceptable salt of HCT12, a metal complex of HCT12, a pharmaceutically acceptable salt of a metal complex of HCT12, a pharmaceutical composition of any one of the foregoing, or a composition comprising HCT12 and a metal or metal salt. In aspects, the method comprises administering HCT13, a pharmaceutically acceptable salt of HCT13, a metal complex of HCT13, a pharmaceutically acceptable salt of a metal complex of HCT13, a pharmaceutical composition of any one of the foregoing, or a composition comprising HCT13 and a metal or metal salt. In aspects, the method comprises administering HCT14, a pharmaceutically acceptable salt of HCT14, a metal complex of HCT14, a pharmaceutically acceptable salt of a metal complex of HCT14, a pharmaceutical composition of any one of the foregoing, or a composition comprising HCT14 and a metal or metal salt. In aspects, the method comprises administering HCT15, a pharmaceutically acceptable salt of HCT15, a metal complex of HCT15, a pharmaceutically acceptable salt of a metal complex of HCT15, a pharmaceutical composition of any one of the foregoing, or a composition comprising HCT15 and a metal or metal salt. In aspects, the method comprises administering HCT16 or a pharmaceutically acceptable salt of HCT16, or a pharmaceutical composition of one of the foregoing. In aspects, the methods further comprise administering one or more anti-cancer agents, radiation therapy, or a combination thereof.

In embodiments, the disclosure provides methods of treating cancer in a subject in need thereof by administering to the subject a therapeutically effective amount of any one of the compounds or compositions described herein and a therapeutically effective amount of an ATR kinase inhibitor. The cancer can be any known in the art, and the ATR kinase inhibitor can be any known in the art. In aspects, the disclosure provides methods of treating malignant solid tumors in a subject in need thereof by administering to the subject a therapeutically effective amount of any one of the compounds or compositions described herein and a therapeutically effective amount of an ATR kinase inhibitor. In aspects, the disclosure provides methods of treating sarcomas in a subject in need thereof by administering to the subject a therapeutically effective amount of any one of the compounds or compositions described herein and a therapeutically effective amount of an ATR kinase inhibitor. In aspects, the disclosure provides methods of treating carcinomas in a subject in need thereof by administering to the subject a therapeutically effective amount of any one of the compounds or compositions described herein and a therapeutically effective amount of an ATR kinase inhibitor. In aspects, the disclosure provides methods of treating lymphomas in a subject in need thereof by administering to the subject a therapeutically effective amount of any one of the compounds or compositions described herein and a therapeutically effective amount of an ATR kinase inhibitor. In aspects, the disclosure provides methods of treating small cell lung carcinoma in a subject in need thereof by administering to the subject a therapeutically effective amount of any one of the compounds or compositions described herein and a therapeutically effective amount of an ATR kinase inhibitor. In aspects, the disclosure provides methods of treating pancreatic cancer in a subject in need thereof by administering to the subject a therapeutically effective amount of any one of the compounds or compositions described herein and a therapeutically effective amount of an ATR kinase inhibitor to treat the pancreatic cancer. In aspects, the disclosure provides methods of treating pancreatic ductal adenocarcinoma in a subject in need thereof by administering to the subject a therapeutically effective amount of any one of the compounds or compositions described herein and a therapeutically effective amount of an ATR kinase inhibitor to treat the pancreatic ductal adenocarcinoma. In aspects, the disclosure provides methods of treating prostate cancer in a subject in need thereof by administering to the subject a therapeutically effective amount of any one of the compounds or compositions described herein and a therapeutically effective amount of an ATR kinase inhibitor to treat the prostate cancer. In aspects, the disclosure provides methods of treating leukemia in a subject in need thereof by administering to the subject a therapeutically effective amount of any one of the compounds or compositions described herein and a therapeutically effective amount of an ATR kinase inhibitor to treat the leukemia. In aspects, the method comprises administering a compound of Formula (I) or (Ia), a pharmaceutically acceptable salt of a compound of Formula (I), a metal complex of a compound of Formula (I) or (Ia), a pharmaceutically acceptable salt of a metal complex of a compound of Formula (I) or (Ia), a pharmaceutical composition of any one of the foregoing, or a composition comprising a compound of Formula (I) or (Ia) and a metal or metal salt. In aspects, the method comprises administering a compound of Formula (II) or (IIa), or a pharmaceutically acceptable salt of a compound of Formula (II) or (IIa). In aspects, the method comprises administering HCT2, HCT3, HCT7, HCT8, HCT9, HCT10, HCT11, HCT12, HCT13, HCT14, HCT15, HCT16, a pharmaceutically acceptable salt of one of the foregoing, a metal complex of one of the foregoing, or a pharmaceutically acceptable salt of a metal complex of one of the foregoing. In aspects, the method comprises administering a pharmaceutical composition comprising HCT2, HCT3, HCT7, HCT8, HCT9, HCT10, HCT11, HCT12, HCT13, HCT14, HCT15, or HCT16, and a pharmaceutically acceptable carrier. In aspects, the method comprises administering a pharmaceutical composition comprising HCT2, HCT3, HCT7, HCT8, HCT9, HCT10, HCT11, HCT12, HCT13, HCT14, HCT15, or HCT16, a metal or metal salt, and optionally a pharmaceutically acceptable carrier. In aspects, the ATR kinase inhibitor is berzosertib, VE-821, VX-970, AZD6738, schisandrin B, NU6027, NVP-BEZ235, AZ20, caffeine, wortmannin, or an analog of any one of the foregoing. In aspects, the ATR kinase inhibitor is berzosertib. In aspects, the methods further comprise administering one or more additional anti-cancer agents, radiation therapy, or a combination thereof.

In embodiments, the disclosure provides methods for treating a cancer in a subject in need thereof by administering to the subject a therapeutically effective amount of any one of the compounds or compositions described herein and a therapeutically effective amount of radiation therapy. In aspects, the radiation therapy is external beam radiation therapy. In aspects, the radiation therapy is brachytherapy. In aspects, the radiation therapy is a combination of external beam radiation therapy and brachytherapy. In aspects, the cancer is a solid tumor cancer, such as a sarcoma, carcinoma, or lymphoma. In aspects, the cancer is small cell lung carcinoma. In aspects, the cancer is pancreatic cancer. In aspects, the cancer is pancreatic ductal adenocarcinoma. In aspects, the cancer is prostate cancer. In aspects, the cancer is leukemia. In aspects, the method comprises administering a compound of Formula (I) or (Ia), a pharmaceutically acceptable salt of a compound of Formula (I), a metal complex of a compound of Formula (I) or (Ia), a pharmaceutically acceptable salt of a metal complex of a compound of Formula (I) or (Ia), a pharmaceutical composition of any one of the foregoing, or a composition comprising a compound of Formula (I) or (Ia) and a metal or metal salt. In aspects, the method comprises administering a compound of Formula (II) or (IIa), or a pharmaceutically acceptable salt of a compound of Formula (II) or (Ha). In aspects, the method comprises administering HCT2, HCT3, HCT7, HCT8, HCT9, HCT10, HCT11, HCT12, HCT13, HCT14, HCT15, HCT16, a pharmaceutically acceptable salt of one of the foregoing, a metal complex of one of the foregoing, or a pharmaceutically acceptable salt of a metal complex of one of the foregoing. In aspects, the method comprises administering a pharmaceutical composition comprising HCT2, HCT3, HCT7, HCT8, HCT9, HCT10, HCT11, HCT12, HCT13, HCT14, HCT15, or HCT16, and a pharmaceutically acceptable carrier. In aspects, the method comprises administering a pharmaceutical composition comprising HCT2, HCT3, HCT7, HCT8, HCT9, HCT10, HCT11, HCT12, HCT13, HCT14, HCT15, or HCT16, a metal or metal salt, and optionally a pharmaceutically acceptable carrier.

In embodiments, the disclosure provides methods for treating a viral infection, a bacterial infection, or a fungal infection in a subject in need thereof by administering to the subject a therapeutically effective amount of any one of the compounds or compositions described herein. In aspects, the method is for treating a viral infection. In aspects, the method is for treating a bacterial infection. In aspects, the method is for treating a fungal infection. In aspects, the methods comprise administering a compound of Formula (I) or (Ia), a pharmaceutically acceptable salt of a compound of Formula (I) or (Ia), a metal complex of a compound of Formula (I) or (Ia), a pharmaceutically acceptable salt of a metal complex of a compound of Formula (I) or (Ia), or a pharmaceutical composition comprising any one of the foregoing. In aspects, the method comprises administering a compound of Formula (II) or (Ha), or a pharmaceutically acceptable salt of a compound of Formula (II) or (IIa). In aspects, the method comprises administering HCT2, HCT3, HCT7, HCT8, HCT9, HCT10, HCT11, HCT12, HCT13, HCT14, HCT15, HCT16, a pharmaceutically acceptable salt of one of the foregoing, a metal complex of one of the foregoing, or a pharmaceutically acceptable salt of a metal complex of one of the foregoing. In aspects, the method comprises administering a pharmaceutical composition comprising HCT2, HCT3, HCT7, HCT8, HCT9, HCT10, HCT11, HCT12, HCT13, HCT14, HCT15, or HCT16, and a pharmaceutically acceptable carrier. In aspects, the method comprises administering a pharmaceutical composition comprising HCT2, HCT3, HCT7, HCT8, HCT9, HCT10, HCT11, HCT12, HCT13, HCT14, HCT15, or HCT16, a metal or metal salt, and optionally a pharmaceutically acceptable carrier.

Dose and Dosing Regimens

The dosage and frequency (single or multiple doses) of the compounds and composition administered to a subject can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer and severity of such symptoms), kind of concurrent treatment, complications from the disease being treated or other health-related problems. Other therapeutic regimens or agents can be used in conjunction with the methods described herein. Adjustment and manipulation of established dosages (e.g., frequency and duration) are well within the ability of those skilled in the art.

For the compounds and composition described herein, the effective amount can be initially determined from cell culture assays. Target concentrations will be those concentrations that are capable of achieving the methods described herein, as measured using the methods described herein or known in the art. As is known in the art, effective amounts for use in humans can also be determined from animal models. For example, a dose for humans can be formulated to achieve a concentration that has been found to be effective in animals. The dosage in humans can be adjusted by monitoring effectiveness and adjusting the dosage upwards or downwards, as described above. Adjusting the dose to achieve maximal efficacy in humans based on the methods described above and other methods is well within the capabilities of the ordinarily skilled artisan.

Dosages of the compounds and composition may be varied depending upon the requirements of the patient. The dose administered to a patient should be sufficient to affect a beneficial therapeutic response in the patient over time. The size of the dose also will be determined by the existence, nature, and extent of any adverse side-effects. Determination of the proper dosage for a particular situation is within the skill of the art. Generally, treatment is initiated with smaller dosages which are less than the optimum dose; thereafter, the dosage is increased by small increments until the optimum effect under circumstances is reached. Dosage amounts and intervals can be adjusted individually to provide levels effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice the compounds and composition by considering factors such as compound potency, relative bioavailability, patient body weight, presence and severity of adverse side effects.

In embodiments, the compounds are administered to a patient at an amount of about 0.1 mg/kg to about 500 mg/kg. In aspects, the compounds are administered to a patient in an amount of about 0.5 mg/kg, 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 200 mg/kg, or 300 mg/kg. It is understood that where the amount is referred to as "mg/kg," the amount is milligram per kilogram body weight of the subject being administered with the compound. In aspects, the compound is administered to a patient in an amount from about 1 mg to about 500 mg per day, as a single dose, or in a dose administered two or three times per day.

EMBODIMENTS 1-59

Embodiment 1. A compound of Formula (I), a pharmaceutically acceptable salt thereof, a metal complex thereof, or a pharmaceutically acceptable salt of a metal complex thereof:

(I)

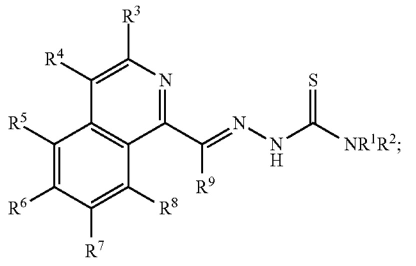

wherein: $R^1$ and $R^2$ are each independently hydrogen, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, a substituted or unsubstituted heteroaryl, or a substituted or unsubstituted alkylarylene; or $R^1$ and $R^2$ together with the nitrogen atom to which they are attached form a substituted or unsubstituted 3 to 6 membered heterocycloalkyl, where the nitrogen is the only heteroatom in the ring; and $R^3$, $R^4$, $R^5$, $R^6$, $R^7$, $R^8$, and $R^9$ are each independently hydrogen or an electronegative moiety; with the provisos that: (i) $R^1$, $R^2$, $R^3$, $R^4$, $R^5$, $R^6$, $R^7$, $R^8$, and $R^9$ are not all hydrogen; (ii) $R^5$ is not —$NHCH_3$ when $R^1$, $R^2$, $R^3$, $R^4$, $R^6$, $R^7$, $R^8$, and $R^9$ are hydrogen; (iii) $R^5$ is not —$NH_2$ when $R^1$, $R^2$, $R^3$, $R^4$, $R^6$, $R^7$, $R^8$, and $R^9$ are hydrogen; and (iv) $R^1$ is not methyl when $R^2$, $R^3$, $R^4$, $R^1$, $R^6$, $R^7$, $R^8$, and $R^9$ are hydrogen.

Embodiment 2. The compound of Embodiment 1, wherein the electronegative moiety is halogen, —$NH_2$, —OH, —$NO_2$, —SH, —CN, —$N_3$, an alkylamine, selenide, a thioether, an aldehyde, a ketone, a carboxylic acid, a carboxylic ester, an amide, an acyl halide, an ether, a thioether, phosphorous, phosphite, phosphate, a phosphonic acid, a phosphonic ester, a phosphonate, sulfonic acid, a sulfonyl, a sulfonamide, a quaternary ammonium amine, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene.

Embodiment 3. The compound of Embodiment 2, wherein the electronegative moiety is halogen, —$NH_2$, or an alkylamine.

Embodiment 4. The compound of Embodiment 1, wherein the compound of Formula (I) is a compound of Formula (Ia), a pharmaceutically acceptable salt thereof, a metal complex thereof, or a pharmaceutically acceptable salt of a metal complex thereof:

(Ia)

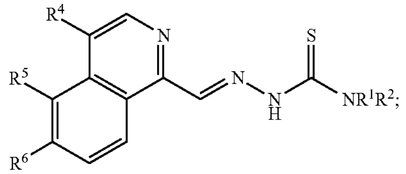

wherein: $R^1$ and $R^2$ are each independently hydrogen or an unsubstituted $C_{1-4}$ alkyl; and $R^4$, $R^5$, and $R^6$ are each independently hydrogen, fluorine, chlorine, bromine, iodine, —$NH_2$, —NH($C_{1-4}$ alkyl), or —N($C_{1-4}$ alkyl)($C_{1-4}$ alkyl); with the provisos that: (i) $R^1$, $R^2$, $R^4$, $R^5$, and $R^6$ are not all hydrogen; (ii) $R^5$ is not —$NHCH_3$ when $R^1$, $R^2$, $R^3$, $R^4$, and $R^6$ are hydrogen; (iii) $R^5$ is not —$NH_2$ when $R^1$, $R^2$, $R^3$, $R^4$, and $R^6$ are hydrogen; and (iv) $R^1$ is not methyl when $R^2$, $R^3$, $R^4$, $R^5$, and $R^6$ are hydrogen.

Embodiment 5. The compound of Embodiment 4, wherein $R^1$ and $R^2$ are each independently hydrogen, —$CH_3$, or —$CH_2CH_3$; and $R^4$, $R^5$, and $R^6$ are each independently hydrogen, fluorine, chlorine, bromine, iodine, —$NH_2$, —$NHCH_3$, —$NHCH_2CH_3$, —$N(CH_3)_2$, —$N(CH_3)(CH_2CH_3)$, or —$N(CH_2CH_3)_2$.

Embodiment 6. The compound of Embodiment 5, wherein $R^1$ and $R^2$ are each independently hydrogen, —$CH_3$, or $CH_2CH_3$; and $R^4$, $R^5$, and $R^6$ are each independently hydrogen, fluorine, $NH_2$, —$NHCH_3$, —$NHCH_2CH_3$, —$N(CH_3)_2$, —$N(CH_3)(CH_2CH_3)$, or —$N(CH_2CH_3)_2$.

Embodiment 7. The compound of Embodiment 4, wherein $R^1$ and $R^2$ are each independently hydrogen, —$CH_3$, or $CH_2CH_3$; $R^4$ and $R^6$ are each independently hydrogen, fluorine, chlorine, bromine, or iodine; and $R^5$ is hydrogen, $NH_2$, —$NHCH_3$, —$NHCH_2CH_3$, —$N(CH_3)_2$, —$N(CH_3)(CH_2CH_3)$, or —$N(CH_2CH_3)_2$.

Embodiment 8. The compound of Embodiment 7, wherein $R^1$ and $R^2$ are each independently hydrogen, —$CH_3$, or $CH_2CH_3$; $R^4$ and $R^6$ are each independently hydrogen or fluorine; and $R^5$ is hydrogen, $NH_2$, —$NHCH_3$, or —$NHCH_2CH_3$.

Embodiment 9. The compound of Embodiment 1 having the structure HCT13.

Embodiment 10. The compound of Embodiment 1 having the structure: HCT2; HCT3; HCT7; HCT8; HCT9; HCT10; HCT11; HCT12; HCT13; HCT14; or HCT15.

Embodiment 11. A pharmaceutical composition comprising the compound of any one of Embodiments 1 to 10 and a pharmaceutically acceptable excipient.

Embodiment 12. A composition comprising: (i) the compound any one of Embodiments 1 to 10, and (ii) copper, a copper salt, zinc, a zinc salt, cobalt, a cobalt salt, nickel, a nickel salt, magnesium, a magnesium salt, iron, an iron salt, manganese, a manganese salt, gallium, a gallium salt, germanium, a germanium salt, calcium, a calcium salt, or a combination of two or more thereof.

Embodiment 13. The composition of Embodiment 12, wherein (ii) is the copper salt.

Embodiment 14. The composition of Embodiment 13, wherein the copper salt is copper chloride, copper bromide, copper fluoride, copper iodide, copper nitrate, copper perchlorate, copper sulfate, copper acetate, or copper tartrate.

Embodiment 15. The composition of Embodiment 14, wherein the copper salt is copper chloride.

Embodiment 16. The composition of Embodiment 12, wherein (ii) is copper.

Embodiment 17. A method of treating cancer in a subject in need thereof, the method comprising administering to the subject a therapeutically effective amount of the compound any one of Embodiments 1 to 10, the pharmaceutical composition of Embodiment 11, or the composition of any one of Embodiments 12 to 16.

Embodiment 18. The method of Embodiment 17, wherein the cancer is pancreatic cancer, prostate cancer, small cell lung carcinoma, or leukemia n.

Embodiment 19. The method of Embodiment 17, wherein the cancer is a solid tumor cancer.

Embodiment 20. The method of Embodiment 17, wherein the cancer is a carcinoma, a sarcoma, or a lymphoma.

Embodiment 21. The method of any one of Embodiments 17 to 20, further comprising administering to the subject a therapeutically effective amount of an anti-cancer agent, radiation therapy, or a combination thereof.

Embodiment 22. The method of Embodiment 21, wherein the anti-cancer agent is ATR kinase inhibitor.

Embodiment 23. The method of Embodiment 22, wherein the ATR kinase inhibitor is berzosertib, VE-821, AZD6738, schisandrin B, NU6027, dactolisib, AZ20, caffeine, or wortmannin.

Embodiment 24. The method of Embodiment 23, wherein the ATR kinase inhibitor is berzosertib.

Embodiment 25. A compound of Formula (II) or a pharmaceutically acceptable salt thereof:

(II)

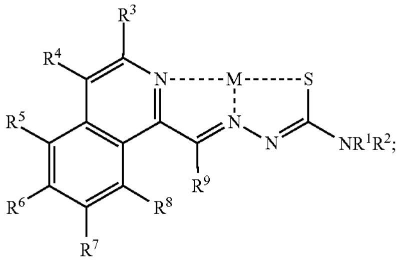

wherein M is a metal or a metal salt; $R^1$ and $R^2$ are each independently a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene; or $R^1$ and $R^2$ together with the nitrogen atom to which they are attached form a substituted or unsubstituted 3 to 6 membered heterocycloalkyl, where the nitrogen is the only heteroatom in the ring; and $R^3$, $R^4$, $R^5$, $R^6$, $R^7$, $R^8$, and $R^9$ are each independently hydrogen or an electronegative moiety.

Embodiment 26. The compound of Embodiment 25, wherein the electronegative moiety is halogen, —$NH_2$, —OH, —$NO_2$, —SH, —CN, —$N_3$, an alkylamine, selenide, a thioether, an aldehyde, a ketone, a carboxylic acid, a carboxylic ester, an amide, an acyl halide, an ether, a thioether, phosphorous, phosphite, phosphate, a phosphonic acid, a phosphonic ester, a phosphonate, sulfonic acid, a sulfonyl, a sulfonamide, a quaternary ammonium amine, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene.

Embodiment 27. The compound of Embodiment 26, wherein the electronegative moiety is halogen, —$NH_2$, or an alkylamine.

Embodiment 28. The compound of any one of Embodiments 25 to 27, wherein M is a metal salt.

Embodiment 29. The compound of Embodiment 28, wherein the metal salt is a copper salt, a zinc salt, a cobalt salt, a nickel salt, a magnesium salt, an iron salt, a manganese salt, a gallium salt, a germanium salt, or a calcium salt.

Embodiment 30. The compound of Embodiment 29, wherein the metal salt is the copper salt.

Embodiment 31. The compound of Embodiment 30, wherein the copper salt is copper chloride, copper bromide, copper fluoride, copper iodide, copper nitrate, copper perchlorate, copper sulfate, copper acetate, or copper tartrate.

Embodiment 32. The compound of Embodiment 31, wherein the copper salt is copper chloride.

Embodiment 33. The compound of any one of Embodiments 25 to 27, wherein M is a metal.

Embodiment 34. The compound of Embodiment 33, wherein the metal is copper, zinc, cobalt, nickel, magnesium, iron, manganese, gallium, germanium, or calcium.

Embodiment 35. The compound of Embodiment 34, wherein the metal is copper.

Embodiment 36. The compound of any one of Embodiments 25 to 35, wherein: (i) $R^1$, $R^2$, $R^3$, $R^4$, $R^5$, $R^6$, $R^7$, $R^8$, and $R^9$ are not concurrently hydrogen; (ii) $R^5$ is not —$NHCH_3$ when $R^1$, $R^2$, $R^3$, $R^4$, $R^6$, $R^7$, $R^8$, and $R^9$ are hydrogen; (iii) $R^5$ is not —$NH_2$ when $R^1$, $R^2$, $R^3$, $R^4$, $R^6$, $R^7$, $R^8$, and $R^9$ are hydrogen; and (iv) $R^1$ is not methyl when $R^2$, $R^3$, $R^4$, $R^5$, $R^6$, $R^7$, $R^8$, and $R^9$ are hydrogen.

Embodiment 37. The compound of Embodiment 25, wherein the compound of Formula (II) is a compound of Formula (IIa) or a pharmaceutically acceptable salt thereof:

(IIa)

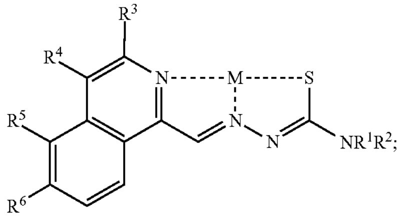

wherein: $R^1$ and $R^2$ are each independently hydrogen or an unsubstituted $C_{1-4}$ alkyl; $R^4$, $R^5$, and R are each independently hydrogen, fluorine, chlorine, bromine, iodine, —$NH_2$, —NH($C_{1-4}$ alkyl), or —N($C_{1-4}$ alkyl)($C_{1-4}$ alkyl); and M is a copper, a copper salt, zinc, a zinc salt, cobalt, a cobalt salt, nickel, a nickel salt, magnesium, a magnesium salt, iron, an iron salt, manganese, a manganese salt, gallium, a gallium salt, germanium, a germanium salt, calcium, or a calcium salt.

Embodiment 38. The compound of Embodiment 37, wherein $R^1$ and $R^2$ are each independently hydrogen, —$CH_3$, or $CH_2CH_3$; and $R^4$, $R^5$, and $R^6$ are each independently hydrogen, fluorine, chlorine, bromine, iodine, —$NH_2$, —$NHCH_3$, —$NHCH_2CH_3$, —$N(CH_3)_2$, —$N(CH_3)(CH_2CH_3)$, or —$N(CH_2CH_3)_2$.

Embodiment 39. The compound of Embodiment 38, wherein $R^1$ and $R^2$ are each independently hydrogen, —$CH_3$, or $CH_2CH_3$; and $R^4$, $R^5$, and $R^6$ are each independently hydrogen, fluorine, $NH_2$, —$NHCH_3$, —$NHCH_2CH_3$, —$N(CH_3)_2$, —$N(CH_3)(CH_2CH_3)$, or —$N(CH_2CH_3)_2$.

Embodiment 40. The compound of Embodiment 37, wherein $R^1$ and $R^2$ are each independently hydrogen, —$CH_3$, or $CH_2CH_3$; $R^4$ and $R^6$ are each independently hydrogen, fluorine, chlorine, bromine, or iodine; and $R^5$ is hydrogen, $NH_2$, —$NHCH_3$, —$NHCH_2CH_3$, —$N(CH_3)_2$, —$N(CH_3)(CH_2CH_3)$, or —$N(CH_2CH_3)_2$.

Embodiment 41. The compound of Embodiment 40, wherein $R^1$ and $R^2$ are each independently hydrogen, —$CH_3$, or $CH_2CH_3$; $R^4$ and $R^6$ are each independently hydrogen or fluorine; and $R^5$ is hydrogen, $NH_2$, —$NHCH_3$, or —$NHCH_2CH_3$.

Embodiment 42. The compound of Embodiment 37, wherein: (i) $R^1$, $R^2$, $R^4$, $R^5$, and $R^6$ are not all hydrogen; (ii) $R^5$ is not —$NHCH_3$ when $R^1$, $R^2$, $R^3$, $R^4$, and $R^6$ are hydrogen; (iii) $R^5$ is not —$NH_2$ when $R^1$, $R^2$, $R^3$, $R^4$, and $R^6$ are hydrogen; and (iv) $R^1$ is not methyl when $R^2$, $R^3$, $R^4$, $R^5$, and $R^6$ are hydrogen.

Embodiment 43. The compound of any one of Embodiments 37 to 42, wherein M is copper.

Embodiment 44. The compound of any one of Embodiments 37 to 42, wherein M is a copper salt.

Embodiment 45. The compound of Embodiment 44, wherein the copper salt is copper chloride, copper bromide, copper fluoride, copper iodide, copper nitrate, copper perchlorate, copper sulfate, copper acetate, or copper tartrate.

Embodiment 46. The compound of Embodiment 45, wherein the copper salt is copper chloride.

Embodiment 47. The compound of any one of Embodiments 37 to 46, wherein $R^1$ and $R^2$ are —$CH_3$; $R^4$ and $R^5$ are hydrogen; and $R^6$ is fluorine.

Embodiment 48. The compound of any one of Embodiments 37 to 46, wherein: (a) $R^1$, $R^2$, $R^5$, and $R^6$ are hydrogen, and $R^4$ is fluorine; (b) $R^1$, $R^2$, $R^4$, and $R^5$ are hydrogen, and $R^6$ is fluorine; (c) $R^1$ is —$CH_3$; $R^2$, $R^5$, and $R^6$ are hydrogen; and $R^4$ is fluorine; (d) $R^1$ is —$CH_3$; $R^2$, $R^4$, and $R^5$ are hydrogen; and $R^6$ is fluorine; (e) $R^1$ is —$CH_3$; $R^2$, $R^4$, and $R^6$ are hydrogen; and $R^5$ is —$NHCH_3$; (f) $R^1$ is —$CH_3$; $R^2$, $R^4$, and $R^6$ are hydrogen; and $R^5$ is —$NH_2$; (g) $R^1$ and $R^2$ are —$CH_3$; $R^4$, $R^5$, and $R^6$ are hydrogen; (h) $R^1$ and $R^2$ are —$CH_3$; $R^4$ is fluorine; and $R^5$ and $R^6$ are hydrogen; (i) $R^1$ and $R^2$ are —$CH_3$; $R^4$ and $R^5$ are hydrogen; and $R^6$ is fluorine; (j) $R^1$ and $R^2$ are —$CH_3$; $R^4$ is hydrogen; $R^5$ is —$NHCH_3$; and $R^6$ is fluorine; or (k) $R^1$ and $R^2$ are —$CH_3$; $R^4$ is fluorine $R^5$ is —$NHCH_3$; and $R^6$ is hydrogen.

Embodiment 49. The compound of Embodiment 37 having the structure:

(IIb)

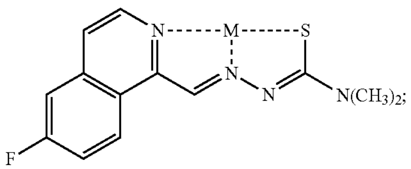

wherein M is copper, copper chloride, copper bromide, copper fluoride, copper iodide, copper nitrate, copper perchlorate, copper sulfate, copper acetate, or copper tartrate.

Embodiment 50. The compound of Embodiment 49 having the structure:

(HCT16)

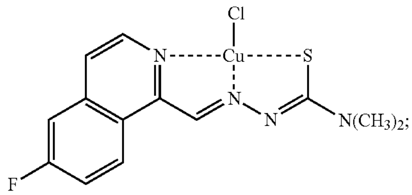

Embodiment 51. A pharmaceutical composition comprising the compound of any one of Embodiments 25 to 50 and a pharmaceutically acceptable excipient.

Embodiment 52. A method of treating cancer in a subject in need thereof, the method comprising administering to the subject a therapeutically effective amount of the compound of any one of Embodiments 25 to 50 or the pharmaceutical composition of Embodiment 51.

Embodiment 53. The method of Embodiment 52, wherein the cancer is pancreatic cancer, prostate cancer, small cell lung carcinoma, or leukemia.

Embodiment 54. The method of Embodiment 52, wherein the cancer is a solid tumor cancer.

Embodiment 55. The method of Embodiment 52, wherein the cancer is a carcinoma, a sarcoma, or a lymphoma.

Embodiment 56. The method of any one of Embodiments 52 to 55, further comprising administering to the subject a therapeutically effective amount of an anti-cancer agent, radiation therapy, or a combination thereof.

Embodiment 57. The method of Embodiment 56, wherein the anti-cancer agent is ATR kinase inhibitor.

Embodiment 58. The method of Embodiment 57, wherein the ATR kinase inhibitor is berzosertib, VE-821, AZD6738, schisandrin B, NU6027, dactolisib, AZ20, caffeine, or wortmannin.

Embodiment 59. The method of Embodiment 58, wherein the ATR kinase inhibitor is berzosertib.

Embodiments P1-P67

Embodiment P1. A compound of Formula (I), a pharmaceutically acceptable salt thereof, a metal complex thereof, or a pharmaceutically acceptable salt of a metal complex thereof:

(I)

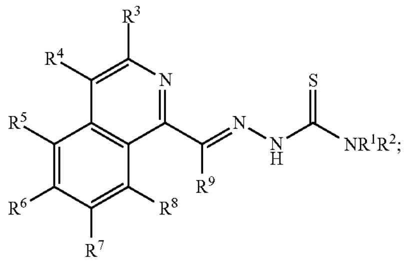

wherein: $R^1$ and $R^2$ are each independently hydrogen, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, a substituted or unsubstituted heteroaryl, or a substituted or unsubstituted alkylarylene; and $R^3$, $R^4$, $R^5$, $R^6$, $R^7$, $R^8$, and $R^9$ are each independently hydrogen or an electronegative moiety; with the provisos that: (i) $R^1$, $R^2$, $R^3$, $R^4$, $R^5$, $R^6$, $R^7$, $R^8$, and $R^9$ are not concurrently hydrogen; (ii) $R^5$ is not —$NHCH_3$ when $R^1$, $R^2$, $R^3$, $R^4$, $R^6$, $R^7$, $R^8$, and $R^9$ are hydrogen; (iii) $R^5$ is not —$NH_2$ when $R^1$, $R^2$, $R^3$, $R^4$, $R^6$, $R^7$, $R^8$, and $R^9$ are hydrogen; and (iv) $R^1$ is not methyl when $R^2$, $R^3$, $R^4$, $R^1$, $R^6$, $R^7$, $R^8$, and $R^9$ are hydrogen.

Embodiment P2. A compound of Formula (II) or a pharmaceutically acceptable salt thereof:

(II)

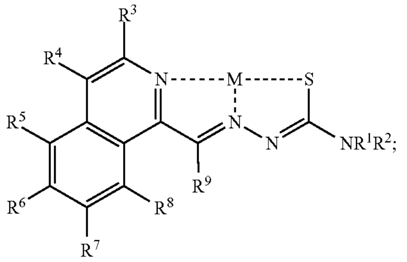

wherein: M is a metal or a metal salt; $R^1$ and $R^2$ are each independently a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene; and $R^3$, $R^4$, $R^5$, $R^6$, $R^7$, $R^8$, and $R^9$ are each independently hydrogen or an electronegative moiety.

Embodiment P3. The compound of embodiment P2, wherein: (i) $R^1$, $R^2$, $R^3$, $R^4$, $R^5$, $R^6$, $R^7$, $R^8$, and $R^9$ are not concurrently hydrogen; (ii) $R^5$ is not —$NHCH_3$ when $R^1$, $R^2$, $R^3$, $R^4$, $R^6$, $R^7$, $R^8$, and $R^9$ are hydrogen; (iii) $R^5$ is not —$NH_2$ when $R^1$, $R^2$, $R^3$, $R^4$, $R^6$, $R^7$, $R^8$, and $R^9$ are hydrogen; and (iv) $R^1$ is not methyl when $R^2$, $R^3$, $R^4$, $R^5$, $R^6$, $R^7$, $R^8$, and $R^9$ are hydrogen.

Embodiment P4. The compound of any one of embodiments P1 to P3, wherein the electronegative moiety is halogen, —$NH_2$, —OH, —$NO_2$, —SH, —CN, —$N_3$, an alkylamine, selenide, a thioether, an aldehyde, a ketone, a carboxylic acid, a carboxylic ester, an amide, an acyl halide, an ether, a thioether, phosphorous, phosphite, phosphate, a phosphonic acid, a phosphonic ester, a phosphonate, sulfonic acid, a sulfonyl, a sulfonamide, a quaternary ammonium amine, a substituted or unsubstituted alkyl, a substituted or unsubstituted heteroalkyl, a substituted or unsubstituted cycloalkyl, a substituted or unsubstituted heterocycloalkyl, a substituted or unsubstituted aryl, or a substituted or unsubstituted heteroaryl, or a substituted or unsubstituted alkylarylene.

Embodiment P5. The compound of embodiment P4, wherein the substituted alkyl is an alkyl substituted with fluorine, chlorine, or bromine.

Embodiment P6. The compound of embodiment P5, wherein the substituted alkyl is —$CF_3$ or —$CF_2CF_3$.

Embodiment P7. The compound of embodiment P4, wherein the sulfonyl is tosyl, nosyl, brosyl, mesyl, or triflyl.

Embodiment P8. The compound of embodiment P4, wherein the electronegative moiety is halogen.

Embodiment P9. The compound of embodiment P8, wherein the halogen is chlorine, fluorine, or bromine.

Embodiment P10. The compound of embodiment P9, wherein the halogen is fluorine.

Embodiment P11. The compound of embodiment P1 having the structure of (HCT2).

Embodiment P12. The compound of embodiment P1 having the structure of (HCT3).

Embodiment P13. The compound of embodiment P1 having the structure of (HCT7).

Embodiment P14. The compound of embodiment P1 having the structure of (HCT8).

Embodiment P15. The compound of embodiment P1 having the structure of (HCT9).

Embodiment P16. The compound of embodiment P1 having the structure of (HCT10).

Embodiment P17. The compound of embodiment P1 having the structure of (HCT11).

Embodiment P18. The compound of embodiment P1 having the structure of (HCT12).

Embodiment P19. The compound of embodiment P1 having the structure of (HCT13).

Embodiment 2P0. The compound of embodiment P1 having the structure of (HCT14).

Embodiment P21. The compound of embodiment P1 having the structure of (HCT15).

Embodiment P22. The compound of any one of embodiments P2 to P10, wherein M is a metal salt.

Embodiment P23. The compound of embodiment P22, wherein the metal salt is a copper salt, a zinc salt, a cobalt salt, a nickel salt, a magnesium salt, an iron salt, a manganese salt, a gallium salt, a germanium salt, or a calcium salt.

Embodiment P24. The compound of embodiment P23, wherein the metal salt is the copper salt.

Embodiment P25. The compound of embodiment P24, wherein the copper salt is copper chloride, copper bromide, copper fluoride, copper iodide, copper nitrate, copper perchlorate, copper sulfate, copper acetate, or copper tartrate.

Embodiment P26. The compound of embodiment P25, wherein the copper salt is copper chloride.

Embodiment P27. The compound of any one of embodiments P2 to P10, wherein M is a metal.

Embodiment P28. The compound of embodiment P27, wherein the metal is copper, zinc, cobalt, nickel, magnesium, iron, manganese, gallium, germanium, or calcium.

Embodiment P29. The compound of embodiment P28, wherein the metal is copper.

Embodiment P30. The compound of any one of embodiments P22 to P29, wherein $R^1$, $R^2$, $R^3$, $R^5$, $R^6$, $R^7$, $R^8$, and $R^9$ are hydrogen, and $R^4$ is fluorine.

Embodiment P31. The compound of any one of embodiments P22 to P29, wherein $R^1$, $R^2$, $R^3$, $R^4$, $R^5$, $R^7$, $R^8$, and $R^9$ are hydrogen, and $R^6$ is fluorine.

Embodiment P32. The compound of any one of embodiments P22 to P29, wherein $R^1$ is —$CH_3$; $R^2$, $R^3$, $R^5$, $R^6$, $R^7$, $R^8$, and $R^9$ are hydrogen; and $R^4$ is fluorine.

Embodiment P33. The compound of any one of embodiments P22 to P29, wherein $R^1$ is —$CH_3$; $R^2$, $R^3$, $R^4$, $R^5$, $R^7$, $R^8$, and $R^9$ are hydrogen; and $R^6$ is fluorine.

Embodiment P34. The compound of any one of embodiments P22 to P29, wherein $R^1$ is —$CH_3$; $R^2$, $R^3$, $R^4$, $R^6$, $R^7$, $R^8$, and $R^9$ are hydrogen; and $R^5$ is —$NHCH_3$.

Embodiment P35. The compound of any one of embodiments P22 to P29, wherein $R^1$ is —$CH_3$; $R^2$, $R^3$, $R^4$, $R^6$, $R^7$, $R^8$, and $R^9$ are hydrogen; and $R^5$ is —$NH_2$.

Embodiment P36. The compound of any one of embodiments P22 to P29, wherein $R^1$ and $R^2$ are —$CH_3$; $R^3$, $R^4$, $R^5$, $R^6$, $R^7$, $R^8$, and $R^9$ are hydrogen.

Embodiment P37. The compound of any one of embodiments P22 to P29, wherein $R^1$ and $R^2$ are —$CH_3$; $R^3$, $R^5$, $R^6$, $R^7$, $R^8$, and $R^9$ are hydrogen; and $R^4$ is fluorine.

Embodiment P38. The compound of any one of embodiments P22 to P29, wherein $R^1$ and $R^2$ are —$CH_3$; $R^3$, $R^4$, $R^5$, $R^7$, $R^8$, and $R^9$ are hydrogen; and $R^6$ is fluorine.

Embodiment P39. The compound of any one of embodiments P22 to P29, wherein $R^1$ and $R^2$ are —$CH_3$; $R^3$, $R^4$, $R^7$, $R^8$, and $R^9$ are hydrogen; $R^5$ is —$NHCH_3$; and $R^6$ is fluorine.

Embodiment P40. The compound of any one of embodiments P22 to P29, wherein $R^1$ and $R^2$ are —$CH_3$; $R^3$, $R^6$, $R^7$, $R^8$, and $R^9$ are hydrogen; $R^5$ is —$NHCH_3$; and $R^4$ is fluorine.

Embodiment P41. The compound of embodiment P2 having the structure of (HCT16).

Embodiment P42. The compound of any one of embodiments P1 to P18, wherein $R^1$ and $R^2$ are each independently hydrogen or substituted or unsubstituted alkyl; $R^3$ is hydrogen; $R^4$, $R^5$, and $R^6$ are each independently hydrogen or the electronegative moiety; and $R^7$, $R^8$, and $R^9$ are hydrogen.

Embodiment P43. The compound of embodiment P42, wherein the electronegative moiety is halogen.

Embodiment P44. The compound of embodiment P43, wherein the halogen is chlorine, fluorine, or bromine.

Embodiment P45. The compound of embodiment P44, wherein the halogen is fluorine.

Embodiment P46. The compound of embodiment P42, wherein $R^1$ and $R^2$ are each independently hydrogen or an unsubstituted $C_1$-$C_4$ alkyl; $R^3$ is hydrogen; $R^4$ is hydrogen or halogen; $R^5$ is hydrogen, halogen, —$NH_2$, or the alkylamine; $R^6$ is hydrogen or halogen; and $R^7$, $R^8$, and $R^9$ are hydrogen.

Embodiment P47. The compound of embodiment P46, wherein $R^4$ is hydrogen and $R^6$ is halogen; $R^4$ is halogen and $R^6$ is hydrogen; or $R^4$ is halogen and $R^6$ is halogen.

Embodiment P48. The compound of embodiment P47, wherein the halogen is chlorine, fluorine, or bromine.

Embodiment P49. The compound of embodiment P48, wherein the halogen is fluorine.

Embodiment P50. The compound of any one of embodiments P42 to P49, wherein $R^5$ is hydrogen, —$NH_2$, —NH($C_1$-$C_4$ alkyl), or —N($C_1$-$C_4$ alkyl)($C_1$-$C_4$ alkyl).

Embodiment P51. The compound of embodiment P50, wherein $R^5$ is hydrogen.

Embodiment P52. The compound of embodiment P50, wherein $R^5$ is —$NH_2$, —$NHCH_3$, —$NH(CH_2CH_3)$, or —N($C_1$-$C_2$ alkyl)($C_1$-$C_2$ alkyl).

Embodiment P53. The compound of embodiment P52, wherein $R^5$ is —$NH_2$.

Embodiment P54. The compound of embodiment P52, wherein $R^5$ is —$NHCH_3$.

Embodiment P55. A pharmaceutical composition including the compound of any one of embodiments P1 to P54 and a pharmaceutically acceptable excipient.

Embodiment P56. A method of treating cancer in a subject in need thereof, the method including administering to the subject a therapeutically effective amount of the compound of any one of embodiments P1 to P54 or the pharmaceutical composition of embodiment P55.

Embodiment P57. The method of embodiment P56, wherein the cancer is a solid tumor cancer.

Embodiment 5P8. The method of embodiment 5P7, wherein the solid tumor cancer is a carcinoma, a sarcoma, or a lymphoma.

Embodiment P59. The method of embodiment P56, wherein the cancer is pancreatic cancer.

Embodiment P60. The method of embodiment P59, wherein the pancreatic cancer is pancreatic ductal adenocarcinoma.

Embodiment P61. The method of embodiment P56, wherein the cancer is prostate cancer.

Embodiment P62. The method of embodiment P56, wherein the cancer is a small cell lung carcinoma.

Embodiment P63. The method of any one of embodiments P56 to P62, further including administering a therapeutically effective amount of an ATR kinase inhibitor.

Embodiment P64. The method of embodiment P63, wherein the ATR kinase inhibitor is berzosertib, VE-821, AZD6738, schisandrin B, NU6027, dactolisib, AZ20, caffeine, wortmannin, or an analog of any one of the foregoing.

Embodiment P65. The method of embodiment P64, wherein the ATR kinase inhibitor is berzosertib.

Embodiment P66. The method of any one of embodiments P56 to P65, further including administering a therapeutically effective amount of an anti-cancer agent that is not an ATR kinase inhibitor.

Embodiment P67. The method of any one of embodiments P56 to P66, further including administering a therapeutically effective amount of radiation therapy.

EXAMPLES

The following examples are for purposes of illustration and are not intended to limit the spirit or scope of the disclosure or claims.

The inventors produced a series of novel HCTs, which showed antiproliferative activity following methylation and fluorination. Specifically, the inventors showed that the potency of compounds methylated at the 4' amine (6, 9, 11) against Mia PaCa-2 pancreatic cancer cells is significantly increased upon supplementation with $CuCl_2$. The inventors also demonstrated that combining 4' amine methylation with fluorination of the 4- or 6-positions of the isoquinoline ring leads to low-nM antiproliferative activity when used as lone agents, and sub-nM activity when supplemented with copper (HCT12-HCT15). This potent combination of methylation and fluorination was demonstrated, for example, by HCT13, which was nearly 250-fold more active than its non-fluorinated analog HCT11. When supplemented with copper, HCT13 had an $IC_{90}$ of 111 nM, an activity that was matched in the absence of copper supplementation by HCT16, a 1:1 copper-HCT13 complex that was synthesized prior to cell treatment.

The synergistic effects of combining 4' amine methylation with isoquinoline substitution identified HCT-13 as a highly potent antiproliferative agent. The presence of physiologically-relevant levels of Cu(II) greatly potentiated our lead compound's activity, and its mechanism of action revealed it as a copper ionophore. Furthermore, HCT-13 induces ROS production and mitochondrial dysfunction, decreases guanosine nucleotide pools, engages DDR/RSR pathways and synergizes with ATR inhibition, possesses mitochondrial-dependent cytotoxicity, and targets high-OXPHOS cells. Lastly, a one-to-one copper:HCT-13 (Cu[HCT13]) complex was demonstrated to be efficacious in preclinical models of aggressive leukemias.

Example 1

In the synthetic planning, the inventors focused on two modifications of the IQ-1 (HCT1) scaffold: fluorination of the isoquinoline ring, and sequential methylation of the 4' amine. Though the 5-, 7-, and 8-fluoro-substituted analogs of HCT1 were previously reported, and while it was apparent that fluorine placement could influence a compound's toxicity and produce differential antiproliferative effects upon various cell lines, no trends emerged regarding the effects of fluorine placement. (Ref 5). The inventors therefore sought to synthesize the novel 4- and 6-fluoro analogs and investigate the effects sequential 4' amine methylation had upon antiproliferative activity. Several factors support methylation of the 4' amine. It has been reported that dialkylation of the 4' amine of 3-AP led to increased cytotoxicity (Ref. 34), and the addition of methyl groups may improve cell permeability by reducing polarity. The inventors also envisioned that these substitutions could affect metal binding properties by increasing electron density at the sulfur, theoretically improving metal binding ability and increasing RNR inhibition.

Figure 7:
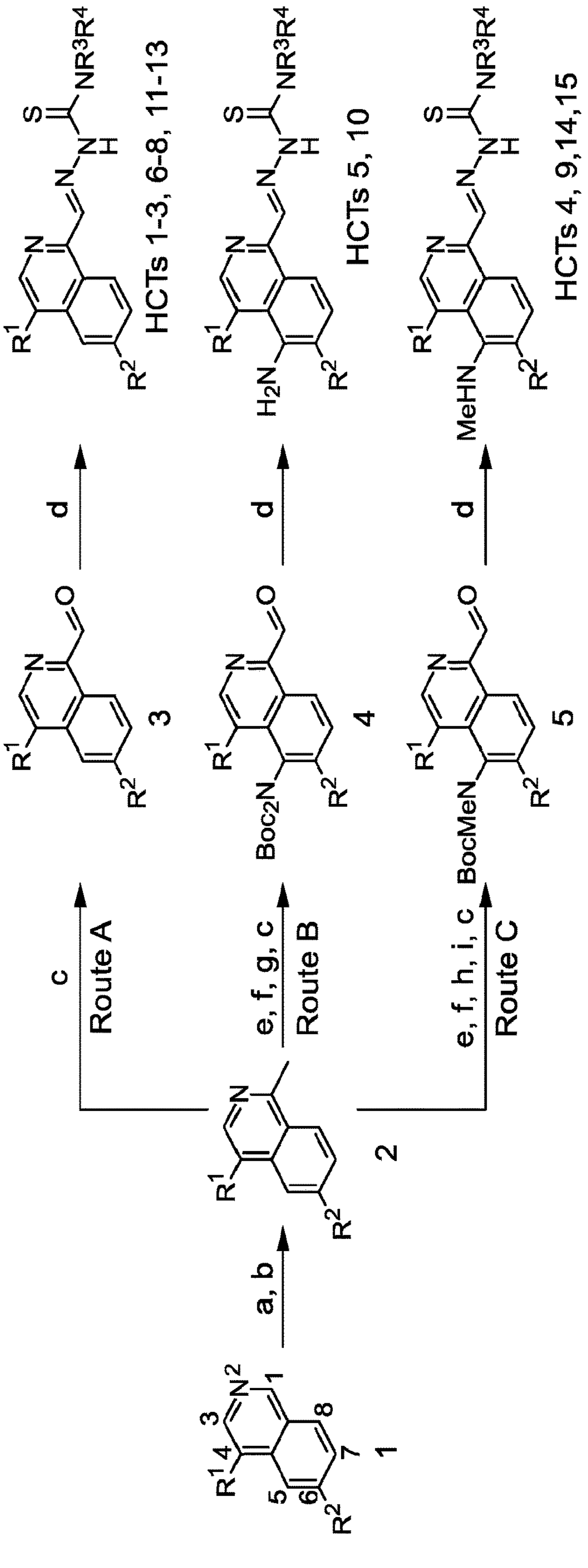
FIG. 7 shows synthetic Routes A, B, and C for preparing the HCT compounds.

In addition to 4 previously reported HCTs (HCT1, HCT4, HCT5, HCT6), a total of 11 novel compounds were synthesized in search of more potent antiproliferative isoquinoline HCTs for application towards cancer therapy, as shown by Synthetic Routes A-C. With reference to FIG. 7, the synthetic schemes for Routes A-C are as follows: (a) allyl chloroformate, MeMgBr, THF; (b) $Pd(PPh_3)_4$, morpholine, DDQ, $CH_2Cl_2$; (c) selenium dioxide, 1,4-dioxane; (d) appropriate thiosemicarbazole, HCl, EtOH, reflux or microwave 50° C.; (e) $KNO_3$, $H_2SO_4$; (f) Fe, HCl, MeOH, reflux; (g) $Boc_2O$, DMAP, TEA, THF; (h) $Boc_2O$, DMAP, TEA, THF; $NaHCO_3$, MeOH, reflux or $K_2CO_3$, MeOH, reflux; (i) NaH, THF; MeI.

HCT1, HCT2, HCT3, HCT6, HCT7, HCT8, HCT11, HCT12, and HCT13 were synthesized through Route A. HCT5 and HCT10 were synthesized through Route B. HCT4, HCT9, HCT14, and HCT15 synthesized through Route C. The substituents for the compounds shown in the Synthetic Schemes are presented in Table 1. Synthetic Routes A, B, and C are set forth in FIG. 7, where $R^1$-$R^5$ refer to the substitutents in the compounds of Formula (I) and Formula (II) described herein.

TABLE 1

| Compound Number | $R^1$ | $R^2$ | $R^3$ | $R^4$ | $R^5$ |
|---|---|---|---|---|---|
| HCT1 | H | H | H | H | H |
| HCT2 | F | H | H | H | H |
| HCT3 | H | F | H | H | H |
| HCT4 | H | H | H | H | $NHCH_3$ |
| HCT5 | H | H | H | H | $NH_2$ |
| HCT6 | H | H | $CH_3$ | H | H |
| HCT7 | F | H | $CH_3$ | H | H |
| HCT8 | H | F | $CH_3$ | H | H |
| HCT9 | H | H | $CH_3$ | H | $NH_2$ |
| HCT10 | H | H | $CH_3$ | H | $NHCH_3$ |
| HCT11 | H | H | $CH_3$ | $CH_3$ | H |
| HCT12 | F | H | $CH_3$ | $CH_3$ | H |
| HCT13 | H | F | $CH_3$ | $CH_3$ | H |
| HCT14 | H | F | $CH_3$ | $CH_3$ | $NHCH_3$ |
| HCT15 | F | H | $CH_3$ | $CH_3$ | $NHCH_3$ |

The synthetic approach began with methylation of the appropriate isoquinoline 1 to generate compound 2. Depending upon the desired 5-position substituent, compound 2 was then subjected to either Route A (5-hydrido), Route B (5-amino), or Route C (5-methylamino). Syntheses of HCTs 1-3, HCTs 6-8, and HCTs 11-13 were carried out by Route A, wherein the methyl substituent of compound 2 was oxidized using selenium dioxide ($SeO_2$) to furnish the carboxaldehyde compound 3. Condensation with the appropriate thiosemicarbazide under acidic conditions yielded the desired HCT. HCT5 and HCT10 were synthesized via Route B, which began with nitration of compound 2 followed by an iron-mediated reduction to the amine, which was subsequently Boc-protected and oxidized to produce carboxaldehyde compound 4. This intermediate was then simultaneously Boc-deprotected and condensed with the appropriate thiosemicarbazide under acidic conditions to furnish the target HCT. Syntheses of HCT4, HCT9, HCT14, and HCT15 via Route C proceeded from compound 2 with installation of a nitro group, subsequent conversion to the mono-Boc-methylamine, and $SeO_2$-mediated oxidation to furnish compound 5. Concurrent Boc-deprotection and thiosemicarbazide condensation were again achieved under acidic conditions to provide the desired HCT compound. While characterizing the HCTs, the inventors occasionally observed the presence of a minor Z-isomeric product, particularly for HCTs 11-15. This isomer arose from an intramolecular hydrogen bond between the 2' amine of the thiosemicarbazone and the heterocyclic isoquinoline nitrogen, forming a stable 6-membered hydrogen bonded species. (Ref 40). The E and Z isomers were inseparable by HPLC purification and were used as a mixture in vitro, as previous studies reported no significant difference in potency. (Ref 40).

$IC_{90}$ values against MIAPACA2 cells was first determined in normal cell culture conditions (DMEM media and 10% FBS). Compounds were separated into three series (4' primary amines, 4' secondary amines, 4' tertiary amines) to reflect the relative degrees of 4' amine methylation. A series of non-methylated 4' primary amine compounds were synthesized, with known compounds HCT1, HCT4, and HCT5 to gauge whether fluorination of the isoquinoline proved beneficial for biological activity. (Refs 41, 42). Within the 4' primary amine series, fluorination at the isoquinoline 4-position (HCT2) did not show an increase in potency relative to unsubstituted analog HCT1. However, fluorination at the 6-position (HCT3) showed a 3-fold increase in potency, demonstrating that the fluorine position impacts the potency of these compounds.

In the 4' secondary amine series, a synergistic effect was observed when combining isoquinoline fluorination with 4' amine methylation. The 4-fluorine substituted HCT7 and the 6-fluorine substituted HCT8 were each significantly more potent than their non-fluorinated analog HCT6, as well more potent than their 4' primary amine analogs (HCT2 and HCT3, respectively). The trend of isoquinoline substitution and 4' secondary amine combining to enhance potency held for 5-methylamino substituted HCT9 and 5-amino substituted HCT10. Taken together, these results demonstrated that combining isoquinoline substitution, particularly 4- or 6-fluorination, with 4' amine methylation produced greater-than-additive (i.e., synergistic) antiproliferative effects when compared with either modification alone.

The effects of fluorine substitution became significantly more pronounced for the di-methylated 4'-tertiary amine compounds HCT12 and HCT13, whose $IC_{90}$ values were in the nM range and were roughly 110- and 270-fold more potent, respectively, when compared to their non-fluorinated analog HCT11. Although both analogs were potent, fluorination at the 6-position (HCT13) was found to be a superior modification when compared to fluorination at the 4-position (HCT12), a trend which also held for the fluorine-substituted 5-methylamino compounds HCT14 and HCT15.

Example 2

HCT compounds are known to be copper chelators. (Ref. 32). To test whether the compounds described herein were similarly potentiated, the $IC_{90}$ (+Cu $IC_{90}$) values were determined against MIAPACA2 cells in media supplemented with physiologically relevant levels of copper (DMEM media+10% FBS+20 μM $CuCl_2$). MIAPACA2 cells were treated with the indicated HCT±20 μM Cu(II) for 72 hours, then cell viability was measured with CellTiter-Glo to determine $IC_{90}$ values. The results are shown in Table 2.

TABLE 2

| Compound No. | Amine Type | $IC_{90}$ (nM) | +Cu(II) $IC_{90}$ (nM) |
|---|---|---|---|
| HCT1 (IQ-1) | 4' Primary | 18100 | 2210 |
| HCT2 | 4' Primary | 24600 | 2060 |
| HCT3 | 4' Primary | 5440 | 2040 |
| HCT4 | 4' Primary | 11500 | 5330 |
| HCT5 | 4' Primary | 40500 | 71100 |
| HCT6 | 4' Secondary | 18700 | 331 |
| HCT7 | 4' Secondary | 2080 | 114 |
| HCT8 | 4' Secondary | 4080 | 233 |
| HCT9 | 4' Secondary | 4240 | 607 |
| HCT10 | 4' Secondary | 11200 | 7870 |
| HCT11 | 4' Tertiary | 29600 | 73.7 |
| HCT12 | 4' Tertiary | 274 | 26.6 |
| HCT13 | 4' Tertiary | 111 | 21.6 |
| HCT14 | 4' Tertiary | 272 | 38.4 |
| HCT15 | 4' Tertiary | 327 | 42.3 |

While the activity of HCT-5 was attenuated, all other compounds displayed a significant increase in potency under copper-supplemented conditions. For non-fluorinated isoquinoline compounds HCT1, HCT6, and HCT11, the +Cu $IC_{90}$ values improved as the degree of methylation at the 4' amine increased (10-fold, 60-fold, and 400-fold increase in potency, respectively, versus non-copper-supplemented $IC_{90}$ values). Copper supplementation was similarly beneficial for fluorinated isoquinolines, where all such compounds displayed significant improvements in antiproliferative potency in presence of copper, and fluorine substitution led to greater potency when compared with corresponding non-fluorinated analogs. Compounds bearing 4' tertiary amines were the most active, achieving +Cu $IC_{90}$ values as low as 21.6 nM (HCT13). These results demonstrated that physiologically relevant levels of copper potentiated the activity of isoquinoline HCTs, and that 4' amine methylation synergized with fluorine substitution.

Example 3

Serum copper levels are elevated (>20 μM) in individuals with solid tumor types such as pancreatic ductal adenocarcinoma (PDAC), small cell lung carcinoma (SCLC), and prostate cancer (PC). (Refs. 43-48). These cancers rely upon elevated copper levels to sustain growth, making this transition metal a viable target for therapeutic modulation. (Ref 34). In a panel of PDAC, SCLC, and PC cancer models cultured in media supplemented with physiologically relevant levels of copper (20 μM $CuCl_2$), HCT13 was a highly potent growth inhibitor, with +Cu $IC_{90}$ values ranging from 1 nM to 200 nM (FIG. 1A). In the leukemia cancer model, the cells were treated with HCT-16, as free copper is known to be toxic towards leukemia cells, where the antiproliferative activity of HCT-16 was consistent with that of HCT-13+Cu(II). In this assay, HCT-13 was a highly potent cancer cell growth inhibitor, with IC90 values ranging from 1 nM to 200 nM (FIG. 1A). The normal human epithelial cell line HPDE was markedly more resistant to treatment that the cancer models evaluated (FIG. 1A). Together these results indicate that HCT-13 possess a high degree of cancer-specific cytotoxicity.

Figure 1B:
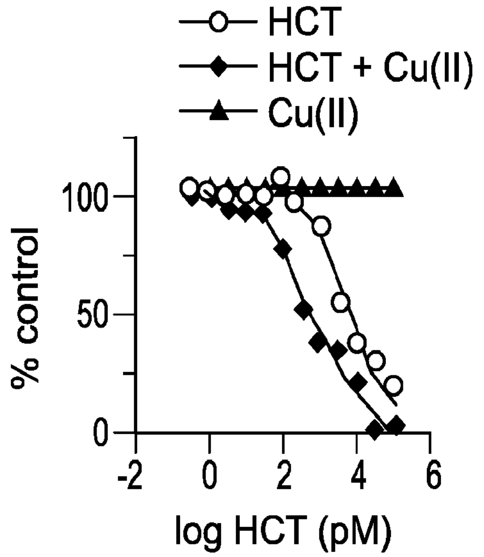
FIG. 1B: proliferation rate of MIAPACA2 PDAC cells measured by CellTiterGlo following HCT-13 treatment for 72h±Cu(II)(20 μM) (and with Cu(II) alone.
Figure 1C:
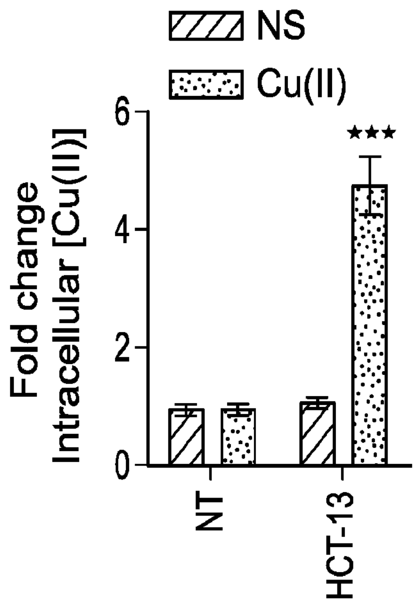
FIG. 1C: intracellular concentrations of copper measured by inductively coupled plasma mass spectrometry (ICP-MS) in MIAPACA2 PDAC cells treated with HCT13 (25 nM) for 24h±Cu(II) (20 μM).
Figure 1D:
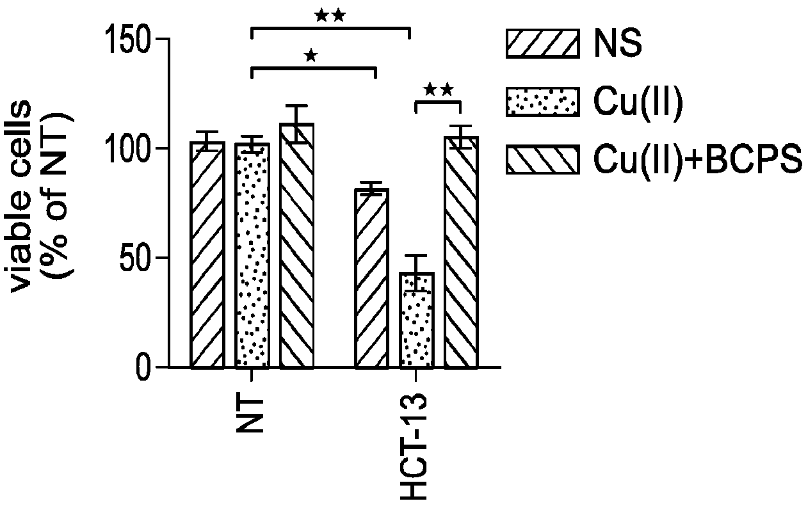
FIG. 1D: inhibition of proliferation of MIAPACA2 cells treated with HCT13 (25 nM)+Cu(II) (20 μM) for 24h±bathocuproine disulfonate (BCPS, 300 μM) measured by trypan blue exclusion.

The MIAPACA2 cell line, a well-characterized PDAC model that was highly sensitive to HCT13 treatment, was used to further investigate the mechanism of action of our lead compound. MIAPACA2 proliferation was measured in response to HCT13 in the presence and absence of 20 μM $CuCl_2$ (Cu(II)), as well as in response to 20 μM Cu(II) alone (FIG. 1B). The potency of HCT13 improved by greater than 5-fold under Cu(II) supplemented conditions, with its $IC_{90}$ decreasing from 110 nM to 21 nM. Importantly, Cu(II) supplementation alone did not affect proliferation at all. To probe whether HCT13 was acting as an ionophore, intracellular copper levels were measured using inductively coupled plasma mass spectrometry (ICP-MS). In the presence of HCT13, intracellular copper levels increased both with and without Cu(II) supplementation (FIG. 1C). Additionally, treatment with bathocuproine disulfonate (BCPS), a membrane impermeable Cu(II) chelator, abrogated the cytotoxicity of HCT13 in the presence of Cu(II), indicating that the growth inhibitory effect of HCT13 is largely dependent upon the availability of copper (FIG. 1D). Collectively, this data indicates that HCT13 is a Cu(II) ionophore which increases intracellular copper concentration, and whose cytotoxicity is copper-dependent.

Figure 1E:
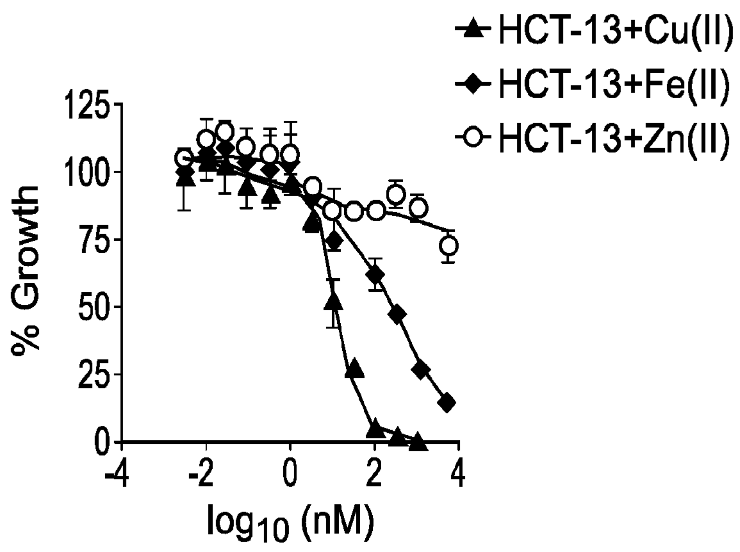
FIG. 1E: proliferation rate of MIAPACA2 PDAC cells measured by CellTiterGlo following HCT-13 treatment for 72h±Cu(II), Fe(II), or Zn(II)(20 μM). (mean±SD, n=2, one-way ANOVA corrected for multiple comparisons by Bonferroni adjustment, * P<0.05; P<0.01; *P<0.001).
Figure 1F:
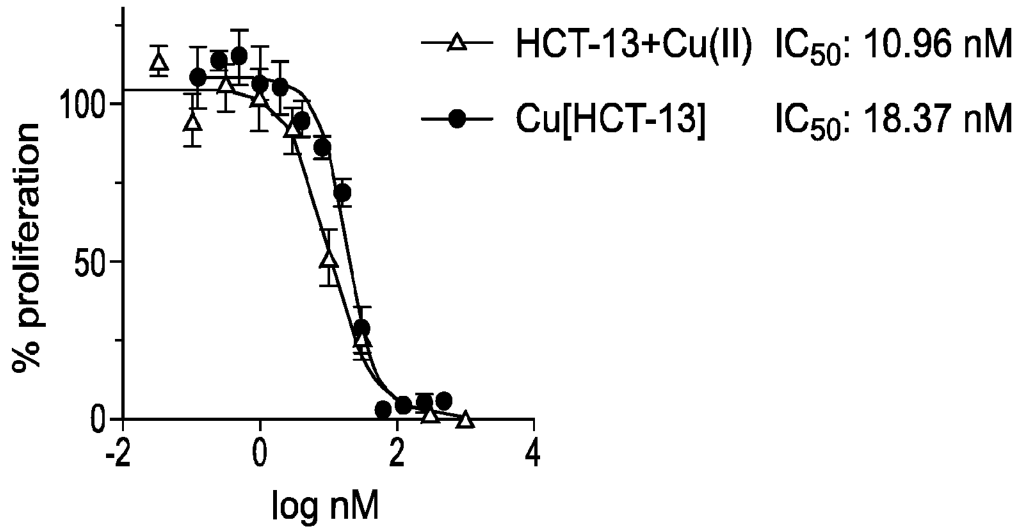
FIG. 1F: shows the CellTiterGlo assay of cell viability-proliferation in MIAPACA2 cells treated with HCT-13+CU(II) and those treated with Cu[HCT-13] for 72h.
Figure 1G:
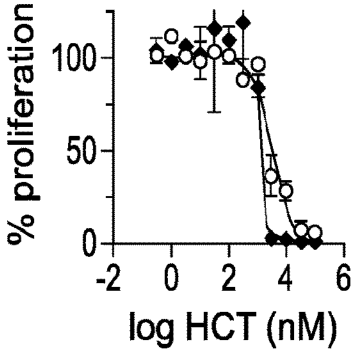
Figure 1H:
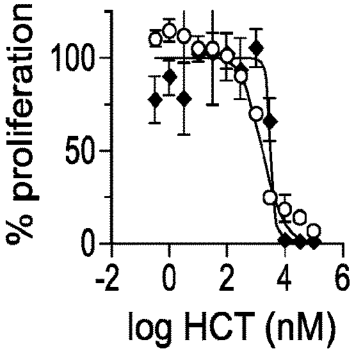
Figure 1I:
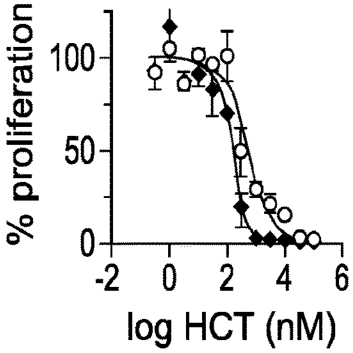
Figure 1J:
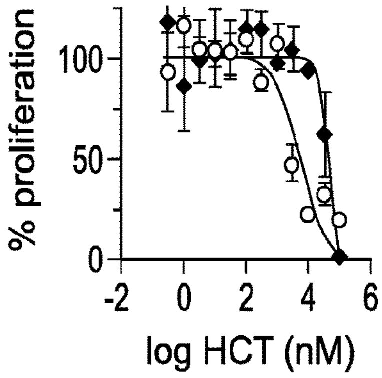
Figure 1K:
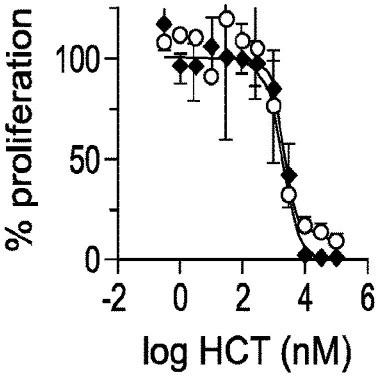
Figure 1L:
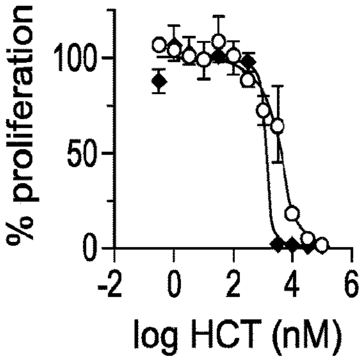
Figure 1M:
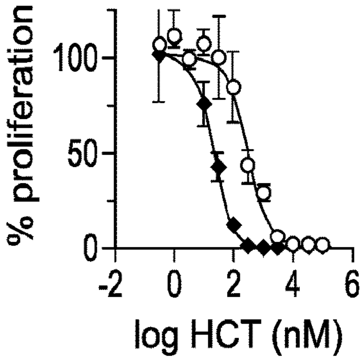
Figure 1N:
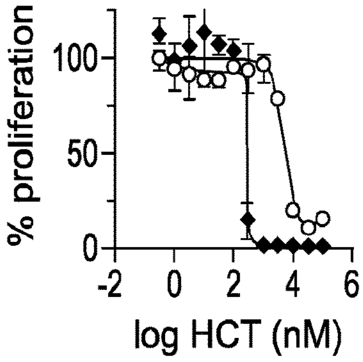
Figure 1O:
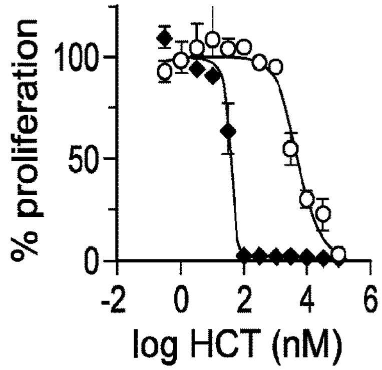
Figure 1P:
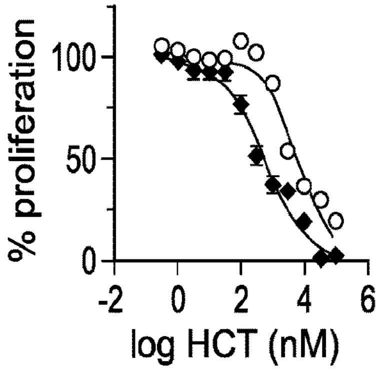
Figure 1Q:
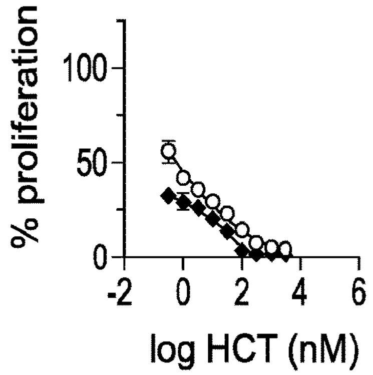
Figure 1R:
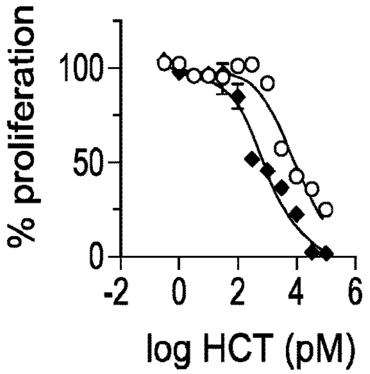
Figure 1S:
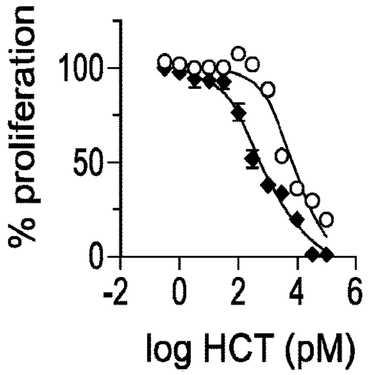
Figure 1T:
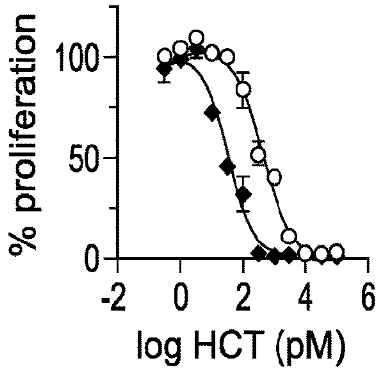
Figure 1U:
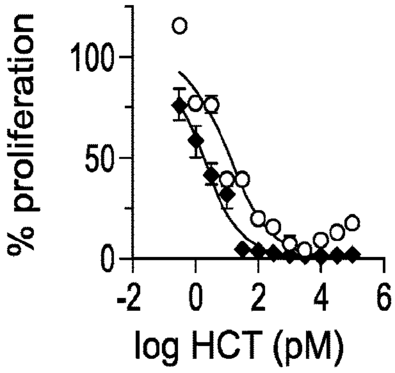

The inventors also determined the effects of supplementation with iron and zinc upon the antiproliferative activity of HCT-13 and found its potency was highest in the presence of Cu(II), diminished but still active in the presence of Fe(II), and largely inactive in the presence of Zn(II) (FIG. 1E). Collectively, these data demonstrate that HCT-13 is a Cu(II) ionophore which increases intracellular copper concentration and whose cytotoxicity is copper-dependent.

Figure 2A:
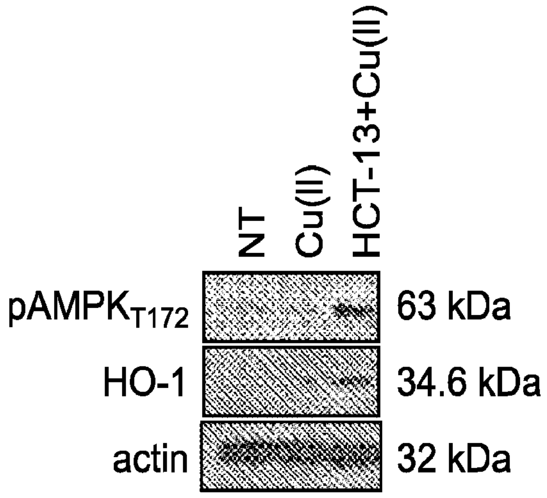
FIGS. 2A-2I.
Figure 2B:
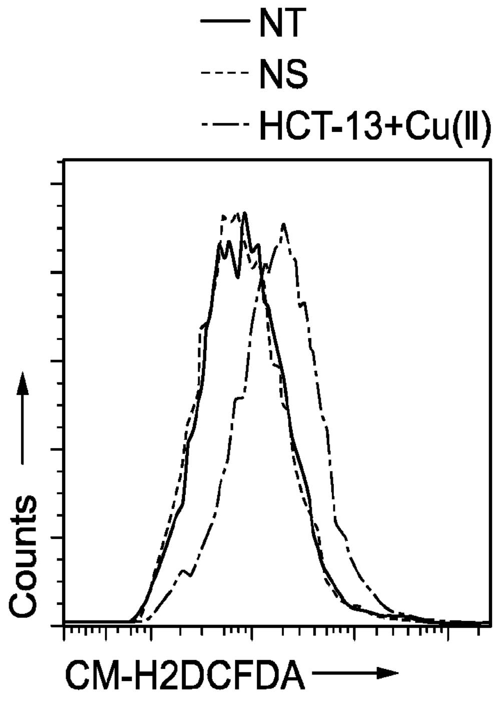
Figure 2C:
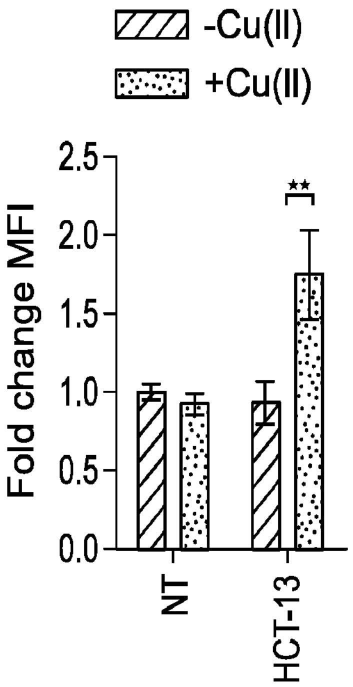

While HCT13 in the presence of Cu(II) exhibited nanomolar potency against the panel of solid cancer models, the underlying reasons remained unknown as the canonical mechanism of HCT cytotoxicity is poorly defined in the literature. Cu(II)-supplemented MIAPACA2 cells treated with HCT13 showed induction of AMPK phosphorylation (T172) at 24 hours, demonstrating suppression of mitochondrial oxidative phosphorylation (FIG. 2A). Further, HCT13 treatment increased heme oxygenase-1 (HO-1) levels in MIAPACA2 cells, indicative of ROS induction (FIG. 2A). Based on the immunoblot results, it was discovered that treatment with HCT13 induced ROS generation detectable by CM-$H_2$DCFDA staining (FIG. 2B). ROS generation resulting from HCT13 treatment of MIAPACA2 cells was also observed in the mitochondria, as measured by mitochondria-specific dye MitoSOX (FIG. 2C).

Figure 3A:
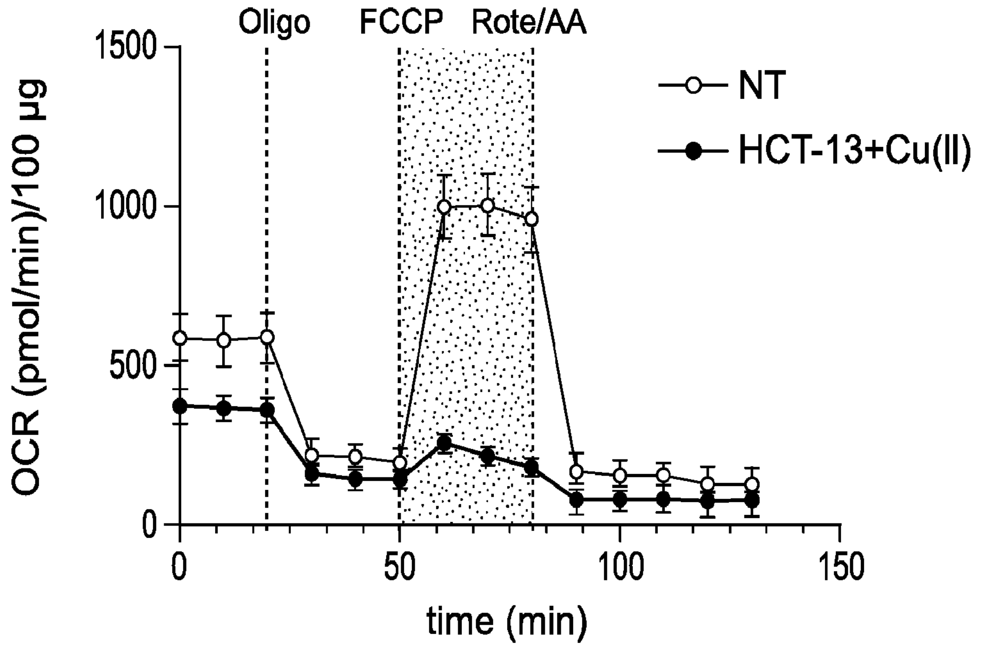
FIGS. 3A-3D show that HCT13 alters cellular energetics through inhibition of electron transport chain and has selective mitochondrial toxicity.
Figure 3B:
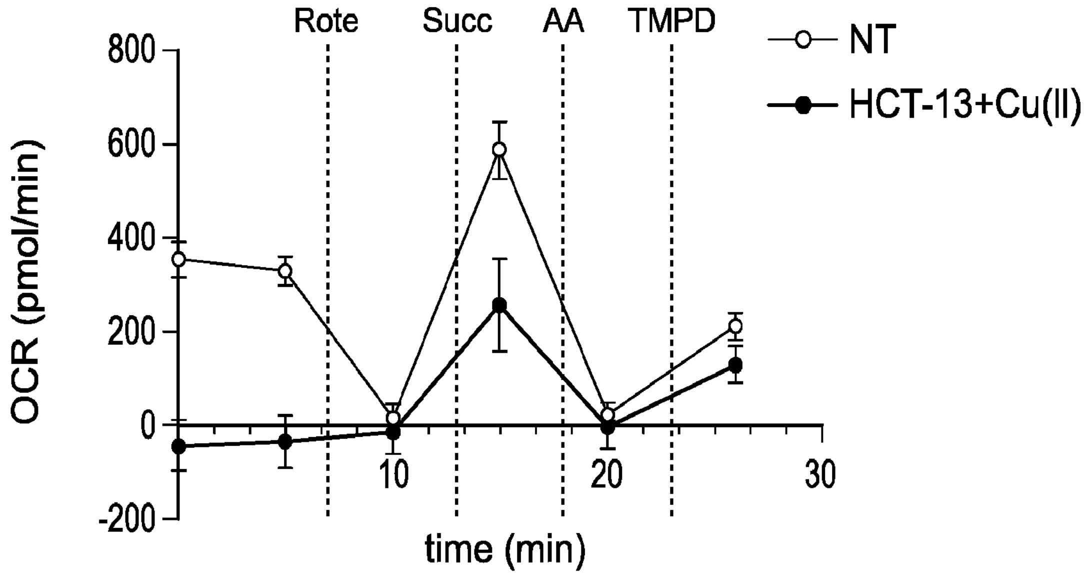

Considering the canonical role AMPK plays in energy homeostasis, and the implication that AMPK activation may signal mitochondrial dysfunction (Ref 49), the metabolic status of MIAPACA2 cells treated with HCT13 for 24 hours with and without 20 μM Cu(II) was compared using a Seahorse Bioscience XFe24 analyzer. In the presence of Cu(II), HCT13 significantly reduced both the basal respiration and maximum respiratory capacities of MIAPACA2 cells, indicating mitochondrial electron transport chain (mtETC) impairment (FIG. 3A). In vitro mitochondrial complex activity following HCT13 treatment was dissected by an electron flow assay in isolated mitochondria, which showed decreased activity of complexes I and II (FIG. 3B).

Figure 3C:
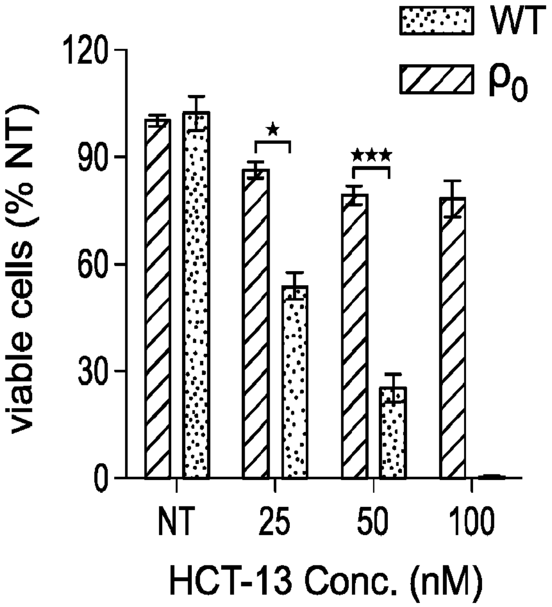
Figure 3D:
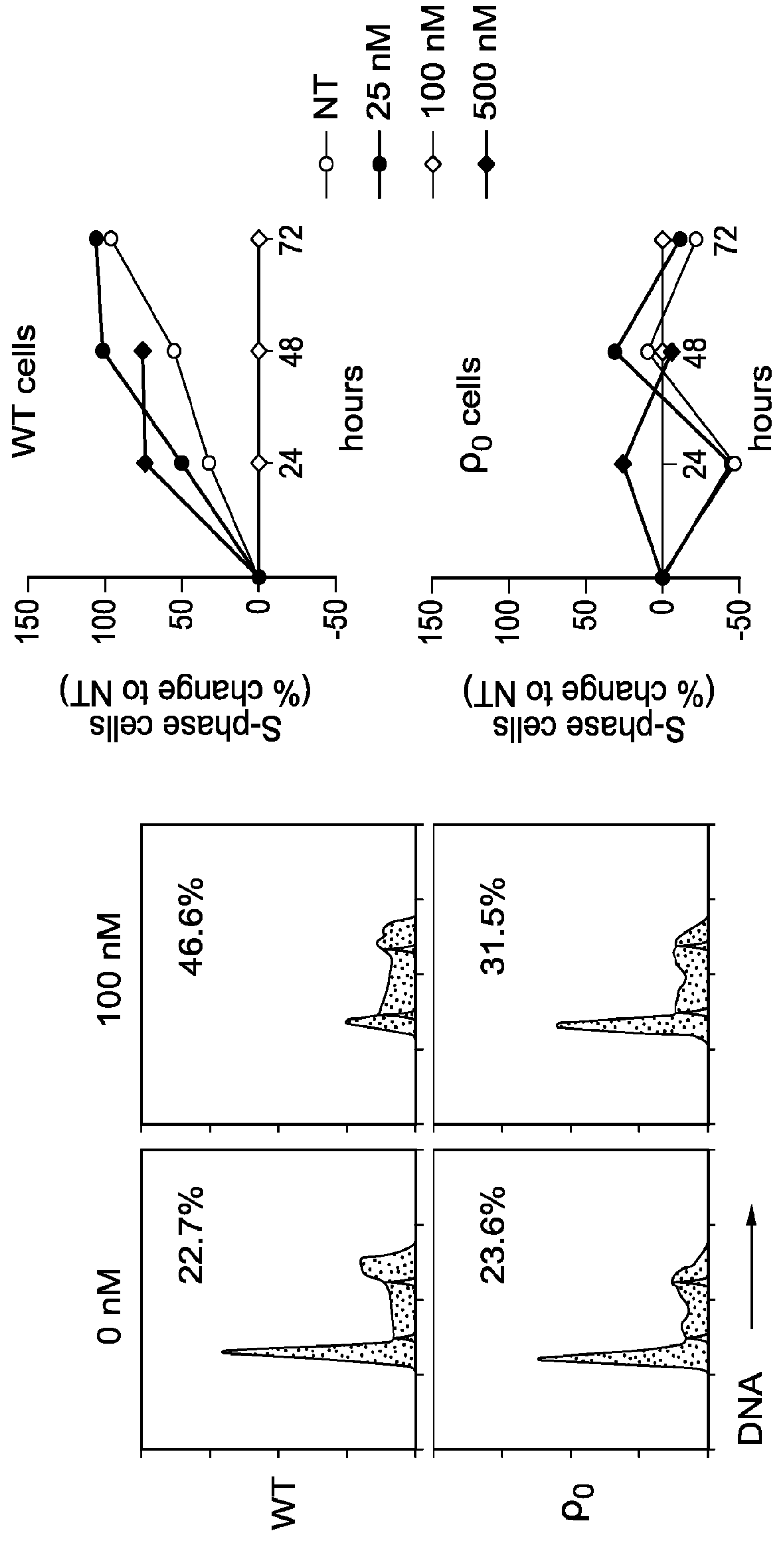
Figure 5A:
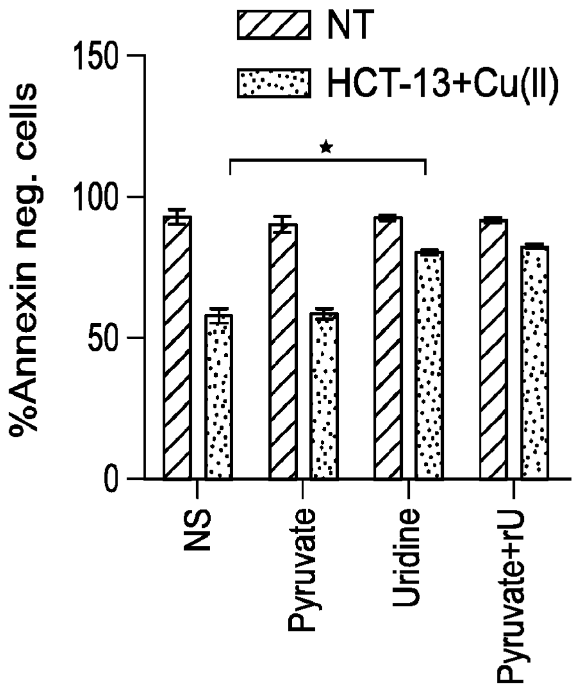
FIGS. 5A-5B shows that cell proliferation inhibition induced by HCT13 is partially rescued by uridine supplementation.
Figure 5B:
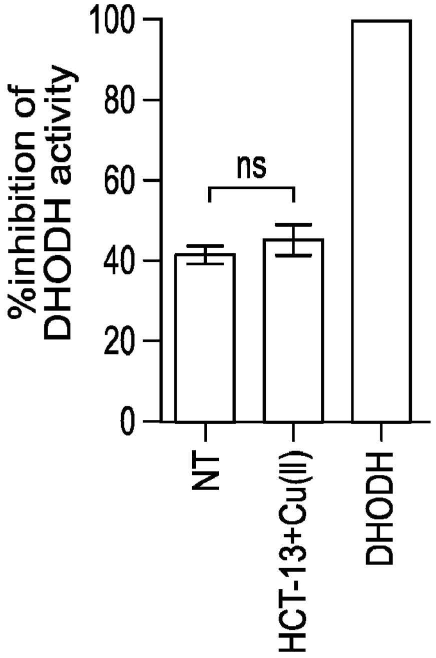

These findings indicate that HCT13 inhibited mtETC activity but did not indicate whether the cytotoxicity stemmed from effects independent of mitochondrial function. Another HCT compound, Dp44mT, was reported to increase AMPK expression and induce ROS, although its cytotoxicity was not attributed to the functionality of the mitochondria. (Ref 50). To determine whether the cytotoxicity of HCT13 was mitochondria-dependent, its effects upon 143 BTK $\rho_0$, an mtDNA-deficient fibroblast cell line, was examined. Both 143 BTK $\rho_0$ and parental (wild type, WT) cells were treated with HCT13+20 μM Cu(II) for 48 hours, after which cell viability was determined through trypan blue staining (FIG. 3C). Compared to WT, the po cells were significantly less sensitive to the treatment. The cytotoxicity of HCT13 was partially abolished by supplementation with uridine (rU) but not by pyruvate, indicating disruption to the supply of pyrimidine nucleotides in addition to impaired mitochondria (FIG. 5A). Proper mitochondrial function is necessary for the action of dihydroorotate dehydrogenase, an enzyme critical for the de novo production of pyrimidine nucleotides, and one for which HCT13 did not demonstrate affinity (FIG. 5B). Additionally, cell cycle analysis revealed marked S-phase arrest in 143 BTK WT cells but not in 143 BTK $\rho_0$ (FIG. 3D). Taken together, these results indicate that the cytotoxic effects of HCT13 are mitochondria-dependent and suggest that HCT13 may be indirectly targeting DHODH, and thus de novo pyrimidine nucleotide production, through induction of mitochondrial dysfunction.

Example 4

Figure 4A:
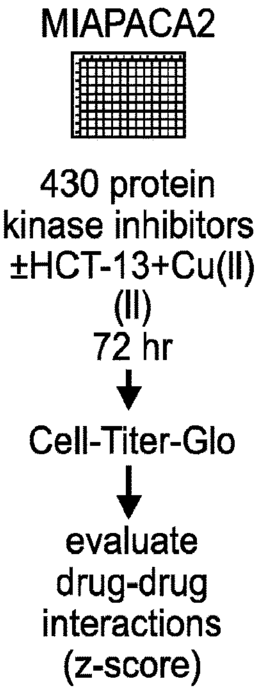
FIGS. 4A-4G show the chemical genomics screen identifying the replication stress response pathway as an actionable co-dependency of HCT13-treated cells.

To identify potential resistance mechanisms and synergistic interactions with HCT13, the inventors performed an unbiased pharmacological inhibition screen using a chemical genomics platform consisting of 430 kinase inhibitors (Selleckchem, Cat. L1200). MIAPACA2 cells were treated with the 430-member library, covering a 7-point concentration range spanning between 6.5 nM and 5 μM, with and without 25 nM HCT13 in presence of 20 μM $CuCl_2$. After 72 hours of incubation, ATP content was measured using CellTiter-Glo (FIG. 4A). A composite synergy score was calculated for each combination, defined as the sum of the Bliss Additivity Score (% proliferation inhibition observed−% proliferation inhibition expected). A positive synergy score indicates synergistic interaction, and a negative score indicates less-than-additive interaction (i.e., antagonism).

Figure 4B:
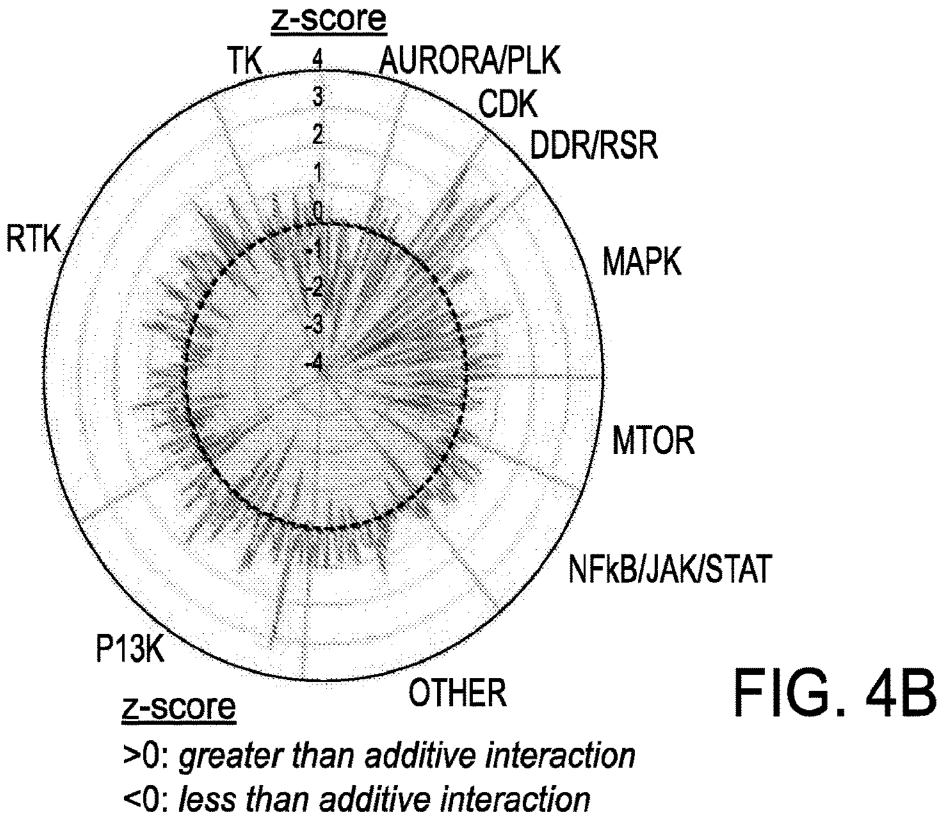
Figure 4C:
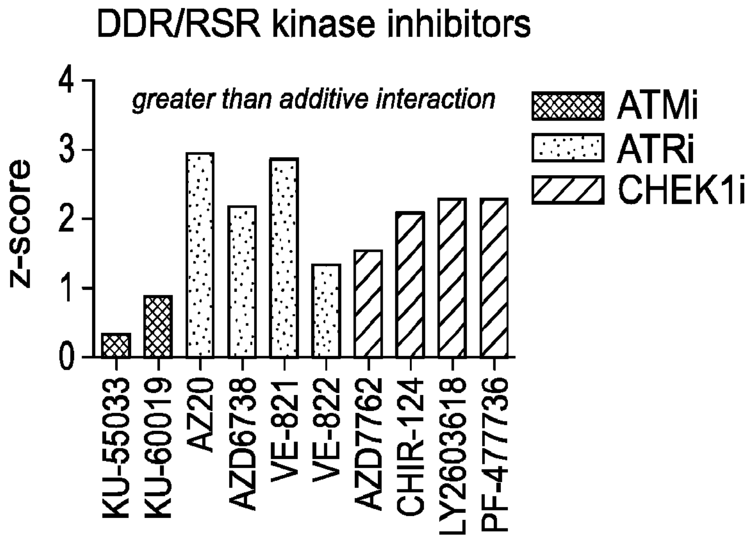

The ten highest scoring compounds were kinase inhibitors contained in the DNA damage response/replication stress response (DDR/RSR) module, with the ataxia telangiectasia mutated serine/threonine kinase (ATM)/checkpoint kinase 2 (CHK2), and Rad3-related serine/threonine kinase (ATR)/CHK1 pathways featuring as the most prominent codependency (FIG. 4B-4C). All eight ATR and CHK1 inhibitors in the library scored positively, indicating that the DDR/RSR pathways are activated by HCT-13. Upon HCT13+Cu(II) treatment, the inventors consistently observed phosphorylation of the downstream targets of ATR and ATM, CHEK1 and CHEK2, respectively, indicating activation of this pathway as an adaptive resistance mechanism. The synergistic interaction of HCT13 with ATR inhibition was further validated using cell death assays measured by Annexin V/PI (apoptosis) and Trypan Blue Viability Staining in PDAC (MIAPACA2, CFPAC-1) and PC (C4-2) cell lines (FIGS. 4E-4F, FIGS. 6B-6C).

Figure 4D:
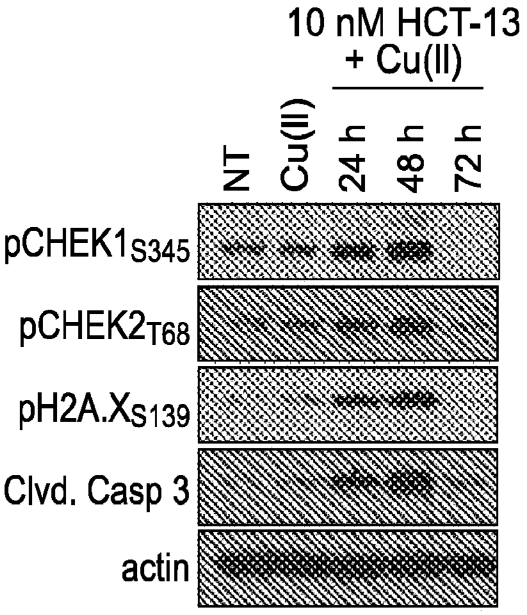
Figure 4E:
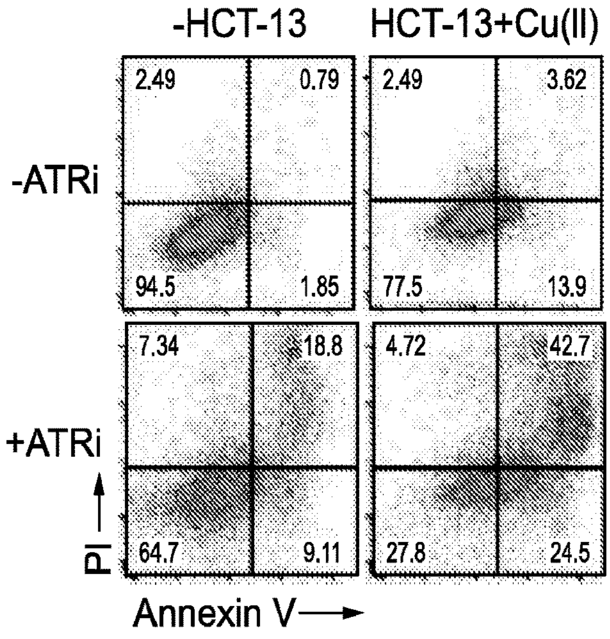
Figure 4F:
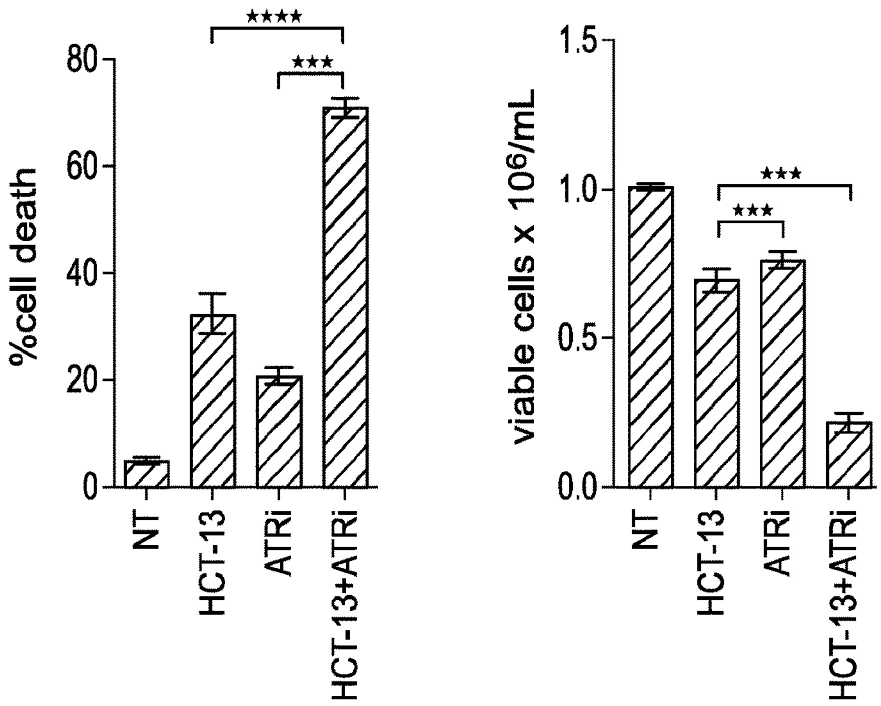
Figure 4G:
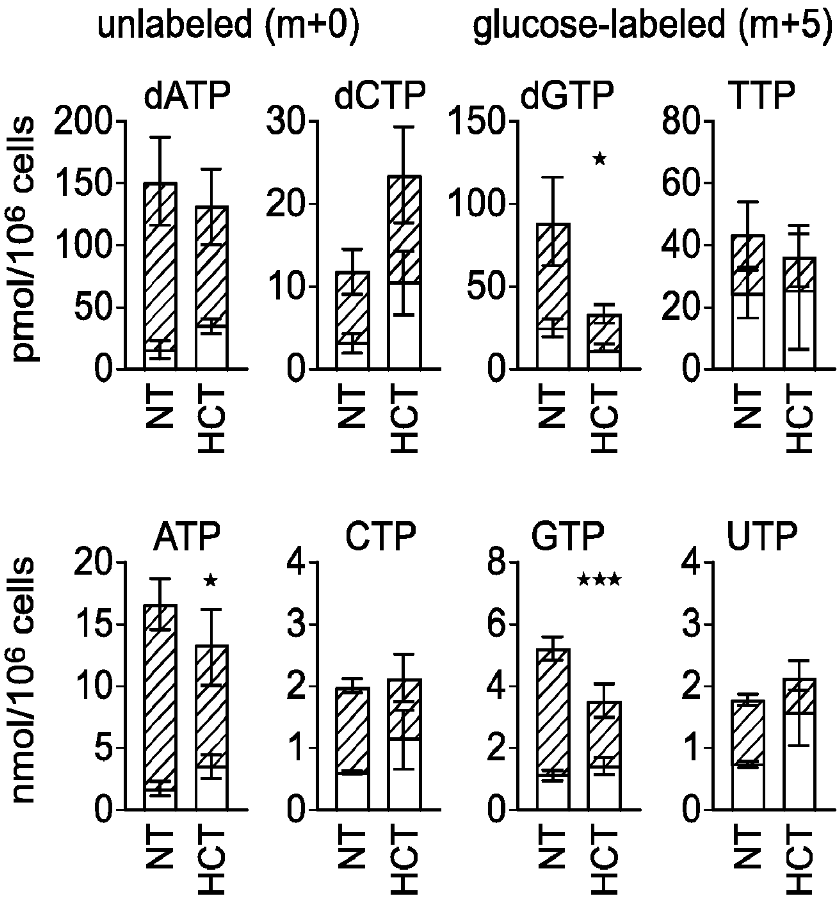

Furthermore, phosphorylation of CHEK1 and CHEK2 kinases was observed upon HCT-13+Cu(II) treatment, as well as the induction of DNA damage marker pH2AX and by cleavage of apoptotic marker caspase 3 (FIG. 4D). These observations are indicative of DDR/RSR pathway activation, which was hypothesized to arise from nucleotide insufficiency and/or, given the ability of copper to generate ROS, from ROS-mediated DNA damage. (Halliwell, et al, Meth. Enzymol. 1990, 186:1-85; Duncan et al, Metallomics 2012, 4(2):127-138; Willis et al, Proc Natl Acad Sci USA 2013, 110(26):10592-10597). To test the former hypothesis, nucleotide levels were measured in treated and non-treated cells using liquid chromatography-tandem mass spectrometry with multiple reaction monitoring (LC-MS/MS-MRM) as previously described by Le et al, Nature Communications 2017, 8(1):1-14. Both dGTP and rGTP pools were decreased in HCT-13-treated cells, while levels of the other nucleotides either increased or the change was statistically insignificant (FIG. 4G). These findings indicate that HCT-13 preferentially decreases the dGTP and rGTP pools, potentially via oxidative processes as guanine is the most readily oxidized nucleobase. (Kino et al, Genes Environ. 2017, 39:2). Together with the immunoblot results (FIG. 4D), these data indicate that dGTP pool insufficiency in HCT-13-treated cells triggers the activation of the intra-S checkpoint, as measured by increased pChk1 levels, which in turn renders these cells dependent upon the activity of the replication stress response pathway.

Figure 2D:
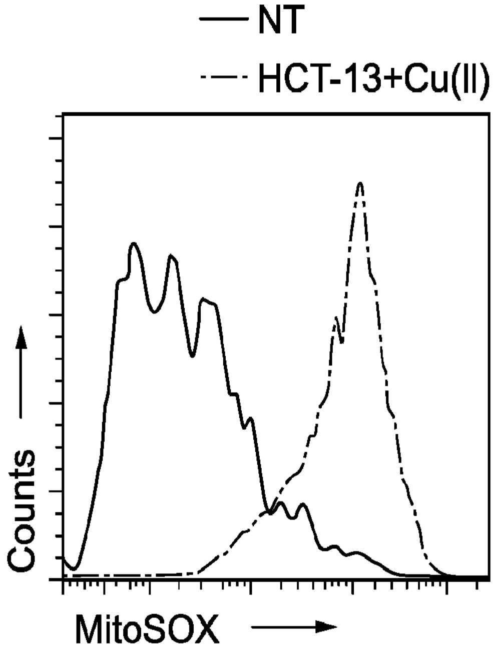
Figure 2E:
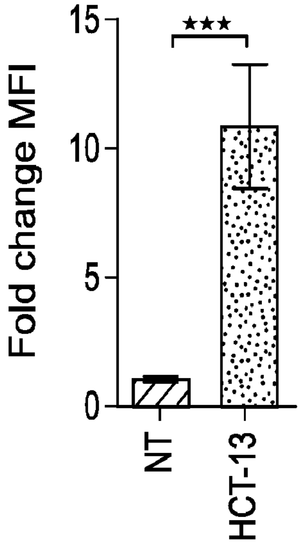
Figure 2F:
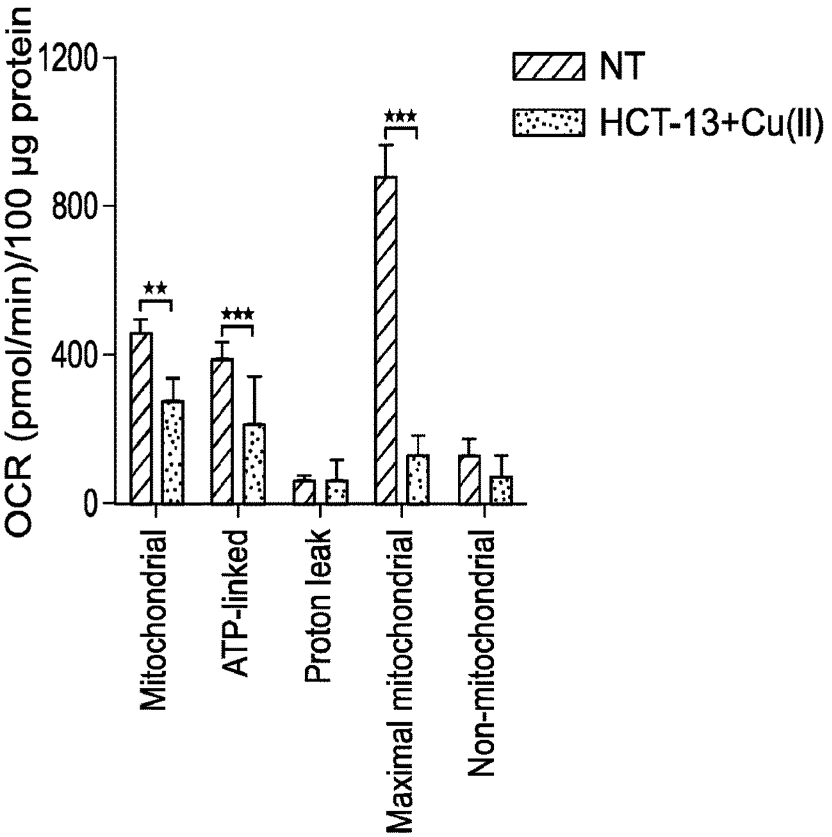
Figure 2G:
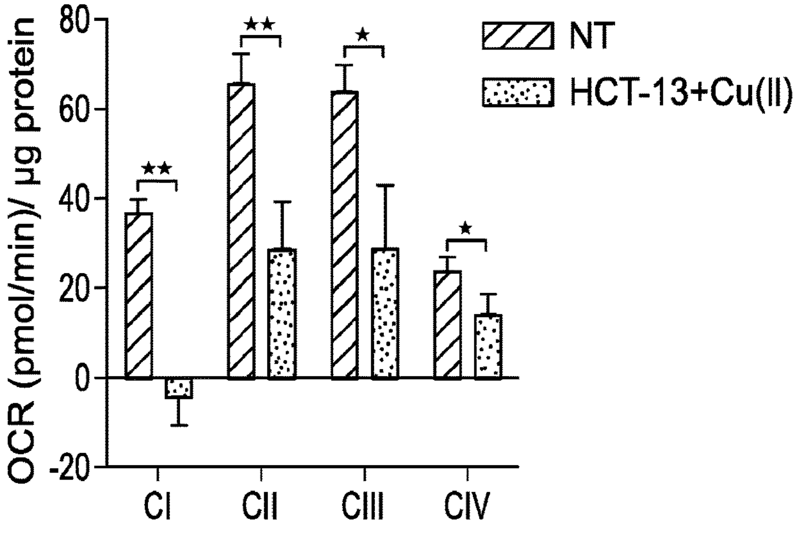

Given that our dGTP and rGTP pool measurements pointed towards a guanosine-depleting mechanism of action, we set out to determine whether our lead compound was giving rise to ROS. We found that HCT-13 treatment induced ROS generation detectable by CM-H2DCFDA staining in MIAPACA2 cells (FIGS. 2B-2C) (Dikalov et al, Antioxid. Redox Sign. 2014, 20(2):372-382). ROS generation was also observed in the mitochondria, as measured by mitochondria-specific dye MitoSOX (FIGS. 2D-2E). (Dikalov et al, Antioxid. Redox Sign. 2014, 20(2):372-382). To further probe the ramifications of the HCT-13-generated ROS, we inquired as to whether oxidative phosphorylation (OXPHOS) in MIAPACA2 cells was altered following treatment. A Seahorse Assay was performed to measure the alteration in overall OXPHOS, and an electron flow assay was performed in isolated mitochondria to assess which electron transport chain (ETC) complex is impacted (FIGS. 2F-2G, FIGS. 6A-6B). (Wu et al, Am. J. Physiol., Cell Physiol. 2007, 292(1):C125-C136; Brand et al, Biochem. J. 2011, 435(2):297-312). These assays showed that cell respiratory capacity decreased significantly upon HCT-13 treatment as measured by reduced oxygen consumption rate (OCR), that OXPHOS capacity was impaired, and that ETC Complex 1 was most dramatically affected.

Summary of Examples 1-4

The study primarily focused on two modifications of the HCT-1 scaffold during synthetic planning: fluorination of the isoquinoline ring, and sequential methylation of the 4' amine. Though the 5-, 7-, and 8-fluoro-substituted analogs of HCT-1 were previously reported, and while it was apparent that fluorine position could influence a compound's toxicity and produce differential antiproliferative effects upon various cell lines, no trends had previously emerged regarding the effects of fluorine position.[5] Additionally, multiple groups have shown that 4' amine methylation potentiates the activity HCTs such as pyridine 2-carboxyaldehyde thiosemicarbazones and 2-acetylpyridine thiosemicarbazones.[24,39,40] The inventors therefore sought to synthesize the novel 4- and 6-fluoro analogs of HCT-1 and investigate what effects sequential 4' amine methylation had upon antiproliferative activity. Following the isoquinoline HCT synthetic campaign, analysis of the antiproliferative data revealed several trends. In conditions without copper supplementation, fluorination at either the 4- or 6-position of the isoquinoline ring led to an increase in potency for five out of six compounds, when compared with their corresponding non-fluorinated analogs). In some cases, the change was unexpected and dramatic, e.g., the $IC_{90}$ of HCT13 was nearly 270-fold lower than its non-fluorinated analog HCT11. Secondly, 4' amine methylation in the absence of isoquinoline substitution or copper supplementation was detrimental to activity, as demonstrated by the decrease in potencies for HCT6 and HCT11 when compared with 4' primary amine HCT1. However, combining 4' amine methylation and isoquinoline substitution in a single compound, as in HCTs 7-10, 12, and 13, produced synergistic (i.e., greater-than-additive) antiproliferative effects when compared with either their 4' primary amine or unsubstituted isoquinoline analogs. HCT13 again exemplified this trend, with potency nearly 270-fold greater than its non-substituted isoquinoline analog HCT11 and nearly 50-fold greater than its non-methylated analog HCT3. Finally, the antiproliferative activities of the presently described isoquinoline HCTs were potentiated by supplementation with physiologically relevant levels of copper (with HCT5 being the exception). HCT13 was particularly potent both in the absence and presence of copper supplementation.

The potency of HCT13 is highlighted by its nanomolar $IC_{90}$ values against a panel of PDAC, SCLC, PC, and leukemia cancer models in the presence of physiologically relevant levels of copper (FIG. 1A). The use of copper-chelating small molecules in anticancer therapy is an established strategy which is executed either through sequestration of copper from tumor tissue, or through increasing intracellular copper to cytotoxic levels.[51] HCT13 behaved as an ionophore and increased intracellular levels of copper, both in the presence and absence of copper supplementation. This property is essential for the cytotoxicity of HCT13, as sequestration of copper via BCPS-chelation negated HCT13's growth inhibitory effects (FIG. 1D). It was further demonstrated that HCT13 leverages copper to effect its cytotoxicity in a mitochondria-dependent manner. Specifically, the data indicate that HCT13 induces mitochondrial dysfunction and mitochondria-dependent S-phase arrest, and generates ROS and oxidative stress in different cancer models. Strikingly, mitochondria-deficient 143 BTK po cells were significantly less sensitive to HCT13 in the presence of copper compared to their parental 143 BTK WT counterpart, providing further evidence of mitochondria-dependent cytotoxicity (FIG. 3C). It is possible that the observed S-phase arrest results from disruption of the de novo pathway (DNP) for pyrimidine nucleotide biosynthesis, which supplies cells with the pyrimidine nucleotides necessary for replication. The lone oxidation step of the pyrimidine DNP is carried out by dihydroorotate dehydrogenase (DHODH), an enzyme located in the inner mitochondrial membrane, which utilizes ubiquinone as a redox partner. Without a properly functioning mitochondrial ETC, DHODH does not have access to the levels of ubiquinone necessary for the oxidative enzyme to adequately turn-over, leading to shortages in pyrimidine nucleotides and corresponding S-phase arrest.[52-57]

In general, cancer cells exhibit higher levels of ROS and higher baseline oxidative stress than healthy cells, which may imbue HCT13 with selectivity towards cancerous tissue. The ROS and mitochondrial dysfunction produced in MIAPACA2 cells by HCT13 lead to an increase in DNA damage marker pH2AX, which may explain why HCT13 synergized with inhibitors of ATR (Ataxia-Telangiectasia Mutated (ATM) and Rad3-related protein kinase), the most upstream kinase in the DNA-damage response/replication stress response (DDR/RSR) pathway. Synergy with DDR/RSR inhibitors may increase the therapeutic window of HCT13, should it be administered in combination therapy. The observed mechanisms of action of HCT13 suggest that it may also synergize with radiotherapy, as therapeutic ionizing radiation increases ROS, thereby increasing oxidative stress and DNA damage in the targeted area(s). Therefore, HCT13 could also function as a radiosensitizer by further increasing the load of ROS, oxidative stress, and DNA damage when administered in combination with radiation therapy. Taken together, the potency of HCT13 as a single agent therapeutic against aggressive solid tumor models, its mechanism of action, and the observed synergy with ATR inhibitors warrant further testing in vivo.

Conclusion Based on Examples 1-4

The inventors have expanded upon a class of isoquinoline-based HCTs to produce a set of novel antiproliferative compounds. It has been demonstrated the synergistic effects of combining 4' amine methylation with isoquinoline substitution and identified HCT13 as a highly potent antiproliferative which is active against a panel of PDAC, SCLC, PC, and leukemia cancer models. It has been shown that the presence of physiologically-relevant levels of Cu(II) greatly potentiated the activity of HCT13, and subsequent investigation into HCT13's mechanism of action revealed that it acts as a copper ionophore and requires copper to effect its cytotoxicity. Furthermore, HCT13 induced ROS production, oxidative stress, S-phase arrest, and mitochondrial dysfunction, which may contribute to indirect inhibition of DHODH. Lastly, a high-throughput phenotypic screen of protein kinase inhibitors was used to identify actionable adaptive resistance mechanisms of HCT13-treated cells and identified the DDR/RSR pathways as actionable vulnerabilities. Specifically, it is shown that ATR inhibition synergizes with HCT13 in the presence of physiologically-relevant levels of Cu(II). Taken together, this study demonstrated the potential of HCT13, and the other compounds described herein, for use in anti-cancer therapy, either as a single agent or as part of a larger combination therapy.

Materials and Methods for Examples 1-4

Cell culture and culture conditions: Pancreatic adenocarcinoma cell lines: PATU8988T, MIAPACA2, SU8686, PSN1, HPAC, BXPC3, DANG, SUIT2, A13A, CAPAN2, T3M4, A2.1, HUPT4, XWR200, L36PL, YAPC, PANC0327, PANC1, PATU8902, HPAF11, ASPC1, PANC0813, PANC0203, HS766T, SW1990, and CFPAC1; prostate cancer cell lines: 22Rv1, LNCaP, RM1 and C4-2; and small cell lung carcinoma cell lines: NCI-H526, NCI-H146, and NCI-H1963 were obtained from American Type Culture Collection (ATCC). 143 BTK WT and 143 BTK $\rho_0$, BJ WT and BJ $\rho_0$ cells were gifts from Prof. Michael Teitell in UCLA. Murine Prostate cancer cell lines MyC CaP was a kind gift from Prof. D L J Thorek at WUSTL. Murine Pancreatic cancer cells KP4662 was kind gift from Prof. Robert Vonderheide at UPenn. With a few exceptions, cell lines were cultured in DMEM (Corning) or RPMI (Corning) containing 10% fetal bovine serum (FBS, Omega Scientific) and were grown at 37° C., 20% $O_2$ and 5% $CO_2$. All cultured cells were incubated in antibiotic free media and were regularly tested for mycoplasma contamination using Myco-Alert kit (Lonza) following the manufacturer's instructions, except that the reagents were diluted 1:4 from their recommended amount.

Proliferation assay: Cells were plated in 384-well plates (500 cells/well for adherent cell lines in 30 μl volume). Drugs were serially diluted to the desired concentrations and an equivalent volume of DMSO was added to vehicle control. Following 72 h incubation, ATP content was measured using CellTiter-Glo reagent according to manufacturer's instructions (Promega, CellTiter-Glo Luminescent Cell Viability Assay), and analyzed by SpectraMax luminometer (Molecular Devices). $IC_{50}$ and $IC_{90}$ values, concentrations required to inhibit proliferation by 50% and 90% respectively compared to DMSO treated cells, were calculated using Prism 6.0 h (Graphpad Software).

Western blot: Cells were lysed using RIPA buffer supplemented with protease (ThermoFisher, 78,430) and phosphatase (ThermoFisher, 78,420) inhibitors, scraped, sonicated, and centrifuged (20,000×g at 4° C.). Protein concentrations in the supernatant were determined using the Micro BCA Protein Assay kit (Thermo), and equal amounts of protein were resolved on pre-made Bis-Tris polyacrylamide gels (Life Technologies). Primary antibodies: pAMPK$_{T172}$ (Cell signaling, #2535, 1:1000), HO-1 (Cell signaling, #5061S, 1:1000), pS345 CHEK1 (Cell signaling, #2348L, 1:1000), pT68 CHEK2 (Cell signaling, #2197 S, 1:1000), pS139 H2A.X (Millipore, 05-636, 1:1000), clvd. Casp3 (Cell signaling, #9662, 1:1000), and anti-actin (Cell Signaling Technology, 9470, 1:10,000). Primary antibodies were stored in 5% BSA (Sigma-Aldrich) and 0.1% $NaN_3$ in TBST solution. Anti-rabbit IgG HRP-linked (Cell Signaling Technology, 7074, 1:2500) and anti-mouse IgG HRP-linked (Cell Signaling Technology, 7076, 1:2500) were used as secondary antibodies. Chemiluminescent substrates (ThermoFisher Scientific, 34,077 and 34,095) and autoradiography film (Denville) were used for detection.

Viability/Apoptosis assay: Viable cells were measured by Trypan blue staining using vi-cell counter (Beckman Coulter, CA, USA). Apoptosis and cell death were assayed using Annexin V-FITC and PI according to manufacturer's instructions (FITC Annexin V Apoptosis Detection Kit, BD Sciences, #556570).

Cell cycle: Cell cycle was assessed using Propidium iodide staining at indicated timepoints. Cells were pulsed with EdU 1 h before collection at different time points. Cells were fixed 4% paraformaldehyde, permeabilized with perm/wash reagent (Invitrogen), stained with Azide-AF647 (using click-chemistry, Invitrogen; Click-iT EdU Flow cytometry kit, #C10634) and FxCycle-Violet (Invitrogen), and then analyzed by flow cytometry (a detailed description is available in the Supplementary Information).

ROS Measurements: Cellular ROS measurement was assayed with CM-H2DCFDA staining after treatment according to manufacturer's instructions (Reactive Oxygen Species (ROS) Detection Reagents, Invitrogen, #D399). The cells were then incubated with 5 μM of CM-H2DCFDA for 30 min, spun down at 450× g for 4 mins, and the supernatant was replaced with fresh media containing lethal compounds and/or Cu(II). Then, the cells were incubated for 30 mins, spun down, and the supernatant was replaced with PBS. The samples were analyzed using flow cytometry.

Mitochondrial ROS was measured using MitoSOX staining according to manufacturer's instructions (MitoSOX, Invitrogen, #M36008). Cells were treated with HCT-13, washed and treated with MitoSOX. Cells were then incubated for 30 minutes at 37° C. After incubation, media is aspirated and cells are washed with PBS and analyzed by flow cytometry.

Mito Stress Test and Electron Flow Assay: All oxygen consumption rate (OCR) was measured using a XF24 Analyzer (Agilent) and normalized per μg protein. For cellular OCR, cells were incubated in unbuffered DMEM containing 25 mM glucose, 1 mM pyruvate and 2 mM glutamine. OCR was measured before (total respiration) and after the sequential injection of 1 μM oligomycin (complex V inhibitor), 0.75 μM FCCP (uncoupler), and 1 μM of rotenone and myxothiazol (complex I and III inhibitors, respectively), as described previously (1). Mitochondrial respiration was calculated by subtracting the non-mitochondrial respiration left after rotenone and myxothiazol injection. Oligomycin-sensitive respiration represents ATP-linked respiration (coupled respiration). To measure electron transport chain complex activity from cells, cells were incubated in MAS buffer with 10 mM pyruvate (complex I substrate), 2 mM malate, 4 μM FCCP, 4 mM ADP, and 1 nM of XF Plasma Membrane Permeabilizer (PMP) reagent (Agilent). OCR was measured before and after the sequential injection of 2 μM rotenone, 10 mM succinate (complex II substrate), 4 μM antimycin A (complex III inhibitor), and a mix of 10 mM ascorbate and 100 μM TMPD (complex IV substrates), as described previously (2). Antimycin A-sensitive respiration represents the complex III respiration. To measure OCR directly from mitochondria, mitochondria were isolated from fresh mouse liver by dual centrifugation at 800 g and 8000 g and seeded by centrifugation (2). Mitochondria were incubated with 1 mM pyruvate (complex I), 2 mM malate, 4 μM FCCP in MAS buffer, as well as the "corresponding drugs" for 30 min at 37° C. OCR was measured before and after the sequential injections described in the previous paragraph.

Intracellular Cu(II) measurement: Cells were plated in 6-well plates and cultured for one day. Vehicle of HCT-13 were added to the cells the following day and incubated for 24 hours. The plates were then washed 2 times with PBS containing 1 mM EDTA and 2 times with PBS alone. The concentration of Cu(II) was measured using Inductive Coupled Plasma Mass Spectrometry (ICP-MS) using standard procedure.

DHODH activity: Recombinant protein was incubated in an aqueous solution (total volume, 1.0 mL) containing 500 μM DHO (Sigma, D1728), 200 mM K2CO3-HCl (pH 8.0), 0.2% triton x-100, and 100 μM coenzyme Q10 (Sigma, C9538) at 37° C. for 0, 15, 30, 45, or 60 min. An aliquot (100 μL) of the mixture of enzyme reaction mixture or cell/tissue lysate was mixed with 100 μL of 0, 0.5, or 1.0 μM orotic acid, 50 μL of H2O, 250 μL of 4.0 mM 4-TFMBAO (Sigma, 422231), 250 μL of 8.0 mM K3[Fe(CN)6] (Sigma, 244023), and 250 μL of 80 mM $K_2CO_3$ (Sigma, P5833) and then heated at 80° C. for 4.0 min. The reaction was stopped by cooling in an ice-water bath and the absorbance was measured with a spectrofluorometer (FP-6300 Jasco, Tokyo, Japan): excitation and emission wavelengths were 340 nm and 460 nm, respectively.

FACS analyses: All flow cytometry data were acquired on a five-laser LSRII cytometer (BD), and analyzed using the FlowJo software (Tree Star).

References for Specification and Examples 1-4

(1) Brockman et al, Cancer Res. 1956, 16, 167-170. (2) Beraldo et al, Mini Rev. Med. Chem. 2004, 4, 31-39. (3) Sartorellim, Biochem. Biophys. Res. Commun. 1967, 27, 26-32. (4) Liu, et al, J. Med. Chem. 1992, 35, 3672-3677. (5) Agrawal et al, J. Med. Chem. 1976, 19, 970-972. (6) French et al, J. Med. Chem. 1970, 13, 1117-1124. (7) French et al, Cancer Res. 1965, 25, 1454-1458. (8) Karp et al, Leuk. Res. 2008, 32, 71-77. (9) Le et al, Nat. Commun. 2017, 8, 241. (10) Ohui et al, J. Med. Chem. 2018, 62(2), 512-530. (11) Aye et al, J. Biol. Chem. 2012, 287, 35768-35778. (12) Ma et al, Invest. New Drugs 2008, 26, 169-173. (13) Knox et al, Invest. New Drugs 2007, 25, 471-477. (14) Yu et al, J. Med. Chem. 2009, 52, 5271-5294. (15) Salim et al, J. Oncotarget 2016, 7, 41363-41379. (16) Guo et al, J. Hematol. Oncol. 2016, 9, 98. (17) Malarz et al, Oncotarget 2018, 9, 17689-17710. (18) Finch et al, Adv. Enzyme Regul. 1999, 39, 3-12. (19) Yu et al, Clin. Cancer. Res. 2006, 12, 6876-6883. (20) Alvero et al, J. Soc. Gynecol. Investig. 2006, 13, 145-152. (21) Yu et al, Curr. Med. Chem. 2012, 19, 2689-2702. (22) Merlot et al, Antioxid. Redox Signal. 2013, 18, 973-1006. (23) Chaston et al, Clin. Cancer Res. 2003, 9, 402-414. (24) Cory et al, Biochem. Pharmacol. 1994, 48, 335-344. (25) Richardson et al, J. Med. Chem. 2009, 52, 1459-1470. (26) Popović-Bijelić et al, J. Inorg. Biochem. 2011, 105, 1422-1431. (27) Ishiguro et al, Biochem. Pharmacol. 2014, 91, 312-322. (28) Denoyer et al, Prostate 2015, 75, 1510-1517. (29) Madsen et al, Annu. Rev. Neurosci. 2007, 30, 317-337. (30) Jansson et al, J. Biol. Chem. 2015, 290, 9588-9603. (31) Whitnall et al, Proc. Natl. Acad. Sci. USA 2006, 103, 14901-14906. (32) Shimada et al, Cell Chem. Biol. 2018, 25, 585-594. (33) Chen et al, Cancer Res. 2006, 66, 10425-10433. (34) Brewer et al, Clin. Cancer Res. 2000, 6, 1-10. (35) Cen et al., Mol. Cancer Ther. 2002, 1, 197-204. (36) Müller et al., Science. 2007, 317, 1881-1886. (37) Purser et al, Chem. Soc. Rev. 2008, 37, 320-330. (38) Zhou et al, Chem. Rev. 2016, 116, 422-518. (39) Kowol et al, J. Med. Chem. 2009, 52, 5032-5043. (40) Kowol et al, J. Med. Chem. 2016, 59, 6739-6752. (41) Agrawal et al, J. Med. Chem. 1968, 11, 700-703. (42) Mooney et al, J. Med. Chem. 1974, 17, 1145-1150. (43) Denoyer et al, Oncotarget 2016, 7, 37064-37080. (44) Cater et al, ACS Chem. Biol. 2013, 8, 1621-1631. (45) Safi et al, Cancer Res. 2014, 74, 5819-5831. (46) Kodydkova et al, Pancreas 2013, 42, 614-621. (47) Lene et al, Cancer Res. Treat. 2016, 48, 1056-1064. (48) Zhang et al, J. Int. Med. Res. 2018, 46(12), 4863-4873. (49) Herzig et al, Nat. Rev. Mol. Cell Biol. 2018, 19, 121-135. (50) Krishan et al, Biochem. Biophys. Acta. 2016, 1863, 2916-2933. (51) Englinger et al, Chem. Rev. 2019, 119, 1519-1624. (52) Madak et al, Pharmacol. Ther. [Online early access, in press]. DOI: Published online: Oct. 19, 2018. (53) Loffler et al, C. Mol. Cell Biochem. 1997, 174, 125-129. (54) Rawls et al, Eur. J. Biochem. 2000, 267, 2079-2087. (55) Zameitat et al, Appl. Environ. Microbiol. 2007, 73, 3371-3379. (56) Lane et al, Nucleic Acids Res. 2015, 43, 2466-2485. (57) Morais et al, In Vitro Cell. Dev. Biol. 1988, 24, 649-658.

Example 5

Figure 8:
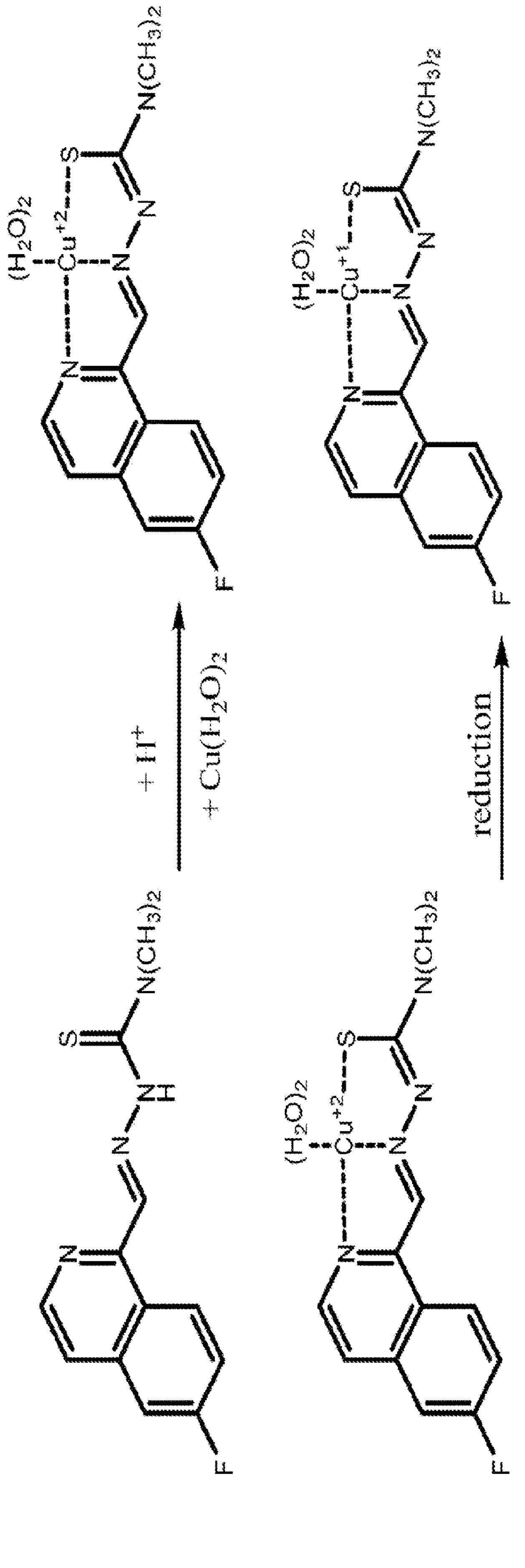
FIG. 8 shows the reduction of Cu(II) to Cu(I) for HCT13.

To elucidate potential contributing factors to compound HCT-13's potency, density functional theory (DFT) calculations were performed and the relative energies of formation and Cu(II) reduction were determined for selected ligand-Cu(II) complexes (Table 3). All calculations were performed with Gaussian 1614 using the B3LYP functional and the 6-31G(d) basis set. A correlation between IC90 value and energy of complex formation was found, with the latter consisting of ligand deprotonation and copper binding energies. HCT-5, which possesses an electron-donating substituent at the isoquinoline 6-position and was the least potent compound tested, bonded most weakly to Cu(II). Conversely, HCT-12 and HCT-13, which bear electron-withdrawing fluorine substituents at the 4- and 6-positions, respectively, bonded more strongly. HCT-11, which lacked isoquinoline substituents, had an energy of coordination to Cu(II) that was 4.0 kcal/mol lower than that of HCT-5. The ease of deprotonation in the thiosemicarbazone chain most strongly contributed to the trends observed in the energies of complex formation, where ligands with electron-withdrawing substituents had lower energies of deprotonation. The reduction of Cu(II) to Cu(I) was most exergonic in the Cu:HCT13 complex, indicating that this compounds is most readily capable of participating in redox process (FIG. 8).

TABLE 3

| Compound | Relative Deprotonation Energy | Relative Binding Energy | Relative Complexation Energies (kcal/mol) | Relative Energies of Reduction (kcal/mol) |
|---|---|---|---|---|
| HCT-5 | 0 | 0 | 0 | −0.9 |
| HCT-11 | −4.6 | 0.6 | −4 | 0 |
| HCT-12 | −9.6 | 4.3 | −5.5 | −1.5 |
| HCT-13 | −10.5 | 4.4 | −6.1 | −1.5 |

Example 6

Figure 2H:
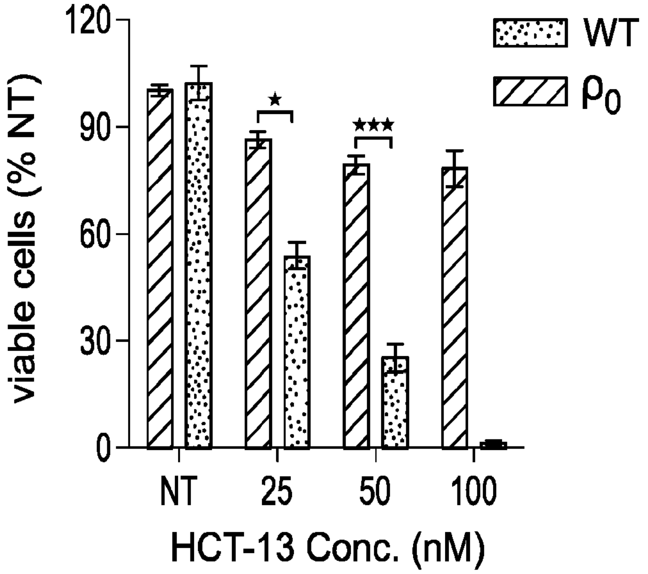
Figure 2I:
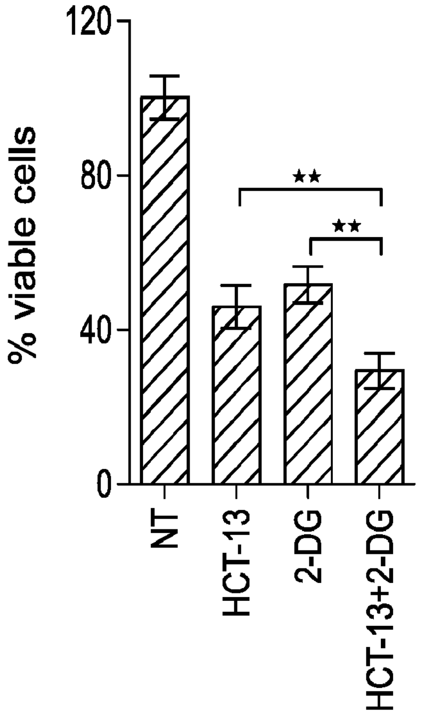
Figure 6A:
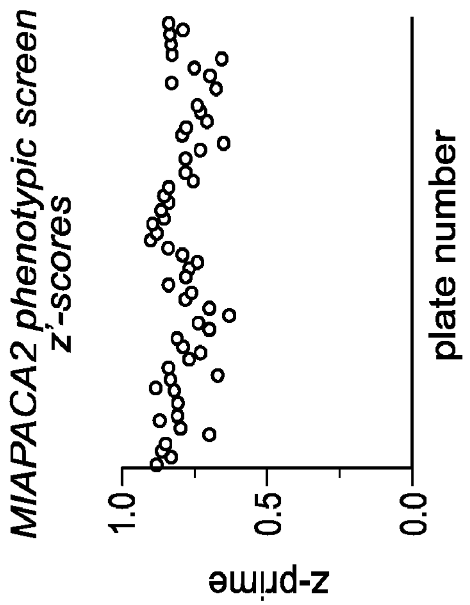
FIGS. 6A-6C provide the identification of resistance mechanisms to HCT13 using a synthetic lethality screen.
Figure 6B:
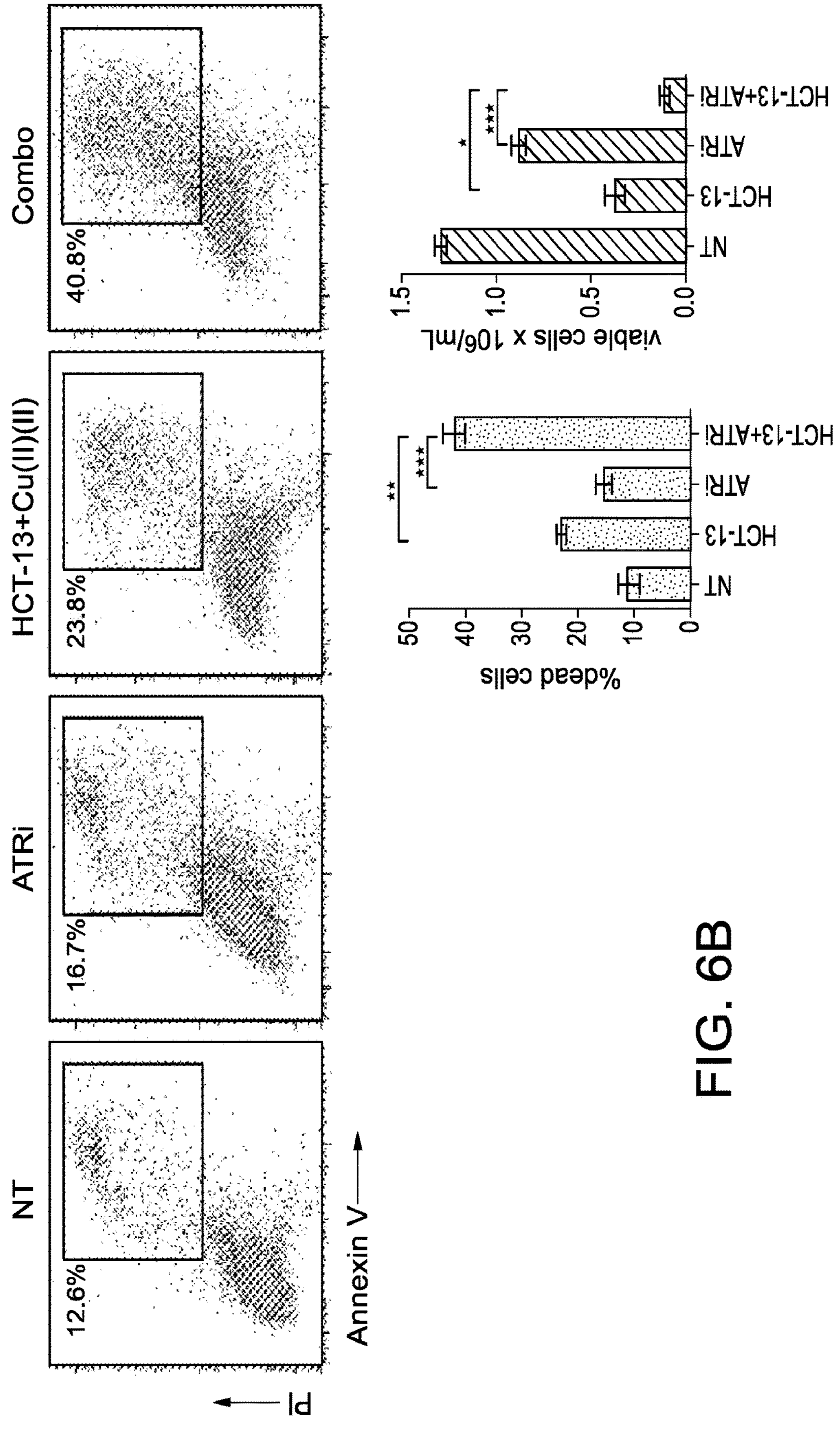
Figure 6C:
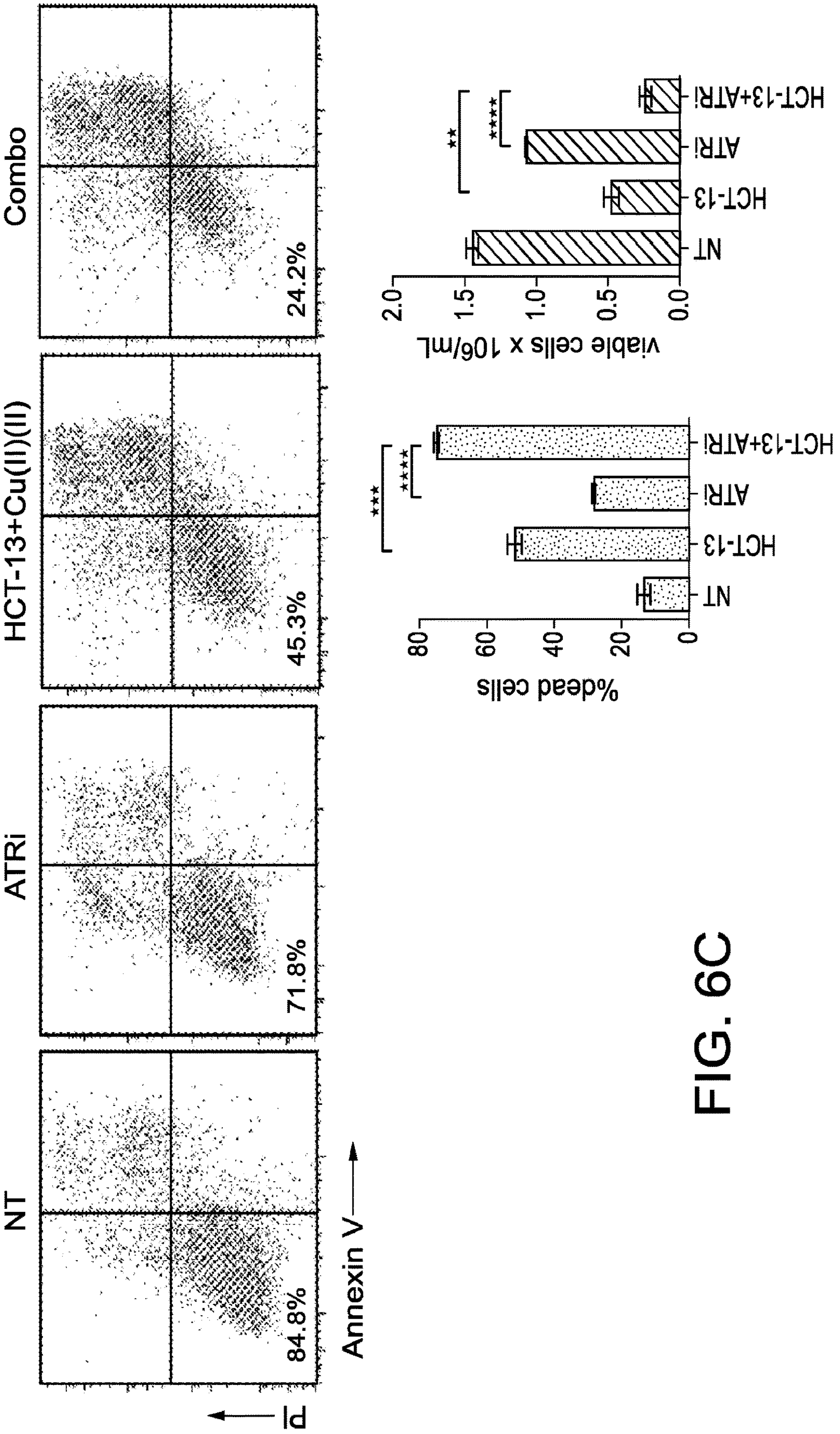

To determine whether the cytotoxicity of HCT-13 was ETC-dependent, its effects upon 143 BTK ρ0, a mitochondrial DNA (mtDNA)-deficient osteosarcoma cell line was examined. Compared to WT, the ρ0 cells were significantly less sensitive to the treatment (FIG. 2H), with a concurrent decrease in levels of S-phase arrest (FIG. 6C). These results indicate that HCT-13 preferentially targets tumor cells which rely more heavily upon OXPHOS than on glycolysis. To test this hypothesis, cells were treated with HCT-13 with and without 2-deoxyglucose (2-DG), a molecule that competitively inhibits glycolysis, thereby forcing cells to rely upon OXPHOS for energy production (FIG. 2I). (Dar et al, Sci. Rep. 2017, 7(1):8760). Co-administration of 2-DG significantly potentiated the activity of HCT-13, conceivably by forcing the cancer cells to rely more heavily upon OXPHOS which was in turn impaired by HCT-13.

Example 7

The in vivo efficacy and tolerability of HCT-13 was investigated. Two leukemia models were chosen—a primary murine BCR-ABL-expressing Arf-null pre-B (p185BCR-ABL Arf−/−) ALL model (p185) and a human systemic acute myeloid leukemia (AML) model (MV4-11)—as these leukemias possess aggressive phenotypes, have high intrinsic levels of OXPHOS, and there remains a persistent unmet need for effective therapeutic options, particularly in the case of AML. Both p185 and MV4-11 cell lines were engineered to express luciferase to monitor the systemic leukemic burden by bioluminescence imaging (BLI). (Boulos et al, Blood 2011, 117(13):3585-3595; Rahmani et al, Cancer Res. 2018, 78(11):3075-3086). To bypass the need for systemic copper supplementation, a one-to-one complex of copper and HCT-13 (i.e., HCT-16) was prepared for in vivo administration according to reported procedures for similar compounds and characterized by UV-HPLC and HR-MS. The in vitro antiproliferative activity of HCT-16 was consistent with that of HCT-13+Cu(II) in all cell lines tested.

Figure 9A:
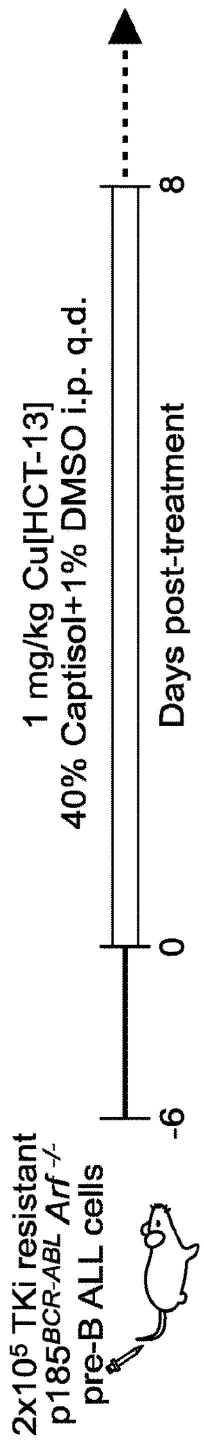
FIGS. 9A-9H show that HCT-16 is effective in aggressive models of systemic B-ALL and AML.
Figure 9B:
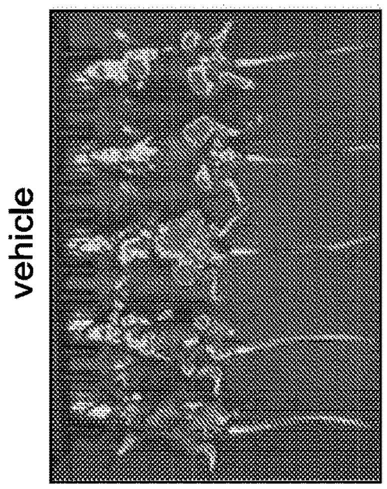
Figure 9C:
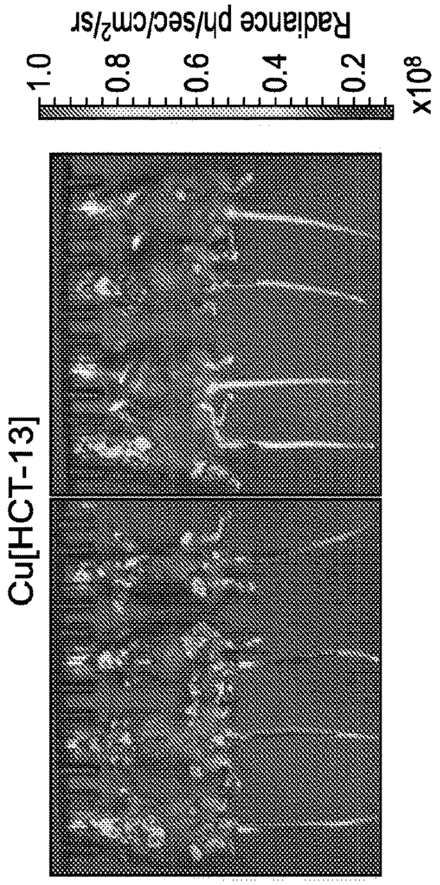
Figure 9D:
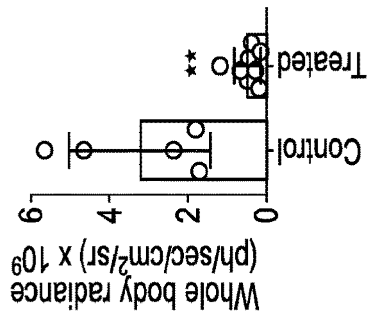
Figure 9E:
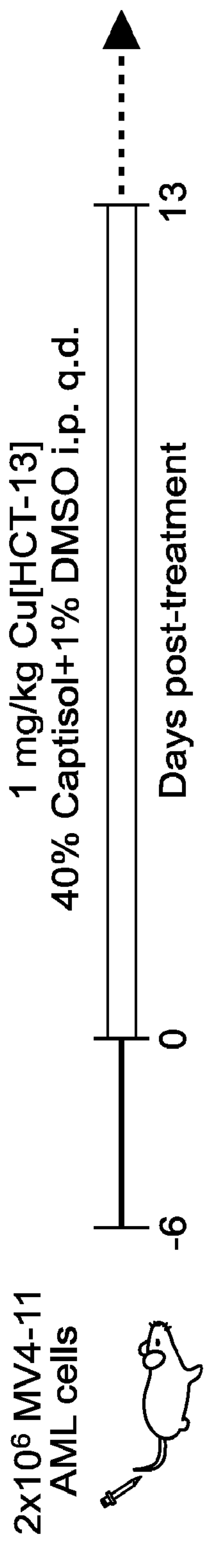
Figure 9F:
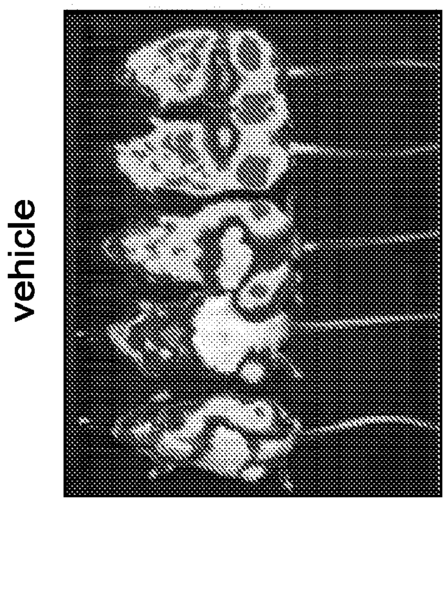
Figure 9G:
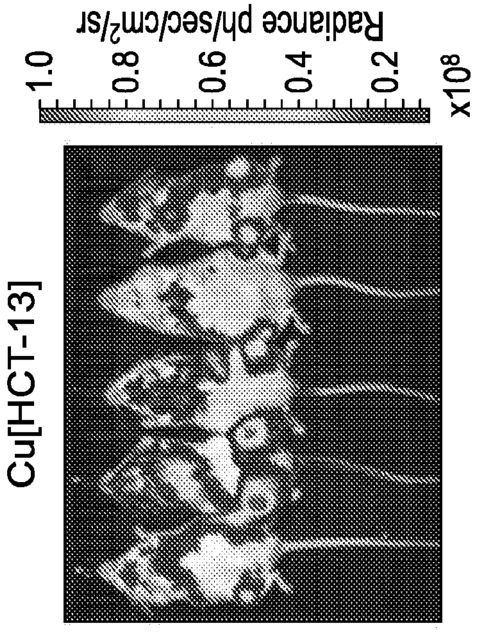
Figure 9H:
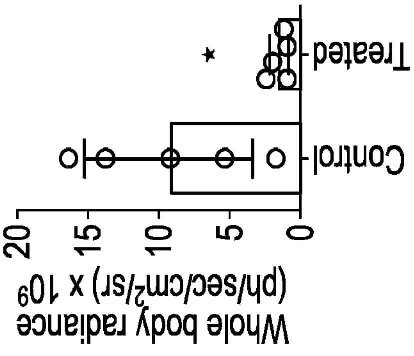

Treatment in both p185 and MV4-11 murine models was initiated on day six post-inoculation of cells, when all mice showed evidence of systemic disease. Mice in treatment groups of the pre-B ALL and AML arms of the study were administered 1 mg/kg HCT-16 q.d. for 8 and 13 days, respectively (FIGS. 9A, 9E). The treatment was well tolerated as indicated by body weight measurements. Fourteen days after treatment initiation in the pre-B ALL arm, HCT-13-treated mice displayed significantly lower systemic disease burden than mice in the control group (FIGS. 9A-9D). Similarly, treatment group mice in the MV4-11 portion of the study had significantly lower disease burden on day 19 compared to the control group mice (FIGS. 9F-9H).

Materials and Methods for Examples 1-8

Cell culture and culture conditions. Pancreatic adenocarcinoma cell lines: PATU8988T, MIAPACA2, SU8686, PSN1, HPAC, BXPC3, DANG, SUIT2, A13A, CAPAN2, T3M4, A2.1, HUPT4, XWR200, L36PL, YAPC, PANC0327, PANC1, PATU8902, HPAF11, ASPC1, PANC0813, PANC0203, HS766T, SW1990, and CFPAC1; prostate cancer cell lines: 22Rv1, LNCaP, RM1 and C4-2; and small cell lung carcinoma cell lines: NCI-H526, NCI-H146, and NCI-H1963 were obtained from American Type Culture Collection (ATCC). 143 BTK WT and 143 BTK $\rho_0$, BJ WT and BJ po cells were gifts from Prof. Michael Teitell in UCLA. Murine Prostate cancer cell lines MyC CaP was a kind gift from Prof. D L J Thorek at WUSTL. Murine Pancreatic cancer cells KP4662 was kind gift from Prof. Robert Vonderheide at UPenn. With a few exceptions, cell lines were cultured in DMEM (Corning) or RPMI (Corning) containing 10% fetal bovine serum (FBS, Omega Scientific) and were grown at 37° C., 20% $O_2$ and 5% $CO_2$. All cultured cells were incubated in antibiotic free media and were regularly tested for mycoplasma contamination using Myco-Alert kit (Lonza) following the manufacturer's instructions, except that the reagents were diluted 1:4 from their recommended amount.

HCT-13 stock solution. HCT-13 was solubilized up to a concentration of 20 mg/mL in an aqueous solution of 40% captisol with 1% DMSO with the aid of heating at 50° C. and sonication for 15 minutes.

Proliferation assay. Cells were plated in 384-well plates (500 cells/well for adherent cell lines in 30 µl volume). Drugs were serially diluted to the desired concentrations and an equivalent volume of DMSO was added to vehicle control. Following 72 h incubation, ATP content was measured using CellTiter-Glo reagent according to manufacturer's instructions (Promega, CellTiter-Glo Luminescent Cell Viability Assay), and analyzed by SpectraMax luminometer (Molecular Devices). $IC_{50}$ and $IC_{90}$ values, concentrations required to inhibit proliferation by 50% and 90% respectively compared to DMSO treated cells, were calculated using Prism 6.0 h (Graphpad Software). The 430-member protein kinase inhibitor library used for the chemical genomics screen was purchased from Selleckchem, Catalog No. L1200.

Western blot. Cells were lysed using RIPA buffer supplemented with protease (ThermoFisher, 78,430) and phosphatase (ThermoFisher, 78,420) inhibitors, scraped, sonicated, and centrifuged (20,000×g at 4° C.). Protein concentrations in the supernatant were determined using the Micro BCA Protein Assay kit (Thermo), and equal amounts of protein were resolved on pre-made Bis-Tris polyacrylamide gels (Life Technologies). Primary antibodies: pAMPK$_{T172}$ (Cell signaling, #2535, 1:1000), HO-1 (Cell signaling, #5061S, 1:1000), pS345 CHEK1 (Cell signaling, #2348L, 1:1000), pT68 CHEK2 (Cell signaling, #2197 S, 1:1000), pS139 H2A.X (Millipore, 05-636, 1:1000), clvd. Casp3 (Cell signaling, #9662, 1:1000), and anti-actin (Cell Signaling Technology, 9470, 1:10,000). Primary antibodies were stored in 5% BSA (Sigma-Aldrich) and 0.1% $NaN_3$ in TBST solution. Anti-rabbit IgG HRP-linked (Cell Signaling Technology, 7074, 1:2500) and anti-mouse IgG HRP-linked (Cell Signaling Technology, 7076, 1:2500) were used as secondary antibodies. Chemiluminescent substrates (ThermoFisher Scientific, 34,077 and 34,095) and autoradiography film (Denville) were used for detection.

Viability/Apoptosis assay. Viable cells were measured by Trypan blue staining using a Vi-Cell counter (Beckman Coulter, CA, USA). Apoptosis and cell death were assayed using Annexin V-FITC and PI according to manufacturer's instructions (FITC Annexin V Apoptosis Detection Kit, BD Sciences, #556570).

Cell cycle. Cell cycle was assessed using Propidium iodide staining at indicated timepoints. Cells were pulsed with EdU 1 h before collection at different time points. Cells were fixed 4% paraformaldehyde, permeabilized with perm/wash reagent (Invitrogen), stained with Azide-AF647 (using click-chemistry, Invitrogen; Click-iT EdU Flow cytometry kit, #C10634) and FxCycle-Violet (Invitrogen), and then analyzed by flow cytometry (a detailed description is available in the Supplementary Information).

ROS Measurements. Cellular ROS measurement was assayed with CM-$H_2$DCFDA staining after treatment according to manufacturer's instructions (Reactive Oxygen Species (ROS) Detection Reagents, Invitrogen, #D399). The cells were then incubated with 5 µM of CM-$H_2$DCFDA for 30 min, spun down at 450×g for 4 mins, and the supernatant was replaced with fresh media containing lethal compounds and/or Cu(II). Then, the cells were incubated for 30 mins, spun down, and the supernatant was replaced with PBS. The samples were analyzed using flow cytometry. Mitochondrial ROS was measured using MitoSOX staining according to manufacturer's instructions (MitoSOX, Invitrogen, #M36008). Cells were treated with HCT-13, washed and treated with MitoSOX. Cells were then incubated for 30 minutes at 37° C. After incubation, media is aspirated and cells are washed with PBS and analyzed by flow cytometry.

Mito Stress Test and Electron Flow Assay. All oxygen consumption rate (OCR) was measured using a XF24 Analyzer (Agilent) and normalized per μg protein. For cellular OCR, cells were incubated in unbuffered DMEM containing 25 mM glucose, 1 mM pyruvate and 2 mM glutamine. OCR was measured before (total respiration) and after the sequential injection of 1 μM oligomycin (complex V inhibitor), 0.75 μM FCCP (uncoupler), and 1 μM of rotenone and myxothiazol (complex I and III inhibitors, respectively), as described by Wu et al, Am. J. Physiol., Cell Physiol. 2007, 292(1):C125-C136. Mitochondrial respiration was calculated by subtracting the non-mitochondrial respiration left after rotenone and myxothiazol injection. Oligomycin-sensitive respiration represents ATP-linked respiration (coupled respiration).

To measure electron transport chain complex activity from cells, cells were incubated in MAS buffer with 10 mM pyruvate (complex I substrate), 2 mM malate, 4 μM FCCP, 4 mM ADP, and 1 nM of XF Plasma Membrane Permeabilizer (PMP) reagent (Agilent). OCR was measured before and after the sequential injection of 2 μM rotenone, 10 mM succinate (complex II substrate), 4 μM antimycin A (complex III inhibitor), and a mix of 10 mM ascorbate and 100 μM TMPD (complex IV substrates), as described by Vergnes, J. Clin. Endocrinol. Metab. 2016, 101(11):4440-4448. Antimycin A-sensitive respiration represents the complex III respiration.

To measure OCR directly from mitochondria, mitochondria were isolated from fresh mouse liver by dual centrifugation at 800 g and 8000 g and seeded by centrifugation. (Vergnes, J. Clin. Endocrinol. Metab. 2016, 101(11):4440-4448). Mitochondria were incubated with 1 mM pyruvate (complex I), 2 mM malate, 4 μM FCCP in MAS buffer, as well as the "corresponding drugs" for 30 min at 37° C. OCR was measured before and after the sequential injections described in the previous paragraph.

Intracellular Cu(II) measurement. Cells were plated in 6-well plates and cultured for one day. Vehicle of HCT-13 were added to the cells the following day and incubated for 24 hours. The plates were then washed 2 times with PBS containing 1 mM EDTA and 2 times with PBS alone. The concentration of Cu(II) was measured using Inductive Coupled Plasma Mass Spectrometry (ICP-MS) using standard procedure.

FACS analyses. All flow cytometry data were acquired on a five-laser LSRII cytometer (BD), and analyzed using the FlowJo software (Tree Star).

Isotopic labeling in cell culture. Cells were transferred into DMEM without glucose and supplemented with 10% dialyzed FBS (Gibco) containing [U-13C6]glucose (Sigma-Aldrich, 389374) at 11 mM. The cells were incubated for 48 h before sample collection and processing as described by Le et al, Nature Communications 2017, 8(1):1-14.

Animal studies. Mice were housed under specific pathogen-free conditions and were treated in accordance with UCLA Animal Research Committee protocol guidelines. All C57BL/6 female mice were purchased from the UCLA Radiation Oncology breeding colony. All NCG female mice were purchased from the Jackson Labs (JAX).

In vivo leukemia models and treatment regimens. All animal studies were approved by the UCLA Animal Research Committee (ARC). For development of systemic murine B ALL model, C57Bl/6 female mice were injected intravenously with 200,000 firefly luciferase expressing p185BCR-ABL Arf−/− pre-B-ALL cells (gifted by Dr. Nidal Boulos and the CERN Foundation). (Boulos, et al, Blood 2011, 117(13):3585-3595; Nathanson et al, J. Exp. Med. 2014, 211(3):473-486). For development of the systemic human AML model, NCG female mice (from Jackson Labs) were injected intravenously with 5×106 firefly luciferase expressing MV4-11 cells. (Jacque et al, Blood, 2015, 126 (11):1346-1356). The leukemic burden was monitored using bioluminescence imaging. All Cu[HCT-13] treatments were performed using a formulation consisting of 40% Captisol and 1% DMSO. The treatments were performed by intraperitoneal (i.p.) injections using 100 μL volume daily.

Example 8

All chemicals, reagents and solvents were obtained from commercial sources and were used without further purification. Unless otherwise noted, reactions were carried out in oven-dried glassware under an atmosphere of argon using commercially available anhydrous solvents. Tetrahydrofuran (THF) was distilled from sodium under an argon atmosphere. Dichloromethane was distilled from calcium hydride. Solvents used for extractions and chromatography were not anhydrous. Analytical TLC was carried out on precoated silica gel (Merck silica gel 60, F254) and visualized with UV light. Column chromatography was performed with silica (Fisher, 230-400 mesh). $^{1}H$ NMR, $^{13}C$ NMR, and $^{19}F$ NMR spectra were measured in CDCl3 or DMSO-d6 on Bruker AV spectrometers at 400 or 500 MHz. Chemical shifts were reported in parts per million (ö) relative to residual solvent signals. The signals observed were described as follows: s (singlet), d (doublet), t (triplet), q (quartet), dd (doublet of doublets), dt (doublet of triplets), ddd (doublet of doublet of doublets), tt (triplet of triplets), tdd (triplet of doublet of doublets), m (multiplet), br s (broad singlet). Mass spectra were obtained on a Waters LCT Premier with ACQUITY UPLC mass spectrometer under electrospray ionization (ESI) or Thermo Fisher Scientific Exactive Plus with direct analysis in real time (DART) ionization. Purity of all compounds used in biological assays was determined on a Hewlett Packard 1090 HPLC system using an Aquasil C18 column (250 mm×2 mm, 5 μm, Keystone Scientific) with an acetonitrile/water solvent system containing 0.1% TFA with detection performed at 254 nm. HPLC purification was performed on a Hewlett Packard 1090 HPLC system with Hypersil Gold column (250 mm×10 mm, 5 μm, Thermo Scientific) with and acetonitrile/water solvent system containing 0.05% formic acid and 10 mM ammonium formate. All microwave-assisted reactions were carried out in a CEM Discover 908005 Microwave synthesizer system.

Isoquinoline-1-carboxaldehyde (S1)

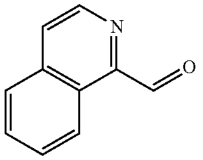 [SMILES: O=Cc1nccc2ccccc12]

To a solution of 1-methylisoquinoline (1.0 g, 6.98 mmol) in 1,4-dioxane (10 mL) was added selenium dioxide (0.930 g, 8.38 mmol) and the mixture was refluxed for 4 h. The mixture was filtered, then concentrated in vacuo. The crude residue was purified by column chromatography (25% DCM:Hexanes) to give the product S1 as a taupe powder (0.840 g, 69% yield). $^{1H}$ NMR (500 MHz, DMSO-d6) ö 10.28 (s, 1H), 9.15 (ddd, J=7.7, 1.9, 0.8 Hz, 1H), 8.82 (d, J=5.5 Hz, 1H), 8.21 (dd, J=5.6, 0.9 Hz, 1H), 8.17-8.12 (m, 1H), 7.93-7.84 (m, 2H). $^{13}$C NMR (125 MHz, DMSO-d6) ö 195.64, 149.38, 142.47, 136.49, 131.00, 130.30, 127.45, 125.77, 125.41, 124.73. DART-MS: m/z calcd. for C10H8NO $(M+H)^+$ 158.06004. found 158.05977.

(E)-2-(isoquinolin-1-ylmethylene)hydrazine-1-carbothioamide (HCT1)

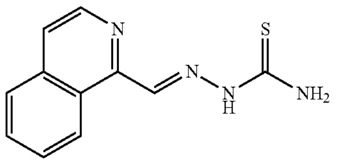 [SMILES: NC(=S)N/N=C/c1nccc2ccccc12]

Synthesized from S1 as previously reported.1 $^{1}$H NMR (500 MHz, DMSO-d6) ö 11.74 (s, 1H), 9.19 (d, J=8.5 Hz, 1H), 8.60-8.54 (m, 2H) 8.49 (br s, 1H), 8.02 (d, J=8.1 Hz, 1H), 7.86 (d, J=5.6 Hz, 1H), 7.84-7.78 (m, 2H), 7.75 (ddd, J=8.3, 6.8, 1.4 Hz, 1H). $^{13}$C NMR (125 MHz, DMSO-d6) ö 178.41, 150.78, 145.99, 142.13, 136.24, 130.47, 129.08, 127.22, 126.94, 125.58, 121.77. DART-MS: m/z calcd. for C11H10N4S $(M+H)^+$ 231.06989. found 231.06938.

(E)-2-(isoquinolin-1-ylmethylene)-N-methylhydrazine-1-carbothioamide (HCT6)

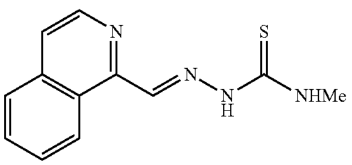 [SMILES: CNC(=S)N/N=C/c1nccc2ccccc12]

To a solution of S1 (0.060 g, 0.382 mmol) in ethanol (3 mL) was added 4-methyl-3-thiosemicarbazide (0.040 g, 0.382 mmol) and HCl (0.318 mL, 12 M in H2O). The mixture was refluxed for 4 h. The solid that formed was collected by filtration, washed with water, and recrystallized from EtOH to yield HCT6 as a yellow powder (0.058 g, 62% yield). $^{1}$H NMR (500 MHz, DMSO-d6) ö 11.78 (br s, 1H), 9.11 (br s, 1H), 8.61 (s, 1H), 8.56 (d, J=5.6 Hz, 1H), 8.31 (br s, 1H), 8.02 (d, J=8.1 Hz, 1H), 7.89-7.79 (m, 2H), 7.76 (t, J=7.7 Hz, 1H), 3.07 (s, 3H). $^{13}$C NMR (125 MHz, DMSO-d6) ö 178.36, 151.06, 144.76, 142.15, 136.25, 130.42, 128.86, 127.21, 126.82, 125.64, 121.48, 31.34. DART-MS: m/z calcd. for C12H13N4S $(M+H)^+$ 245.08554. found 245.08505.

(E)-2-(Isoquinolin-1-ylmethylene)-N,N-dimethylhydrazine-1-carbothioamide and (Z)-2-(Isoquinolin-1-ylmethylene)-N,N-dimethylhydrazine-1-carbothioamide (HCT11), Respectively

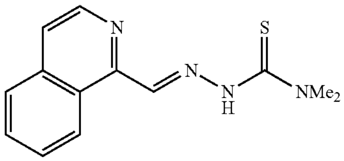

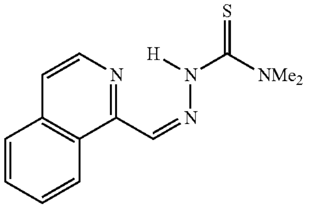

To a solution of S1 (0.060 g, 0.382 mmol) in ethanol (3 mL) was added 4,4-dimethyl-3-thiosemicarbazide (0.046 g, 0.382 mmol) and HCl (0.318 mL, 12 M in H2O). The mixture was refluxed for 4 h. The solid that formed was collected by filtration, washed with water, and recrystallized from EtOH to yield HCT11 as a yellow powder (0.056 g, 57% yield) (mixture of E and Z isomers). $^{1}$H NMR (500 MHz, DMSO-d6) ö 15.99 (s, 0.33H), 11.26 (br s, 1H), 9.77 (dd, J=8.8, 5.1 Hz, 1H), 8.81 (d, J=8.6 Hz, 0.33H), 8.70 (d, J=1.7 Hz, 1H), 8.69 (d, J=1.2 Hz, 0.33H), 8.63 (s, 0.33H), 8.55 (d, J=5.5 Hz, 1H), 8.12 (d, J=8.2 Hz, 0.33H), 8.01-7.96 (m, 1.33H), 7.92 (ddd, J=8.1, 7.0, 1.1 Hz, 0.33H), 7.88-7.76 (m, 2.33H), 7.72 (ddd, J=8.4, 6.8, 1.4 Hz, 1H), 3.43 (s, 1.98H), 3.35 (s, 6H). 13C NMR (125 MHz, DMSO-d6) ö 180.88, 180.81, 151.94, 150.58, 147.81, 142.50, 140.45, 136.86, 136.82, 131.80, 130.77, 129.48, 129.16, 128.21, 128.17 (2C), 127.68, 126.83, 125.87, 125.60, 122.53, 121.93, 42.08 (4C). DART-MS: m/z cald. For H13H15N4S (M+H_+259.10119. found 259.10080.

1-Methyl-5-nitroisoquinoline (S2)

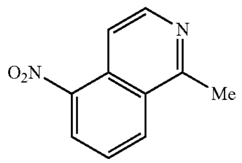 [SMILES: Cc1nccc2c([N+](=O)[O-])cccc12]

To a solution of 1-methylisoquinoline (28.80 g, 201.2 mmol) in sulfuric acid (92.4 mL) at 0° C. was added KNO3 (20.4 g, 201.2 mmol) in sulfuric acid (78.0 mL). The mixture was heated at 60° C. for 2 h and then poured slowly over crushed ice. The solution was made alkaline with NH4OH; the resulting tan precipitate was filtered, washed with water, and dried to afford S2 as a tan solid (20.00 g, 53%). $^{1}$H NMR (500 MHz, CDCl3) ö 8.61 (d, J=6.2 Hz, 1H), 8.47-8.50 (m, 2H), 8.28 (d, J=6.3 Hz, 1H), 7.71 (t, J=8.1 Hz, 1H), 3.05 (s, 3H). $^{13}$C NMR (125 MHz, CDCl3) ö 159.53, 145.38, 132.53, 128.65, 128.23, 127.79, 125.58, 114.26 (2C), 23.38. DART-MS: m/z calcd. for C10H9N2O2 $(M+H)^+$ 189.06585. found 189.06544.

1-Methylisoquinolin-5-amine (S3)

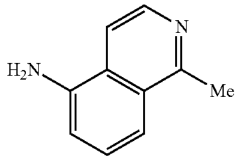

To a solution of S2 (20.00 g, 106.28 mmol) in MeOH (530 mL) and iron powder (44.40 g, 795.05 mmol) was added concentrated HCl (1 mL, 12 M in H2O). The mixture was refluxed for 2 h and then a solution of sodium hydroxide (6 mL, 2 M in H2O) was added. The mixture was filtered, then concentrated in vacuo, and resuspended in EtOAc (200 mL) and water (200 mL). The organic layer was separated and the aqueous layer was extracted with EtOAc (3×200 mL). The organic layers were combined and dried over Na2SO4, filtered, and then concentrated in vacuo. The crude residue was purified by flash column chromatography (gradient, 10-30% EtOAc:hexanes). The isoquinoline S3 was obtained as a brown solid (15.0 g, 90%). $^{1}$H NMR (500 MHz, CDCl3) ö 8.36 (d, J=6.1 Hz, 1H), 7.55 (dt, J=8.4, 1.0 Hz, 1H), 7.45 (d, J=5.7 Hz, 1H), 7.39 (dd, J=8.5, 7.4 Hz, 1H), 6.95 (dd, J=7.5, 0.9 Hz, 1H), 4.18 (br s, 2H), 2.93 (s, 3H). $^{13}$C NMR (125 MHz, CDCl3) ö 165.39, 159.15, 141.94, 128.35, 127.51, 126.16, 116.19, 113.09, 112.73, 23.06. DART-MS: m/z calcd. for C10H11N2 $(M+H)^+$ 159.09167. found 159.09136.

tert-Butyl (tert-butoxycarbonyl)(1-methylisoquinolin-5-yl)carbamate (S4)

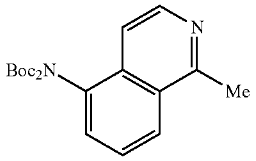

To a solution of S3 (360.0 mg, 2.28 mmol) in THF (10 mL) was added Boc2O (1.68 g, 6.83 mmol), DMAP (28.0 mg, 0.23 mmol), and TEA (0.69 g, 3.65 mmol) and the mixture was stirred at 22° C. overnight. The reaction was quenched with water (10 mL) and the organic layers were separated. The aqueous layer was extracted with EtOAc (3×10 mL). The organic layers were combined and dried over Na2SO4, filtered, and then concentrated in vacuo. The crude residue was purified by flash column chromatography (gradient, 10-30% EtOAc:hexanes). The isoquinoline S4 was obtained as a brown solid (420.0 mg, 51%). $^{1}$H NMR (500 MHz, CDCl3) ö 8.43 (d, J=6.0 Hz, 1H), 8.11 (d, J=8.5 Hz, 1H), 7.58 (t, J=7.9 Hz, 1H), 7.51 (dd, J=7.3, 1.1 Hz, 1H), 7.46 (d, J=5.9 Hz, 1H), 2.99 (s, 3H), 1.31 (s, 18H). $^{13}$C NMR (125 MHz, CDCl3) ö 159.16, 151.59, 142.73, 135.74, 133.82, 129.64, 128.20, 126.55, 125.86, 113.74, 83.19 (2C), 27.90 (6C), 22.90. DART-MS: m/z calcd. for C20H27N2O4 $(M+H)^+$ 359.19653. found 359.19540.

tert-Butyl (1-methylisoquinolin-5-yl)carbamate (S5)

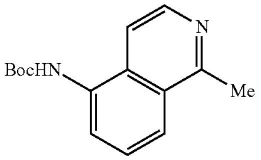 [SMILES: Cc1nccc2c(NC(=O)OC(C)(C)C)cccc12]

To a solution of S3 (10.00 g 63.21 mmol) in THF (250 mL) was added Boc2O (34.38 g, 158.0 mmol), DMAP (772.2 mg, 6.32 mmol), and TEA (15.96 g, 158.0 mmol) and the mixture was stirred at 22° C. overnight. After completion of the reaction as judged by TLC, $NaHCO_3$ (15.93 g, 189.6 mmol) and MeOH (100 mL) were added to the reaction mixture and it was refluxed overnight. After completion of the reaction (monitored by TLC), the mixture was concentrated in vacuo and then resuspended in EtOAc (200 mL) and water (200 mL). The organic layer was separated and the aqueous layer was extracted with EtOAc (3×200 mL). The organic layers were combined and dried over Na2SO4, filtered, and then concentrated in vacuo. The crude residue was purified by flash column chromatography (gradient, 10-30% EtOAc:hexanes). The isoquinoline S5 was obtained as a brown oil (4.73 g, 29%). $^{1}$H NMR (500 MHz, CDCl3) ö 8.37 (d, J=6.1 Hz, 1H), 7.56 (dt, J=8.3, 1.0 Hz, 1H), 7.46 (d, J=6.7 Hz, 1H), 7.40 (dd, J=8.5, 7.4 Hz, 1H), 6.95 (dd, J=7.5, 0.9 Hz, 1H), 2.94 (s, 4H), 1.56 (s, 9H). 13C NMR (125 MHz, CDCl3) ö 165.39, 159.15, 141.94, 128.35, 127.51, 126.16, 116.19, 113.09, 112.73, 76.91, 29.86 (3C), 23.06, one low-field carbon were either not observed or is overlapping with another low-field carbon. DART-MS: m/z calcd. for $C_{15}H_{19}N_2O_2$ $(M+H)^+$ 259.14410. found 259.14349.

tert-Butyl methyl(1-methylisoquinolin-5-yl)carbamate (S6)

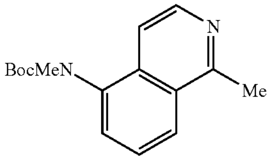

To a solution of S5 (1.99 g, 7.68 mmol) in THF (50 mL) was added NaH 60% in mineral oil (399.6 mg, 9.99 mmol). After effervescence ceased, the resulting solution was refluxed for 30 min. To the reaction mixture was then added MeI (622 μL, 9.99 mmol) in THF (2 mL) and the solution was subsequently refluxed overnight. The mixture was concentrated in vacuo and the crude residue was purified by flash column chromatography (gradient, 10-30% EtOAc: hexanes). The isoquinoline S6 was obtained as an amber oil (4.73 g, 29%). $^{1}$H NMR (500 MHz, CDCl3) ö 8.42 (d, J=6.0 Hz, 1H), 8.08 (d, J=8.4 Hz, 1H), 7.46-7.61 (m, 3H), 3.31 (s, 3H), 3.01 (s, 3H), 1.23 (s, 9H). $^{13}$C NMR (125 MHz, CDCl3) ö 159.01, 155.21, 140.21, 133.54, 128.35, 126.95, 124.96, 121.52, 114.65, 76.15, 29.71, 28.06 (3C), 22.51, one low-field carbon were either not observed or is overlapping with another low-field carbon. DART-MS: m/z calcd. for $C_{16}H_{21}N_2O_2$ $(M+H)^+$ 273.15975. found 273.15891.

tert-Butyl (1-formylisoquinolin-5-yl)(methyl)carbamate (S7)

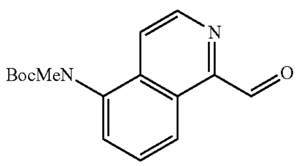

To a solution of S6 (1.50 g, 5.51 mmol) in 1,4-dioxane (60 mL) was added SeO2 (1.22 g, 11.0 mmol). The mixture was stirred at 60° C. overnight then cooled to 22° C. The mixture was concentrated in vacuo and the crude residue was purified by flash column chromatography (gradient, 5-25% EtOAc:hexanes). The isoquinoline S7 was obtained as a white solid (711.9 mg, 45%). $^1$H NMR (500 MHz, CDCl3) ö 10.39, 9.28 (d, J=8.6 Hz, 1H), 8.80 (d, J=5.7 Hz, 1H), 7.88 (d, J=5.1 Hz, 1H), 7.74 (d, J=8.0 Hz, 1H), 7.61 (m, 1H), 3.33 (s, 3H), 1.22 (s, 9H). $^{13}$C NMR (125 MHz, CDCl3) ö 195.44, 155.05, 150.18, 142.85, 139.95, 134.55, 129.90, 128.96, 127.08, 124.99, 120.65, 80.72, 37.85, 28.08 (3C). DART-MS: m/z calcd. for C16H19N2O3 $(M+H)^+$ 287.13902. found 287.13812.

tert-Butyl (tert-butoxycarbonyl)(1-formylisoquinolin-5-yl)carbamate (S8)

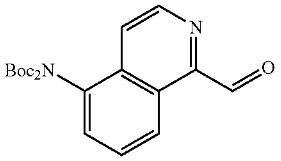

To a solution of S4 (200.0 mg, 0.558 mmol) in 1,4-dioxane (5.5 mL) was added SeO2 (123.8 mg, 1.12 mmol). The mixture was stirred at 60° C. overnight then cooled to 22° C. The mixture was concentrated in vacuo and the crude residue was purified by flash column chromatography (gradient, 5-25% EtOAc:hexanes). The isoquinoline S8 was obtained as a white solid (63.2 mg, 30%). $^1$H NMR (500 MHz, CDCl3) ö 10.40 (s, 1H), 9.34 (dt, J=8.7, 1.0 Hz, 1H), 8.81 (d, J=5.7 Hz, 1H), 7.89 (dd, J=5.7, 1.0 Hz, 1H), 7.76 (dd, J=8.7, 7.4 Hz, 1H), 7.61 (dd, J=7.3, 1.1 Hz, 1H), 1.32 (s, 18H). $^{13}$C NMR (125 MHz, CDCl3) δ 195.59, 151.36, 150.23, 143.31, 134.94, 130.49, 129.74, 126.88, 126.00, 119.90, 83.60 (2C), 27.91 (6C), two low-field carbon were either not observed or is overlapping with another low-field carbon. DART-MS: m/z calcd. for C20H25N2O5 $(M+H)^+$ 373.17580. found 373.17496

(E)-2-((5-(Methylamino)isoquinolin-1-yl)methylene) hydrazine-1-carbothioamide (HCT4)

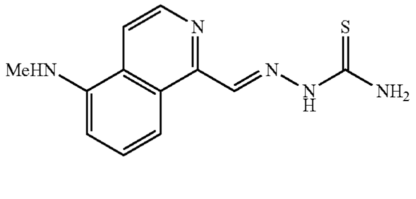 [SMILES: CNc1cccc2c(/C=N/NC(N)=S)nccc12]

To a solution of S7 (100.0 mg, 0.3492 mmol) in EtOH (1.75 mL) was added thiosemicarbazide (31.8 mg, 0.3492 mmol) and HCl (350 μL, 6 M in H2O). The mixture was stirred and refluxed for 1.5 h and then cooled to 22° C. The hydrochloride salt that formed was neutralized with 1.4 mL of a saturated aqueous $NaHCO_3$ solution. The precipitate of the desired compound was collected by filtration, washed with water, EtOH and then dried to yield the isoquinoline HCT4 as a black solid (622.4 mg, 97%). $^1$H NMR (500 MHz, DMSO-d6) δ 12.32 (s, 1H), 9.07 (br s, 1H), 8.92 (s, 1H), 8.90 (s, 1H), 8.57 (d, J=6.6 Hz, 1H), 8.52 (d, J=6.7 Hz, 1H), 7.85 (t, J=8.2 Hz, 1H), 7.56 (d, J=8.3 Hz, 1H), 7.30 (br s, 1H), 7.01 (d, J=8.0 Hz, 1H), 2.91 (s, 3H). $^{13}$C NMR (125 MHz, DMSO-d6) δ 179.40, 146.25, 146.00, 133.09, 130.09, 128.72, 126.75 (2C), 119.38, 111.17, 110.66, 30.39. DART-MS: m/z calcd. for C12H14N5S $(M+H)^+$ 260.09644, found 260.09501.

E)-N-Methyl-2-((5-(methylamino)isoquinolin-1-yl) methylene)hydrazine-1-carbothioamide and (Z)—N-Methyl-2-((5-(methylamino)isoquinolin-1-yl)methylene)hydrazine-1-carbothioamide (HCT9), Respectively

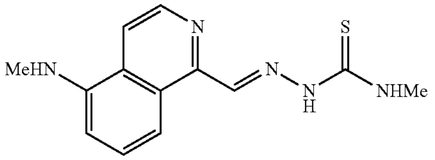

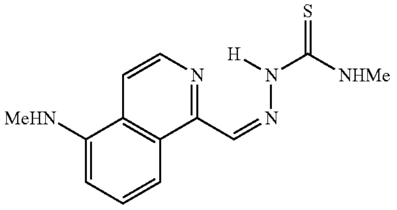

To a solution of S7 (51.4 mg, 0.18 mmol) in EtOH (0.88 mL) was added 4-methyl-3-thiosemicarbazide (18.9 mg, 0.18 mmol) and HCl (0.18 mL, 6 M in H2O). The mixture was stirred and refluxed for 1.5 h then cooled to 22° C. The hydrochloride salt that formed was neutralized with saturated aqueous $NaHCO_3$ solution (0.88 mL). The precipitate of the desired compound was collected by filtration, washed with water, EtOH and then dried to yield the isoquinoline HCT9 as a black solid (49.0 mg, 94%) (mixture of E and Z isomers). $^{1H}$ NMR (500 MHz, DMSO-d6) δ 14.74 (s, 0.15H), 12.22 (s, 1H), 9.39 (br s, 1H), 8.93 (q, J=4.7 Hz, 0.15H), 8.78 (s, 1H), 8.54 (d, J=5.9 Hz, 0.15H), 8.50 (d, J=6.5 Hz, 1H), 8.38 (s, 1H), 8.17 (s, 0.15H), 8.12 (d, J=5.9 Hz, 0.15H), 7.82 (d, J=8.6 Hz, 0.15H), 7.76 (t, J=8.1 Hz, 1H), 7.69 (s, 1H), 7.56 (t, J=8.1 Hz, 0.15H), 7.08 (br s, 1H), 6.92 (d, J=7.7 Hz, 1.15H), 6.72 (d, J=7.8 Hz, 0.15H), 3.07 (d, J=4.6 Hz, 3H), 3.02 (d, J=4.6 Hz, 0.45H), 2.88 (s, 3H), 2.86 (s, 0.45H). $^{13}$C NMR (125 MHz, DMSO-d6) δ 178.84, 178.38, 150.11, 147.37, 145.83 (2C), 145.56, 138.94, 132.45, 130.58, 129.19, 128.23, 128.22, 126.87 (2C), 126.80, 118.47, 117.04, 111.57, 110.13, 109.63, 106.57, 31.59, 31.42, 30.42 (2C). DART-MS: m/z calcd. For C13H16N5S (M+H)+274.11209. found 274.11104.

(E)-2-((5-Aminoisoquinolin-1-yl)methylene)hydrazine-1-carbothioamide (HCT5)

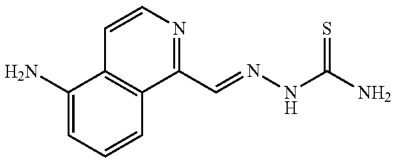 [SMILES: NC(=S)N/N=C/c1nccc2c(N)cccc12]

To a solution of S8 (30.0 mg, 0.081 mmol) in EtOH (0.39 mL) was added thiosemicarbazide (7.3 mg, 0.802 mmol) and HCl (80.6 j.tL, 6 M in H2O). The mixture was stirred and refluxed for 1.5 h then cooled to 22° C. The hydrochloride salt that formed was neutralized with saturated aqueous $NaHCO_3$ solution (0.39 mL). The precipitate of the desired compound was collected by filtration, washed with water, EtOH and then dried to yield the isoquinoline HCT5 as a green solid (19.6 mg, 99%). $^1$H NMR (500 MHz, DMSO-d6) ö 11.66 (br s, 1H), 8.57 (s, 1H), 8.42 (d, J=5.8 Hz, 1H), 8.31 (br s, 1H), 8.25 (d, J=8.5 Hz, 1H), 7.98 (d, J=5.8 Hz, 1H), 7.60 (br s, 1H), 7.42 (t, J=8.1 Hz, 1H), 6.89 (d, J=7.1 Hz, 1H), 6.02 (s, 2H). $^{13}$C NMR (125 MHz, DMSO-d6) ö 178.46, 150.36, 145.86, 144.62, 140.01, 129.74, 126.78, 125.83, 116.50, 113.12, 110.74. DART-MS: m/z calcd. for C11H11N5S (M+H) 246.08079. found 246.08020.

2-((5-Aminoisoquinolin-1-yl)methylene)-N-methylhydrazine-1-carbothioamide and (Z)-2-((5-Aminoisoquinolin-1-yl)methylene)-N-methylhydrazine-1-carbothioamide (HCT10)

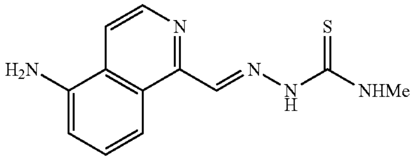

and

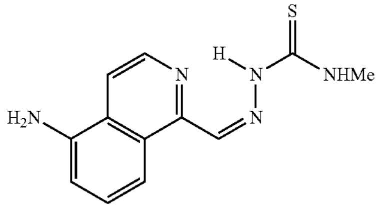

To a solution of S8 (27.1 mg, 0.0728 mmol) in EtOH (0.73 mL) was added 4-methyl-3-thiosemicarbazide (7.7 mg, 0.0732 mmol) and HCl (72.8 μL, 6 M in H2O). The mixture was stirred and refluxed for 1.5 h then cooled to 22° C. The hydrochloride salt that formed was neutralized with saturated aqueous $NaHCO_3$ solution (0.73 mL). The precipitate of the desired compound was collected by filtration, washed with water, EtOH and then dried to yield the isoquinoline HCT10 as a yellow solid (5.1 mg, 27%) (mixture of E and Z isomers). $^{1H}$ NMR (500 MHz, DMSO-d6) ö14.80 (s, 0.08H), 11.66 (br s, 1H), 8.95 (d, J=4.9 Hz, 0.08H), 8.62 (s, 1H), 8.52 (d, J=5.9 Hz, 0.8H), 8.42 (d, J=5.8 Hz, 1H), 8.25 (d, J=3.3 Hz, 1H), 8.18 (s, 0.08H), 8.11-8.15 (m, 1.08H), 7.99 (d, J=5.9 Hz, 1H), 7.83 (d, J=8.4 Hz, 0.08H), 7.48 (t, J=7.9 Hz, 0.08H), 7.43 (t, J=8.0 Hz, 1H), 6.97 (d, J=7.6 Hz, 0.08H), 6.91 (dd, J=7.6, 0.9 Hz, 1H), 6.21 (s, 0.16H), 6.04 (s, 2H), 3.05-3.07 (m, 3.24H). $^{13}$C NMR (125 MHz, DMSO-d6) ö 178.85, 178.52, 150.83, 150.19, 145.53, 145.20, 145.10, 140.49, 138.40, 130.28, 130.10, 129.16, 128.41, 127.36, 126.27, 126.16, 117.81, 116.96, 113.24, 111.66, 111.18, 110.61, 31.74, 31.59. DART-MS: m/z calcd. for C12H14N5S $(M+H)^+$ 260.09644. found 260.09563.

4-Fluoro-1-methylisoquinoline (S9)

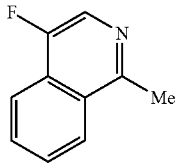

To a solution of 4-fluoroisoquinoline (1.50 g, 10.19 mmol) in THF (102 mL) was added allyl chloroformate (2.17 mL, 20.38 mmol). MeMgBr (10.19 mL, 2 M in diethyl ether) was then added dropwise to the reaction mixture at 0° C. with stirring. The reaction mixture was gradually warmed to 22° C. over a period of 2 h. The mixture was quenched with saturated aqueous $NH_4Cl$ (10 mL) and water (100 mL) was added. The organic layer was separated and the aqueous layer was extracted with EtOAc (3×100 mL). The organic layers were combined and dried over MgSO4, filtered, and then concentrated in vacuo. The crude residue in EtOAc was filtered through a silica plug, concentrated in vacuo and the residue was subjected to the next reaction without further purification. To a solution of the crude residue and Pd(PPh3)4 (70.1 mg, 0.061 mmd) in DCM (60 mL) at 0° C. was added morpholine (523.1 uL, 6.07 mmol). The reaction mixture was stirred and slowly warmed to 22° C. over a period of 3 h. The mixture was cooled to 0° C. and DDQ (1.38 g, 6.07 mmd) was added in portions. After the reaction mixture stirred at 0° C. for 30 min, the reaction was slowly poured into a solution of saturated $NaHCO_3$ solution (60 mL) and extracted with DCM (3×60). The combined extracts are washed with brine, dried over Na2SO4, and concentrated in vacuo. The crude residue was purified by flash column chromatography (gradient, 5-25% EtOAc: hexanes). The isoquinoline S9 was obtained as a brown oil (241.9 mg, 15% over three steps). $^1$H NMR (500 MHz, CDCl3) ö 8.23 (d, J=1.7 Hz, 1H), 8.06-8.09 (m, 2H), 7.73-7.76 (m, 1H), 7.64-7.67 (m, 1H), 2.90 (s, 3H). $^{13}$C NMR (125 MHz, CDCl3) ö 154.48 (d, $^1$JC-F=257.5 Hz), 154.24 (d, $^3$JC-F=4.9 Hz), 130.14 (d, $^4$JC-F=1.6 Hz), 128.35 (d, $^4$JC-F=2.4 Hz), 127.83, 126.64 (d, $^2$JC-F=15.3 Hz), 126.57 (d, $^2$JC-F=22.3 Hz), 125.60 (d, $^4$JC-F=2.1 Hz), 120.09 (d, $^3$JC-F=4.5 Hz), 22.10. $^{19}$F NMR (376 MHz, CDCl3) ö −143.11, extraneous peak found at −139.82. DART-MS: m/z calcd. for C10H9FN $(M+H)^+$ 162.07135. found 162.07092.

4-Fluoroisoquinoline-1-carboxaldehyde (S10)

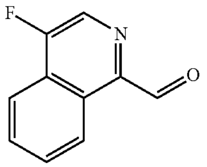 [SMILES: O=Cc1ncc(F)c2ccccc12]

To a solution of S9 (40.0 mg, 0.248 mmol) in 1,4-dioxane (2.5 mL) was added SeO2 (55.1 mg, 0.496 mmol). The mixture was stirred at 60° C. overnight then cooled to 22° C. The mixture was concentrated in vacuo and the crude residue was purified by flash column chromatography (gradient, 5-25% EtOAc:hexanes). The isoquinoline S10 was obtained as a white solid (27.3 mg, 63%). $^{1}$H NMR (500 MHz, DMSO-d6) ö 10.32 (s, 1H), 9.37-9.41 (m, 1H), 8.59 (d, J=1.5 Hz, 1H), 8.16-8.20 (m, 1H), 7.82-7.87 (m, 2H). $^{13}$C NMR (125 MHz, DMSO-d6) ö 194.23, 157.16 (d, $^{1}$JC-F=270.3 Hz), 146.44 (d, $^{3}$JC-F=5.6 Hz), 131.07 (d, $^{4}$JC-F=2.2 Hz), 130.95 128.48 (d, $^{2}$JC-F=24.6 Hz), 128.14 (d, $^{4}$JC-F=4.1 Hz), 126.85 (d, $^{2}$JC-F=14.4 Hz), 125.64 (d, $^{4}$JC-F=1.8 Hz), 119.85 (d, $^{3}$JC-F=4.7 Hz). 19F NMR (376 MHz, CDCl3) ö −129.02. DART-MS: m/z calcd. for C10H6FNO $(M+H)^{+}$ 176.05062. found 176.05012.

(E)-2-((4-Fluoroisoquinolin-1-yl)methylene)hydrazine-1-carbothioamide (HCT2)

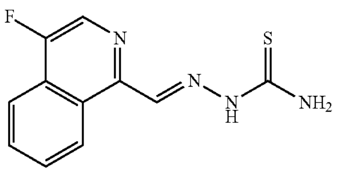 [SMILES: NC(=S)N/N=C/c1ncc(F)c2ccccc12]

To a solution of S10 (6.0 mg, 0.0343 mmol) in EtOH (0.5 mL) was added thiosemicarbazide (3.3 mg, 0.0343 mmol) and HCl (34 μL, 0.206 mmol, 6 M in H2O). The mixture was stirred and refluxed for 1.5 h then cooled to 22° C. The hydrochloride salt that formed was then neutralized with saturated aqueous $NaHCO_3$ solution (0.5 mL). The precipitate of the desired compound was collected by filtration, washed with water, EtOH and then dried to yield the isoquinoline HCT2 as a pale-yellow solid (3.0 mg, 35%). $^{1}$H NMR (500 MHz, DMSO-d6) ö 11.70 (s, 1H), 9.28 (d, J=8.5 Hz, 1H), 8.56 (d, J=1.5 Hz, 1H), 8.53 (s, 1H), 8.48 (s, 1H), 8.13 (d, J=8.2 Hz, 1H), 7.94 (ddd, J=8.2, 7.0, 0.9 Hz, 1H), 7.85 (m, 2H). $^{13}$C NMR (125 MHz, DMSO-d6) ö 178.84, 154.73 (d, $^{1}$JC-F=262.2 Hz), 148.03 (d, $^{3}$JC-F=5.2 Hz), 145.84, 131.75, 130.69, 128.10 (d, $^{2}$JC-F=23.3 Hz), 127.75, 127.35 (d, $^{4}$JC-F=3.0 Hz), 126.51 (d, $^{2}$JC-F=14.9 Hz), 119.79 (d, $^{3}$JC-F=4.6 Hz). 19F NMR (376 MHz, DMSO-d6) ö −137.31. DART-MS: m/z calcd. for C11H9FN4S $(M+H)^{+}$ 249.06047. found 249.05042.

(E)-2-((4-Fluoroisoquinolin-1-yl)methylene)-N-methylhydrazine-1-carbothioamide (HCT7)

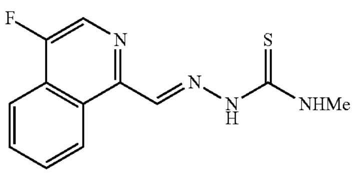 [SMILES: CNC(=S)N/N=C/c1ncc(F)c2ccccc12]

To a solution of S10 (6.0 mg, 0.0343 mmol) in EtOH (0.5 mL) was added 4-methyl-3-thiosemicarbazide (3.6 mg, 0.0343 mmol) and HCl (34 μL, 0.206 mmol, 6 M in H2O). The mixture was stirred and refluxed for 1.5 h then cooled to 22° C. The hydrochloride salt that formed was then neutralized with saturated aqueous $NaHCO_3$ solution (0.5 mL). The precipitate of the desired compound was collected by filtration, washed with water, EtOH and then dried to yield the isoquinoline HCT7 as a pale-yellow solid (2.6 mg, 29%). $^{1H}$ NMR (500 MHz, DMSO-d6) ö 11.76 (s, 1H), 9.19 (d, J=8.6 Hz, 1H), 8.56 (d, J=1.4 Hz, 1H), 8.56 (s, 1H), 8.34 (d, J=4.4 Hz, 1H), 8.14 (d, J=8.3 Hz, 1H), 7.94-7.97 (m, 1H), 7.85-7.89 (m, 1H), 3.06 (d, J=4.6 Hz, 3H). $^{13}$C NMR (125 MHz, DMSO-d6) ö 178.84, 154.73 (d, $^{1}$JC-F=262.2 Hz), 148.03 (d, $^{3}$JC-F=5.2 Hz), 145.84, 131.75, 130.69, 128.10 (d, $^{2}$JC-F=23.3 Hz), 127.75, 127.35 (d, $^{4}$JC-F=3.0 Hz), 126.51 (d, $^{2}$JC-F=14.9 Hz), 119.79 (d, $^{3}$JC-F=4.6 Hz), 31.86. $^{19}$F NMR (376 MHz, DMSO-d6) ö −137.53, extraneous peak found at −134.32. DART-MS: m/z calcd. for C12H12FN4S $(M+H)^{+}$ 263.07612. found 263.07520.

(E)-2-((4-Fluoroisoquinolin-1-yl)methylene)-N,N-dimethylhydrazine-1-carbothioamide and (Z)-2-((4-Fluoroisoquinolin-1-yl)methylene)-N,N-dimethylhydrazine-1-carbothioamide (HCT12)

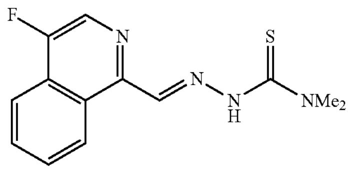

and

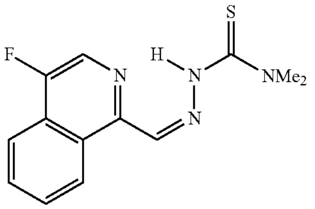

To a solution of S10 (17.8 mg, 0.102 mmol) in MeOH (1.0 mL) was added 4,4-dimethyl-3-thiosemicarbazide (12.0 mg, 0.102 mmol) and HCl (101 μL, 0.610 mmol, 6 M in H2O). The mixture was microwaved at 300 W and 50° C. for 1.0 h. The hydrochloride salt that formed was then neutralized with saturated aqueous $NaHCO_3$ solution (1.0 mL). The precipitate of the desired compound was collected by filtration, washed with water, EtOH and then dried to yield the isoquinoline HCT12 as a pale-yellow solid (16.0 mg, 57%) (mixture of E and Z isomers). $^{1}$H NMR (500 MHz, DMSO-d6) ö 15.52 (s, 0.15H), 11.28 (s, 1H), 9.87 (d, J=8.7 Hz, 1H), 8.87 (d, J=9.0 Hz, 0.15H), 8.77 (d, J=1.9 Hz, 0.15H), 8.69 (s, 1H), 8.57 (d, J=1.6 Hz, 1.15H), 8.23 (d, J=8.2 Hz, 0.15H), 8.15 (d, J=8.2 Hz, 1H), 8.02-8.05 (m, 0.15H), 7.92-7.97 (m, 1.15H), 7.86 (ddd, J=8.3, 6.9, 1.3 Hz, 1H), 3.42 (s, 0.90H), 3.36 (s, 6H). $^{13}$C NMR (125 MHz, DMSO-d6) ö 180.79, 180.73, 154.60 (d, $^{1}$JC-F=261.7 Hz), 154.13 (d, $^{1}$JC-F=261.8 Hz), 148.75 (d, $^{3}$JC-F=5.1 Hz), 147.76 (d, $^{3}$JC-F=5.7 Hz), 147.05, 132.52, 131.59 (d, $^{4}$JC-F=5.1 Hz), 131.10, 130.49, 130.30, 128.60 (d, $^{4}$JC-F=3.3 Hz), 128.41 (d, $^{4}$JC-F=1.0 Hz), 127.90 (d, $^{2}$JC-F=23.3 Hz), 127.19 (d, $^{4}$JC-F=2.6 Hz), 126.88 (d, $^{2}$JC-F=14.8 Hz), 126.71 (d, $^{2}$JC-F=14.7 Hz), 126.35 (d, $^{2}$JC-F=25.2 Hz), 124.98, 120.23 (d, $^{3}$JC-F=4.3 Hz), 119.79 (d, $^{3}$JC-F=4.7 Hz), 42.04 (4C). $^{19}$F NMR (376 MHz, DMSO-d6) ö −134.93, −138.02. DART-MS: m/z calcd. for C13H14FN4S $(M+H)^{+}$ 277.09177. found 277.09096.

6-Fluoro-1-methylisoquinoline (S11)

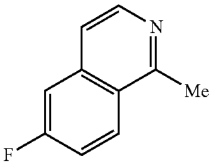 [SMILES: Cc1nccc2cc(F)ccc12]

To a solution of 6-fluoroisoquinoline (1.00 g, 6.80 mmol) in THF (120 mL) was added allyl chloroformate (1.64 mL, 13.59 mmol). MeMgBr (6.98 mL, 13.59 mmol, 2 M in diethyl ether) was then added dropwise to the reaction mixture at 0° C. while stirring and the mixture was gradually warmed to 22° C. over a period of 2 h. The reaction was quenched with saturated aqueous NH4Cl (12 mL) and water (120 mL) was added. The organic layer was separated and the aqueous layer was extracted with EtOAc (3×120 mL). The organic layers were combined and dried over MgSO4, filtered, and then concentrated in vacuo. The crude residue in EtOAc was filtered through a silica plug, concentrated in vacuo and the crude residue was subjected to the next reaction without further purification. To a solution of the crude residue and Pd(PPh3)4 (293.4 mg, 0.254 mmol) in DCM (50 mL) at 0° C. was added morpholine (437.9 uL, 5.08 mmol). The reaction was stirred and slowly warmed to 22° C. over a period of 3 h. The mixture was cooled to 0° C. and DDQ (1.15 g, 5.08 mmol) was added portionwise. After the reaction mixture stirred at 0° C. for 30 min, the reaction was slowly poured into a solution of saturated $NaHCO_3$solution (50 mL) and extracted with DCM (3×50). The combined extracts are washed with brine, dried over Na2SO4, and concentrated in vacuo and the crude residue was purified by flash column chromatography (gradient, 5-25% EtOAc:hexanes). The isoquinoline S11 was obtained as a brown oil (583.9 mg, 53% over three steps). $^1$H NMR (500 MHz, DMSO-d6) ö 8.37 (d, J=5.8 Hz, 1H), 8.13 (dd, J=9.2, 5.5 Hz, 1H), 7.46 (d, J=5.8 Hz, 1H), 7.40 (dd, J=9.3, 2.6 Hz, 1H), 7.34 (td, J=8.8, 2.6 Hz, 1H), 2.95 (s, 3H). $^{13}$C NMR (125 MHz, DMSO-d6) ö 162.94 (d, $^1$JC-F=252.2 Hz), 158.53 (d, $^5$JC-F=1.0 Hz), 142.77, 137.58 (d, $^3$JC-F=10.4 Hz), 128.79 (d, $^3$JC-F=9.6 Hz), 124.72 (d, $^4$JC-F=1.0 Hz), 119.01 (d, $^4$JC-F=5.0 Hz), 117.31 (d, $^2$JC-F=25.0 Hz), 110.44 (d, $^2$JC-F=20.6 Hz), 22.53. $^{19}$F NMR (376 MHz, CDCl3) ö −108.23. DART-MS: m/z calcd. for C10H9FN $(M+H)^+$ 162.07135. found 162.07096.

6-Fluoroisoquinoline-1-carboxaldehyde (S12)

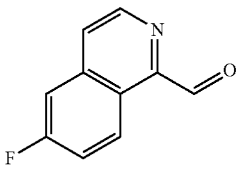 [SMILES: O=Cc1nccc2cc(F)ccc12]

To a solution of S11 (500.0 mg, 3.10 mmol) in 1,4-dioxane (19.0 mL) was added SeO2 (688.4 mg, 6.20 mmol). The mixture was stirred at 60° C. overnight then cooled to 22° C. The mixture was concentrated in vacuo and the crude residue was purified by flash column chromatography (gradient, 5-25% EtOAc:hexanes). The isoquinoline S12 was obtained as a white solid (200.9 mg, 37%). $^1$H NMR (500 MHz, DMSO-d6) ö 10.35 (s, 1H), 9.39 (ddd, J=10.1, 5.6, 0.9 Hz, 1H), 8.75 (dd, J=5.6, 0.4 Hz, 1H), 7.85 (d, J=5.5 Hz, 1H), 7.50-7.54 (m, 2H). $^{13}$C NMR (125 MHz, DMSO-d6) ö 195.51, 163.18 (d, $^1$JC-F=255.1 Hz), 149.71 (d, $^4$JC-F=1.8 Hz), 143.34 (d, $^5$JC-F=1.0 Hz), 138.70 (d, $^3$JC-F=10.4 Hz), 129.24 (d, $^3$JC-F=9.2 Hz), 124.90 (d, $^4$JC-F=5.4 Hz), 123.49 (d, $^5$JC-F=1.0 Hz), 120.53 (d, $^2$JC-F=24.8 Hz), 110.23 (d, $^2$JC-F=20.9 Hz). $^{19}$F NMR (376 MHz, CDCl3) ö −105.46. DART-MS: m/z calcd. for C10H7FNO $(M+H)^+$ 176.05062. found 176.05015.

(E)-2-((6-Fluoroisoquinolin-1-yl)methylene)hydrazine-1-carbothioamide (HCT3)

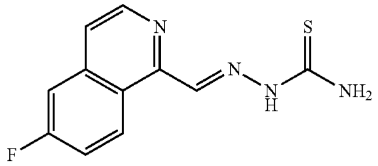 [SMILES: NC(=S)N/N=C/c1nccc2cc(F)ccc12]

To a solution of S12 (10.2 mg, 0.0582 mmol) in EtOH (0.5 mL) was added thiosemicarbazide (5.3 mg, 0.0582 mmol) and HCl (58 μL, 0.349 mmol, 6 M in H2O). The mixture was stirred and refluxed for 1.5 h then cooled to 22° C. The hydrochloride salt that formed was then neutralized with saturated aqueous $NaHCO_3$ solution (0.5 mL). The precipitate of the desired compound was collected by filtration, washed with water, EtOH and then dried to yield the isoquinoline HCT3 as a pale-yellow solid (13.4 mg, 93%). $^1$H NMR (500 MHz, DMSO-d6) ö 11.74 (s, 1H), 9.30 (dd, J=9.4, 5.8 Hz, 1H), 8.55 (d, J=5.6 Hz, 1H), 8.51 (s, 2H), 7.80-7.85 (m, 3H), 7.57 (td, J=9.0, 2.8 Hz, 1H). $^{13}$C NMR (125 MHz, DMSO-d6) ö 178.88, 162.70 (d, $^1$JC-F=250.4 Hz), 151.35, 146.33, 143.50, 138.62 (d, $^3$JC-F=10.7 Hz), 131.52 (d, $^3$JC-F=9.5 Hz), 123.24, 121.79 (d, $^4$JC-F=5.0 Hz), 119.36 (d, $^2$JC-F=24.5 Hz), 110.86 (d, $^2$JC-F=20.7 Hz). $^{19}$F NMR (376 MHz, DMSO-d6) ö −107.79, extraneous peak found at −106.49. DART-MS: m/z calcd. for C11H10FN4S $(M+H)^+$ 249.06047. found 249.05984.

(E)-2-((6-Fluoroisoquinolin-1-yl)methylene)-N-methylhydrazine-1-carbothioamide (HCT8)

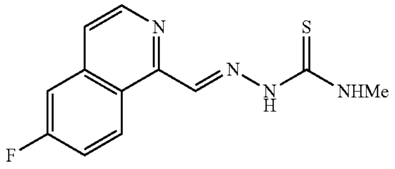 [SMILES: CNC(=S)N/N=C/c1nccc2cc(F)ccc12]

To a solution of S12 (8.8 mg, 0.0502 mmol) in EtOH (0.5 mL) was added 4-methyl-3-thiosemicarbazide (5.3 mg, 0.0502 mmol) and HCl (50 μL, 0.300 mmol, 6 M in H2O). The mixture was stirred and refluxed for 1.5 h then cooled to 22° C. The hydrochloride salt that formed was then neutralized with saturated aqueous $NaHCO_3$ solution (0.5 mL). The precipitate of the desired compound was collected by filtration, washed with water, EtOH and then dried to yield the isoquinoline HCT8 as a pale-yellow solid (10.8 mg, 82%). $^{1H}$ NMR (500 MHz, DMSO-d6) ö 11.80 (s, 1H), 9.20 (dd, J=9.4, 5.7 Hz, 1H), 8.55 (d, J=5.6 Hz, 1H), 8.54 (s, 1H), 8.35 (d, J=4.7 Hz, 1H), 7.83 (dd, J=9.2, 3.9 Hz, 2H) 7.60 (td, J=9.0, 2.7 Hz, 1H), 3.06 (d, J=4.5 Hz, 3H). $^{13}$C NMR (125 MHz, DMSO-d6) ö 178.56, 162.71 (d, $^{1}$JC-F=250.4 Hz), 151.55, 145.22, 143.53, 138.62 (d, $^{3}$JC-F=10.6 Hz), 131.28 (d, $^{3}$JC-F=9.5 Hz), 123.29, 121.67 (d, $^{4}$JC-F=5.1 Hz), 119.23 (d, $^{2}$JC-F=24.8 Hz), 110.89 (d, $^{2}$JC-F=20.8 Hz), 31.85. $^{19}$F NMR (376 MHz, DMSO-d6) ö −106.55, extraneous peak found at −107.74. DART-MS: m/z calcd. for C12H12FN4S $(M+H)^+$ 263.07612. found 263.07538.

(E)-2-((6-Fluoroisoquinolin-1-yl)methylene)-N,N-dimethylhydrazine-1-carbothioamide and (Z)-2-((6-Fluoroisoquinolin-1-yl)methylene)-N,N-dimethylhydrazine-1-carbothioamide (HCT13)

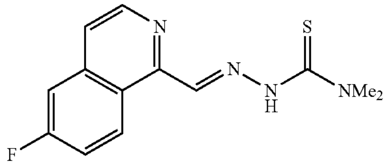

and

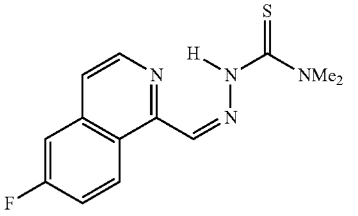

To a solution of S12 (8.6 mg, 0.0491 mmol) in EtOH (0.5 mL) was added 4,4-dimethyl-3-thiosemicarbazide (5.9 mg, 0.0491 mmol) and HCl (49 μL, 0.294 mmol, 6 M in H2O). The mixture was stirred and refluxed for 1.5 h then cooled to 22° C. The hydrochloride salt that formed was then neutralized with saturated aqueous $NaHCO_3$ solution (0.5 mL). the precipitate of the desired compound was collected by filtration, washed with water, EtOH and then dried to yield the isoquinoline HCT13 as a pale-yellow solid (7.4 mg, 55%). $^{1H}$ NMR (500 MHz, DMSO-d6) ö 15.90 (s, 0.21H), 11.30 (s, 1H), 9.87 (dd, J=9.5, 5.9 Hz, 1H), 8.91 (dd, J=9.4, 5.4 Hz, 0.21H), 8.66 (m, 1.21H), 8.59 (s, 0.21H), 8.55 (d, J=5.6 Hz, 1H), 7.97 (d, J=5.6 Hz, 0.21H), 7.91 (dd, J=9.6, 2.7 Hz, 0.21H), 7.79-7.82 (m, 2H), 7.73 (td, J=9.1, 2.7 Hz, 0.21H), 7.62 (ddd, J=9.6, 8.6, 2.8 Hz, 1H), 3.40 (s, 1.26H), 3.33 (s, 6H). $^{13}$C NMR (125 MHz, DMSO-d6) ö 180.78 (2C), 163.19 (d, $^{1}$JC-F=251.7 Hz), 162.66 (d, $^{1}$JC-F=250.6 Hz), 151.99 (d, $^{5}$JC-F=1.2 Hz), 150.63 (d, $^{5}$JC-F=0.9 Hz), 147.57, 143.42, 141.42, 138.83 (d, $^{3}$JC-F=15.5 Hz), 138.76 (d, $^{4}$JC-F=10.7 Hz), 132.08 (d, $^{3}$JC-F=9.3 Hz), 131.62, 128.64 (d, $^{3}$JC-F=9.9 Hz), 124.14, 123.10, 122.12 (d, $^{4}$JC-F=5.2 Hz), 121.56 (d, $^{4}$JC-F=5.1 Hz), 119.54 (d, $^{2}$JC-F=25.6 Hz), 119.14 (d, $^{2}$JC-F=24.4 Hz), 111.48 (d, $^{2}$JC-F=20.8 Hz), 110.90 (d, $^{2}$JC-F=20.7 Hz), 42.04 (4C). $^{19}$F NMR (376 MHz, DMSO-d6) ö −106.34, −107.95. DART-MS: m/z calcd. for C13H14FN4S $(M+H)^+$ 277.09177. found 277.09098.

4-Fluoro-1-methyl-5-nitroisoquinoline (S13)

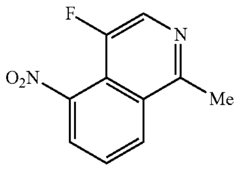 [SMILES: Cc1ncc(F)c2c([N+](=O)[O-])cccc12]

To a solution of S11 (0.376 g 2.333 mmol) in sulfuric acid (0.4 mL) at 0° C. was added KNO3 (0.234 g, 2.333 mmol) in sulfuric acid (0.6 mL). The mixture was heated at 60° C. for 2 h and then poured slowly over crushed ice. The solution was made alkaline with NH4OH; the resulting tan precipitate was filtered, washed with water, and dried to afford S13 as a tan solid (0.210 g, 44%). $^{1}$H NMR (500 MHz, CDCl3) ö 8.42 (d, J=2.9 Hz, 1H), 8.36 (d, J=8.3 Hz, 1H), 7.98 (d, J=7.4 Hz, 1H), 7.77 (t, J=7.8 Hz, 1H), 3.03 (s, 3H). $^{13}$C NMR (125 MHz, CDCl3) ö 155.10 (d, $^{4}$JC-F=5.2 Hz), 151.08 (d, $^{1}$JC-F=262.1 Hz), 144.92, 130.04 (d, $^{2}$JC-F=25.2 Hz), 129.62, 128.88, 127.24, 125.53, 118.43 (d, $^{3}$JC-F=12.1 Hz), 22.66. $^{19}$F NMR (376 MHz, CDCl3) ö −133.19. DART-MS: m/z calcd. for C10H8FN2O2 $(M+H)^+$ 207.05643. found 207.05705.

4-Fluoro-1-methylisoquinolin-5-amine (S14)

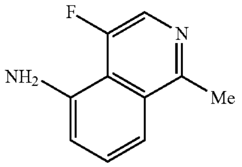 [SMILES: Cc1ncc(F)c2c(N)cccc12]

To a solution of S13 (0.210 g 1.02 mmol) in MeOH (50 mL) iron powder (0.171 g, 3.06 mmol and HCl (1 mL, 12 M in H2O). The mixture was refluxed for 2 h and then a solution of sodium hydroxide (2 mL, 6 M in H2O) was added. The mixture was filtered and extracted with diethyl ether (200 mL). The organic layer was dried over Na2SO4, filtered, and then concentrated in vacuo. The crude residue was purified by flash column chromatography (gradient, 10-30% EtOAc:hexanes). The isoquinoline S14 was obtained as a brown solid (0.173 g, 96%). $^{1}$H NMR (500 MHz, CDCl3) ö 8.09 (d, J=5.1 Hz, 1H), 7.46-7.39 (m, 2H), 6.88 (dd, J=6.9, 1.8 Hz, 1H), 4.83 (br s, 2H), 2.87 (d, J=1.3, 3H). $^{13}$C NMR (125 MHz, CDCl3) ö 155.92 (d, $^{1}$JC-F=253.3 Hz), 154.74 (d, $^{4}$JC-F=4.9 Hz), 142.23 (d, $^{4}$JC-F=3.0 Hz), 129.19, 115.79 (d, $^{3}$JC-F=8.8 Hz), 114.77, 114.76, 113.81 (2C), 22.61. $^{19}$F NMR (376 MHz, CDCl3) ö −136.45. DART-MS: m/z calcd. for C10H10FN2 $(M+H)^+$ 177.08225. found 177.08220.

tert-butyl (4-fluoro-1-methylisoquinolin-5-yl)carbamate (S15)

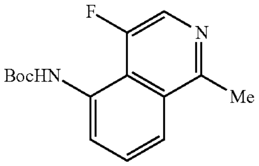 [SMILES: Cc1ncc(F)c2c(NC(=O)OC(C)(C)C)cccc12]

To a solution of S14 (1.14 g, 6.49 mmol) in THF (15 mL) was added DMAP (79.3 mg, 0.65 mmol) then Boc2O (3.54 g, 16.23 mmol) and the mixture was stirred at 22° C. overnight. After completion of the reaction as judged by TLC, K2CO3 (2.69 g, 19.47 mmol) and MeOH (10 mL) were added to the reaction mixture and then refluxed overnight. The mixture was then concentrated in vacuo and resuspended in EtOAc (20 mL) and water (20 mL). The organic layer was separated and the aqueous layer was extracted with EtOAc (3×20 mL). The organic layers were combined and dried over Na2SO4, filtered, and then concentrated in vacuo. The crude residue was purified by flash column chromatography (gradient, 5-20/6 EtOAc:hexanes). The isoquinoline S15 was obtained as a brown oil (0.572 g, 33%). $^{1}$H NMR (500 MHz, CDCl3) ö 8.50 (dd, J=7.9, 1.0 Hz, 1H), 8.17 (d, J=5.7 Hz, 1H), 8.05 (d, J=17.8 Hz, 1H), 7.73 (ddd, J=8.4, 3.0, 1.0 Hz, 1H), 7.60 (t, J=8.2 Hz, 1H), 2.88 (d, J=1.3 Hz, 3H), 1.55 (s, 9H). $^{13}$C NMR (125 MHz, CDCl3) ö 158.37 (d, $^{1}$JC-F=296.5 Hz), 153.19, 137.68, 131.10, 128.23 (d, $^{3}$JC-F=10.7 Hz), 124.83, 124.45, 121.14 (d, $^{2}$JC-F=22.3 Hz), 119.58, 82.72, 28.15 (3C), 17.84, one low-field carbon were either not observed or is overlapping with another low-field carbon. $^{19}$F NMR (376 MHz, CDCl3) ö −136.85. DART-MS: m/z calcd. for C15H18FN2O2 $(M+H)^+$ 277.13468. found 277.13425.

tert-Butyl methyl(4-fluoro-1-methylisoquinolin-5-yl)carbamate (S16)

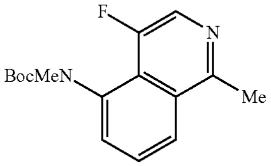

To a solution of S15 (0.524 g, 1.90 mmol) in THF (10 mL) was added NaH 60% in mineral oil (59.2 mg, 2.49 mmol). After effervescence ceased, the resulting solution was refluxed for 30 min. To the reaction mixture was then added MeI (0.350 g, 4.49 mmol) in THF (2 mL) and the solution refluxed overnight. The mixture was concentrated and passed through a silica plug (1:10-2:1 EtOAc:hexanes). The mixture was concentrated in vacuo and the crude residue was purified by flash column chromatography (gradient, 10-30% EtOAc:hexanes). The isoquinoline S16 was obtained as an amber oil containing a mixture of rotamers (0.456 g, 82%). $^{1}$H NMR (400 MHz, CDCl3) ö 8.25-8.22 (m, 1.5H), 8.11-8.02 (m, 1.5H), 7.71-7.61 (m, 2H), 7.55 (dd, J=7.3, 1.3 Hz, 1H), 3.28 (s, 3H), 3.27 (s, 1.5H), 2.96 (s, 3H), 2.95 (s, 1.5H), 1.53 (s, 4.5H), 1.21 (s, 9H). $^{13}$C NMR (125 MHz, CDCl3) ö 155.41, 154.92 (d, $^{4}$JC-F=5.7 Hz), 154.90 (d, $^{4}$JC-F=5.4 Hz), 154.63, 154.51, 153.54 (d, $^{1}$JC-F=259.3 Hz), 137.94, 131.60, 130.52, 130.05, 129.74, 128.44, 128.19, 127.82 (d, $^{2}$JC-F=27.6 Hz), 125.49, 125.08, 124.53, 124.34 (d, $^{3}$JC-F=8.1 Hz), 80.79, 80.23, 38.52 (d, $^{5}$JC-F=3.82 Hz), 37.81 (d, $^{5}$JC-F=3.07 Hz), 28.38 (3C), 28.05 (3C), 22.46, 22.26, two low-field carbons were either not observed or is overlapping with another low-field carbon. $^{19}$F NMR (376 MHz, CDCl3) ö −140.37, −141.22. DART-MS: m/z calcd. for C16H20FN2O2 $(M+H)^+$ 291.15033. found 291.14981.

tert-Butyl methyl(4-fluoro-1-formylisoquinolin-5-yl)carbamate (S17)

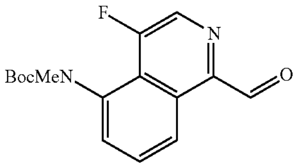

To a solution of S16 (0.40 g, 1.38 mmol) in 1,4-dioxane (10 mL) was added SeO2 (0.183 g, 1.65 mmol). The mixture was stirred at 60° C. overnight then cooled to 22° C. The mixture was concentrated in vacuo and the crude residue was purified by flash column chromatography (gradient, 5-25% EtOAc:hexanes). The isoquinoline S17 was obtained as an off-white solid containing a mixture of rotamers (0.152 g, 36%). $^{1}$H NMR (500 MHz, CDCl3) ö 10.32 (d, J=1.5 Hz, 1H), 10.29 (d, J=1.6 Hz, 0.5H), 9.38 (tdd, J=7.5, 2.7, 1.4 Hz, 1.5H), 8.58 (dd, J=3.9, 1.1 Hz, 1H), 8.56 (dd, J=4.0, 1.3 Hz, 0.5H), 7.80 (tt, J=7.3, 1.4 Hz, 1.5H), 7.68 (dt, J=7.5, 0.5 Hz, 0.5H), 7.62 (dt, J=7.4, 1.0 Hz, 1H), 3.31 (d, J=1.1 Hz, 3H), 3.30 (d, J=0.9 Hz, 1.5H), 1.54 (s, 4.5H), 1.21 (s, 9H). $^{13}$C NMR (125 MHz, CDCl3) 194.12, 194.09, 156.39 (d, $^{1}$JC-F=272.5 Hz), 156.35 (d, $^{1}$JC-F=255.9 Hz), 155.21, 154.41, 146.67 (d, $^{3}$JC-F=6.1 Hz), 137.64 (d, $^{4}$JC-F=1.7 Hz), 131.73 (d, $^{4}$JC-F=1.9 Hz), 131.12 (d, $^{4}$JC-F=1.9 Hz), 131.05, 130.95 (d, $^{2}$JC-F=21.5 Hz), 130.85, 130.57 (d, $^{2}$JC-F=28.5 Hz), 130.25 (d, $^{2}$JC-F=28.2 Hz), 129.83 (d, $^{4}$JC-F=2.4 Hz), 129.49 (d, $^{4}$JC-F=2.5 Hz), 125.05, 124.68 (d, $^{4}$JC-F=1.7 Hz), 124.56 ($^{3}$JC-F, J=7.4 Hz), 124.44 (d, $^{3}$JC-F=7.1 Hz), 81.01, 80.49, 38.56 (d, $^{5}$JC-F=3.3 Hz), 37.83 (d, $^{5}$JC-F=2.6 Hz), 28.36 (3C), 28.03 (3C), one low-field carbon were either not observed or is overlapping with another low-field carbon. $^{19}$F NMR (376 MHz, CDCl3) ö −133.9. DART-MS: m/z calcd. for C16H18FN2O3 $(M+H)^+$ 305.12960. found 305.12824.

(E)-2-((4-Fluoro-5-(methylamino)isoquinolin-1-yl)methylene)-N,N-dimethylhydrazine-1-carbothioamide and (Z)-2-((4-Fluoro-5-(methylamino)isoquinolin-1-yl)methylene)-N,N-dimethylhydrazine-1-carbothioamide (HCT15)

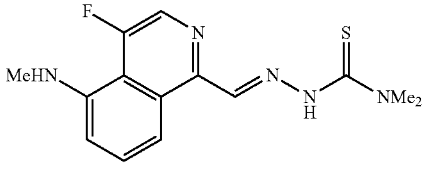

and

-continued

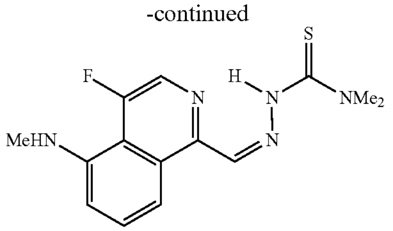

To a solution of S17 (30.0 mg, 0.099 mmol) in MeOH (3.0 mL) was added 4,4-dimethyl-3-thiosemicarbazide (11.7 mg, 0.985 mmol) and HCl (98 μL, 0.59 mmol, 6 M in H2O). The mixture was microwaved at 300 W and 50° C. for 1.0 h. The hydrochloride salt that formed was then neutralized with saturated aqueous $NaHCO_3$ solution (1.5 mL). The precipitate of the desired compound was collected by filtration, washed with water, EtOH and then dried to yield the isoquinoline HCT15 as a pale-yellow solid containing a mixture of E- and Z-isomers (12.2 mg, 41%). $^{1H}$ NMR (500 MHz, DMSO-do) 615.46 (s, 0.33H), 11.13 (br s, 1H), 8.91 (dd, J=8.4, 2.9 Hz, 1H), 8.62 (s, 1H), 8.50 (d, J=5.1 Hz, 0.33H), 8.39 (s, 0.33H), 8.32 (d, J=4.8 Hz, 1H), 7.89 (dd, J=8.5, 2.9 Hz, 0.33H), 7.65 (t, J=8.2 Hz, 0.33H), 7.57 (t, J=8.2 Hz, 1H), 6.82 (d, J=8.0 Hz, 0.33H), 6.73 (d, J=7.9 Hz, 1H), 6.55 (dd, J=11.9, 5.2 Hz, 0.33H), 6.39 (dd, J=12.4, 5.0 Hz, 1H), 3.37 (s, 1.98H), 3.31 (s, 6H), 2.86-2.84 (m, 3.99H). $^{13}$C NMR (125 MHz, DMSO-d6) ö 180.95, 180.72, 156.41 (d, J=260.4 Hz), 147.99 (d, $^{4}$JC-F=4.3 Hz), 147.41, 147.16, 144.92, 144.61 (d, $^{4}$JC-F=3.7 Hz), 131.90, 131.69, 130.83, 130.78, 129.29 (d, $^{4}$JC-F=2.4 Hz), 127.41 (d, $^{2}$JC-F=28.8 Hz), 125.43 (d, $^{2}$JC-F=30.5 Hz), 115.98 (d, $^{2}$JC-F=7.6 Hz), 113.89, 113.84, 110.26, 108.50, 107.78, 42.15 (4C), 30.95 (2C), one low-field carbon were either not observed or is overlapping with another low-field carbon. $^{19}$F NMR (376 MHz, DMSO-d6) ö −125.86, −129.02. DART-MS: m/z calcd. for C14H17FN5S $(M+H)^+$ 306.11832. found 306.11716.

6-Fluoro-1-methyl-5-nitroisoquinoline (S18)

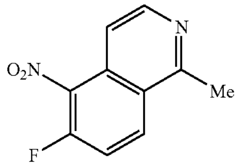 [SMILES: Cc1nccc2c([N+](=O)[O-])c(F)ccc12]

To a solution of S11 (0.584 g, 3.623 mmol) in sulfuric acid (0.8 mL) at 0° C. was added KNO3 (0.366 g, 3.623 mmol) in sulfuric acid (1.2 mL). The mixture was heated at 60° C. for 2 h and then poured slowly over crushed ice. The solution was made alkaline with NH4OH; the resulting tan precipitate was filtered, washed with water, and dried to afford S18 as a tan solid (0.264 g, 35%). $^{1}$H NMR (500 MHz, CDCl3) ö 8.58 (d, J=6.1 Hz, 1H), 8.41 (dd, J=9.4, 4.9 Hz, 1H), 7.70 (d, J=6.0 Hz, 1H), 7.55 (t, J=9.2 Hz, 1H), 3.07 (s, 3H). $^{13}$C NMR (125 MHz, CDCl3) ö 159.08, 155.06 (d, JC-F=266.6 Hz), 144.50, 132.29 (d, $^{3}$JC-F=10.0 Hz), 129.83 (2C), 124.19, 117.40 (d, $^{2}$JC-F=23.5 Hz), 113.60, 22.41. $^{19}$F NMR (376 MHz, CDCl3) ö −113.01. DART-MS: m/z calcd. for C10H8FN2O2 $(M+H)^+$ 207.05643. found 207.05690.

6-Fluoro-1-methylisoquinolin-5-amine (S19)

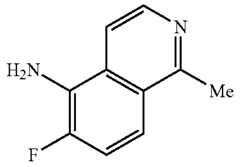

To a solution of S18 (0.264 g, 1.28 mmol) in MeOH (60 mL) iron powder (0.214 g, 3.83 mmol) and HCl (1 mL, 12 M in H2O). The mixture was refluxed for 2 h and then a solution of sodium hydroxide (2 mL, 6 M in H2O) was added. The mixture was filtered and extracted with diethyl ether (200 mL). The organic layer was dried over Na2SO4, filtered, and then concentrated in vacuo. The crude residue was purified by flash column chromatography (gradient, 10-30% EtOAc:hexanes). The isoquinoline S19 was obtained as a brown solid (145.8 mg, 82%). $^{1}$H NMR (500 MHz, CDCl3) ö 8.36 (d, J=6.2 Hz, 1H), 7.62 (dd, J=9.1, 4.8 Hz, 2H), 7.44 (d, J=9.9 Hz, 1H), 4.27 (br s, 2H), 3.06 (s, 3H). $^{13}$C NMR (125 MHz, CDCl3) ö 164.80, 159.77 (d, $^{1}$JC-F=263.7 Hz), 150.34, 139.41 (d, $^{3}$JC-F=10.8 Hz), 137.94, 133.78, 128.91, 122.74 (d, $^{2}$JC-F=22.7 Hz), 118.04 (d, $^{4}$JC-F=5.2 Hz), 27.69. 19F NMR (376 MHz, CDCl3) 0-125.82. DART-MS: m/z calcd. for C10H10FN2 $(M+H)^+$ 177.08225. found 177.08291.

tert-Butyl (6-fluoro-1-methylisoquinolin-5-yl)carbamate (S20)

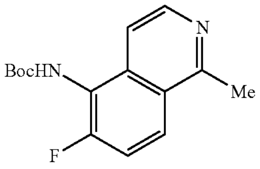 [SMILES: Cc1nccc2c(NC(=O)OC(C)(C)C)c(F)ccc12]

To a solution of S19 (0.715 g, 4.06 mmol) in THF (15 mL) was added DMAP (49.5 mg, 0.41 mmol) then Boc2O (2.21 g, 10.14 mmol) and the mixture was stirred at 22° C. overnight. After completion of the reaction as attested by TLC, K2CO3 (1.68 g, 12.17 mmol) and MeOH (10 mL) were added to the reaction mixture and was refluxed overnight. The mixture was then concentrated in vacuo and resuspended in EtOAc (20 mL) and water (20 mL). The organic layer was separated and the aqueous layer was extracted with EtOAc (3×20 mL). The organic layers were combined and dried over Na2SO4, filtered, and then concentrated in vacuo. The crude residue was purified by flash column chromatography (gradient, 5-20% EtOAc:hexanes). The isoquinoline S20 was obtained as a brown oil (0.303 g, 27%). $^{1}$H NMR (500 MHz, CDCl3) ö 8.40 (d, J=6.0 Hz, 1H), 8.06 (dd, J=9.3, 5.0 Hz, 1H), 7.65 (d, J=6.0 Hz, 1H), 7.39 (t, J=9.3 Hz, 1H), 6.59 (br s, 1H), 2.95 (s, 3H), 1.50 (s, 9H). 13C NMR (125 MHz, CDCl3) ö 160.58 (d, $^{1}$JC-F=260.2 Hz), 157.19, 153.19, 137.68, 131.09 (d, $^{4}$JC-F=4.9 Hz), 128.23 (d, $^{3}$JC-F=10.7 Hz), 124.83, 124.45, 121.14 (d, $^{2}$JC-F=22.1 Hz), 119.60, 82.72, 28.15 (3C), 17.84. $^{19}$F NMR (376 MHz, CDCl3) ö −112.86. DART-MS: m/z calcd. for C15H18FN2O2 $(M+H)^+$ 277.13468, found 277.13425.

tert-Butyl methyl(6-fluoro-1-methylisoquinolin-5-yl)carbamate (S21)

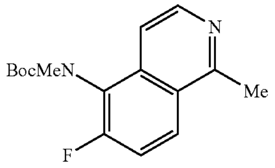

To a solution of S20 (0.150 g, 0.543 mmol) in THF (4 mL) was added NaH 60% in mineral oil (28.0 mg, 0.706 mmol). After effervescence ceased, the resulting solution was refluxed for 30 min. To the reaction mixture was added the MeI (0.10 g, 0.706 mmol) in THF (0.5 mL) and the solution refluxed overnight. The mixture was concentrated and passed through a silica plug (1:10-2:1 EtOAc:hexanes). The mixture was concentrated in vacuo and the crude residue was purified by flash column chromatography (gradient, 10-30% EtOAc:hexanes). The isoquinoline S21 was obtained as a mixture of rotational isomers as an amber oil (0.120 g, 76%). $^{1}$H NMR (500 MHz, CDCl3) ö 8.44 (d, J=5.8 Hz, 1.27H), 8.16-8.02 (m, 1.27H), 7.51 (d, J=6.0 Hz, 1H), 7.49 (d, J=6.3 Hz, 0.27H), 7.39 (t, J=9.3 Hz, 1.27H), 3.26 (s, 0.81H), 3.25 (s, 3H), 2.98 (s, 3H), 2.96 (s, 0.81H), 1.56 (s, 2.43H), 1.26 (s, 9H). $^{13}$C NMR (125 MHz, CDCl3) ö 158.89, 158.88, 158.09 (d, $^{1}$JC-F=254.3 Hz), 154.97, 154.78, 143.18 (2C), 135.55, 135.36 (d, $^{4}$JC-F=3.7 Hz), 127.66 (d, $^{3}$JC-F=9.7 Hz), 127.38 (d, $^{3}$JC-F=9.6 Hz), 125.25, 125.06 (2C), 124.88, 124.78, 117.42 (d, $^{2}$JC-F=24.0 Hz), 117.12 (d, $^{2}$JC-F=24.1 Hz), 114.35 (d, $^{3}$JC-F=5.8 Hz), 81.18, 80.61, 37.43, 36.39, 28.35 (3C), 27.99 (3C), 22.62, 22.56, one low-field carbon were either not observed or is overlapping with another low-field carbon. $^{19}$F NMR (376 MHz, CDCl3) ö −114.54, −115.33. DART-MS: m/z calcd. for C16H20FN2O2 $(M+H)^+$ 291.15033, found 291.15011.

tert-Butyl methyl(6-fluoro-1-formylisoquinolin-5-yl)carbamate (S22)

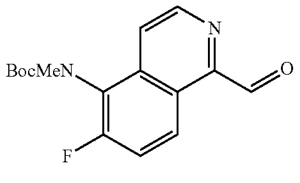

To a solution of S21 (0.1000 g, 0.344 mmol) in 1,4-dioxane (2 mL) was added SeO2 (38.2 mg, 0.344 mmol). The mixture was stirred at 60° C. overnight then cooled to 22° C. The mixture was concentrated in vacuo and the crude residue was purified by flash column chromatography (gradient, 5-25% EtOAc:hexanes). The isoquinoline S22 was obtained as an off-white solid containing a mixture of rotamers (45.3 mg, 43%). $^{1}$H NMR (500 MHz, CDCl3) δ 10.37 (s, 1H), 10.35 (s, 0.3H), 9.35 (dd, J=9.4, 5.1 Hz, 1.3H), 8.82 (d, J=5.8 Hz, 1.3H), 7.92 (d, J=5.7 Hz, 1H), 7.88 (d, J=5.8 Hz, 0.3H), 7.56 (t, J=9.4 Hz, 1.3H), 3.29 (s, 0.9H), 3.28 (s, 3H), 1.57 (s, 2.7H), 1.25 (s, 9H). $^{13}$C NMR (125 MHz, CDCl3) δ 195.40 (2C), 158.41 (d, $^{1}$JC-F=257.6 Hz), 154.77 (2C), 149.92, 143.81, 143.72 (2C), 136.73 (d, $^{4}$JC-F=4.6 Hz), 136.59 (d, $^{4}$JC-F=3.8 Hz), 128.17 (d, $^{3}$JC-F=10.7 Hz), 127.91 (d, $^{3}$JC-F=9.3 Hz), 124.72 (d, $^{3}$JC-F=13.3 Hz), 124.00, 123.80, 120.68 (d, $^{2}$JC-F=24.7 Hz), 120.44 (d, $^{2}$JC-F=24.1 Hz), 120.31, 120.22 (d, $^{3}$JC-F=6.3 Hz), 81.55, 81.00, 37.58, 36.53, 28.32 (3C), 27.97 (3C), two low-field carbon were either not observed or is overlapping with another low-field carbon. 19F NMR (376 MHz, CDCl3) δ −112.18, −112.95. DART-MS: m/z calcd. for C16H18FN2O3 $(M+H)^+$ 305.1296. found 305.12819.

(E)-2-((6-Fluoro-5-(methylamino)isoquinolin-1-yl)methylene)-N,N-dimethylhydrazine-1-carbothioamide and (Z)-2-((6-Fluoro-5-(methylamino)isoquinolin-1-yl)methylene)-N,N-dimethylhydrazine-1-carbothioamide (HCT14)

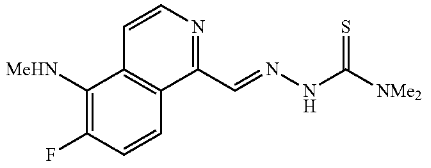

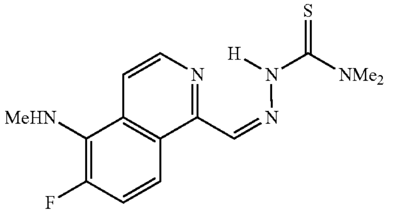

To a solution of S22 (10.0 mg, 0.033 mmol) in EtOH (0.5 mL) was added 4,4-dimethyl-3-thiosemicarbazide (3.9 mg, 0.033 mmol) and HCl (33 μL, 0.197 mmol, 6 M in H2O). The mixture was stirred and refluxed for 1.5 h then cooled to 22° C. The hydrochloride salt that formed was then neutralized with saturated aqueous $NaHCO_3$ solution (0.5 mL). the precipitate of the desired compound was collected by filtration, washed with water, EtOH and then dried to yield the isoquinoline HCT14 as a pale-yellow solid (6.7 mg, 67%). $^{1}$H NMR (500 MHz, DMSO-d6) δ 15.96 (s, 0.17H), 11.22 (Br s, 1H), 9.20 (s, 1H), 8.62-8.54 (m, 1.17H), 8.52 (s, 0.17H), 8.34 (d, J=5.5 Hz, 1H), 8.20 (d, J=6.2 Hz, 0.17H), 8.07 (dd, J=9.3, 4.2 Hz, 0.17H), 7.87 (br s, 1H), 7.56 (dd, J=13.6, 9.2 Hz, 0.17H), 7.33 (dd, J=13.4, 9.5 Hz, 1H), 6.10 (br s, 0.17H), 5.69 (br s, 1H), 3.41 (s, 1.02H), 3.27 (s, 6H), 3.10 (t, J=5.5 Hz, 0.51H), 3.05 (t, J=5.2 Hz, 3H). A $^{13}$C NMR was not obtained. $^{19}$F NMR (376 MHz, CDCl3) δ −129.05, −129.53. DART-MS: m/z calcd. for C14H17FN5S $(M+H)^+$ 305.11832. found 305.11719.C1

Cu(HCT13)Cl, also referred to as Cu(HCT:13) and HCT16:

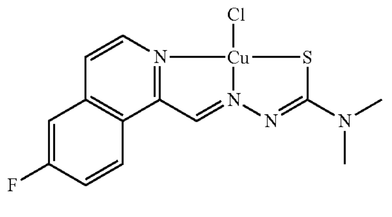

HCT13 (100.0 mg, 0.362 mmol) was dissolved in DMF (8 mL) with gentle heating and stirring. A solution of $CuCl_2$ (48.7 mg, 0.362 mmol) in water (8 mL) was added dropwise with stirring, and the solution immediately turned dark brown and a tan color solid formed upon further addition of the copper(II) chloride solution. The solid was filtered, washed with EtOH three times then dried through suction to obtain a brown solid (94.8 mg, 70%). HR-MS (ESI+) data; m/z calcd for $[C_{13}H_{12}FCuN_4S+MeCN]$=379.0323. found 379.0297. M/z calcd for $[C_{13}H_{12}FCuN_4S]^+$=338.00572. found 338.0038 (Thermo LTQ-Orbitrap XL).

Reference for Example 5: (1) Agrawal, et al., J. Med. Chem. 1968, 11(4), 700-703.

The section headings used herein are for organizational purposes only and are not to be construed as limiting the subject matter described. All documents, or portions of documents, cited in the application are hereby expressly incorporated by reference in their entirety for any purpose.

While various embodiments and aspects are shown and described herein, it will be obvious to those skilled in the art that such embodiments and aspects are provided by way of example only. Numerous variations, changes, and substitutions will now occur to those skilled in the art. Various alternatives to the embodiments and aspects described herein may be used.

What is claimed is:

1. A compound of Formula (Ia), a pharmaceutically acceptable salt thereof, a metal complex thereof, or a pharmaceutically acceptable salt of a metal complex thereof:

(Ia)

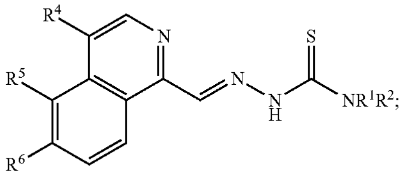

wherein:
$R^1$ is unsubstituted $C_{1-4}$ alkyl;
$R^2$ is hydrogen or unsubstituted $C_{1-4}$ alkyl; and
$R^4$, $R^5$, and $R^6$ are each independently hydrogen, fluorine, chlorine, bromine, iodine, —$NH_2$, $N(C_{1-4}$ alkyl$)(C_{1-4}$ alkyl), wherein when $R_2$ is H, $R_4$-$R_6$ are all not H.

2. The compound of claim 1, wherein
$R^1$ is —$CH_3$ or —$CH_2CH_3$;
$R^2$ is hydrogen, —$CH_3$, or —$CH_2CH_3$; and
$R^4$, $R^5$, and $R^6$ are each independently hydrogen, fluorine, chlorine, bromine, iodine, —$NH_2$, —$NHCH_3$, —$NHCH_2CH_3$, —$N(CH_3)_2$, —$N(CH_3)(CH_2CH_3)$, or —$N(CH_2CH_3)_2$.

3. The compound of claim 1, wherein
$R^1$ is —$CH_3$ or —$CH_2CH_3$;
$R^2$ is hydrogen, —$CH_3$, or —$CH_2CH_3$; and
$R^4$, $R^5$, and $R^6$ are each independently hydrogen, fluorine, $NH_2$, —$NHCH_3$, —$NHCH_2CH_3$, —$N(CH_3)_2$, —$N(CH_3)(CH_2CH_3)$, or —$N(CH_2CH_3)_2$.

4. The compound of claim 1, wherein
$R^1$ is —$CH_3$ or $CH_2CH_3$;
$R^2$ is —$CH_3$ or $CH_2CH_3$;
$R^4$ and $R^6$ are each independently hydrogen, fluorine, chlorine, bromine, or iodine; and
$R^5$ is hydrogen, $NH_2$, —$NHCH_3$, —$NHCH_2CH_3$, —$N(CH_3)_2$, —$N(CH_3)(CH_2CH_3)$, or —$N(CH_2CH_3)_2$.

5. The compound of claim 1, wherein
$R^1$ is —$CH_3$ or $CH_2CH_3$;
$R^2$ is —$CH_3$ or $CH_2CH_3$;
$R^4$ and $R^6$ are each independently hydrogen or fluorine; and
$R^5$ is hydrogen, $NH_2$, —$NHCH_3$, or —$NHCH_2CH_3$.

6. The compound of claim 1 having the structure:

(HCT13)

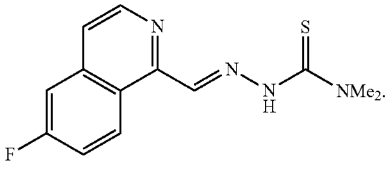

7. The compound of claim 1 having the structure:

(HCT12)

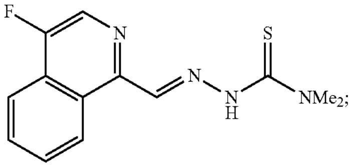

(HCT14)

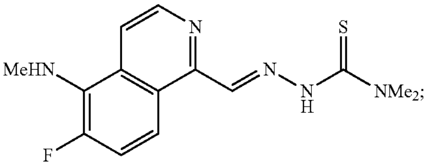

or (HCT15)

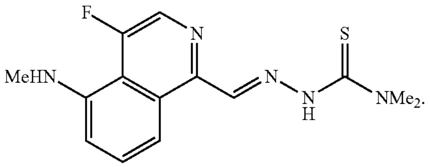

8. The compound of claim 1 having the structure:

(HCT7)

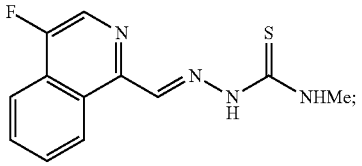

(HCT8)

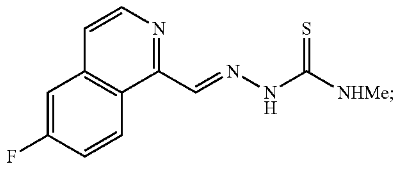

-continued (HCT9)

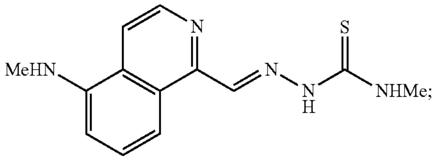

or (HCT10)

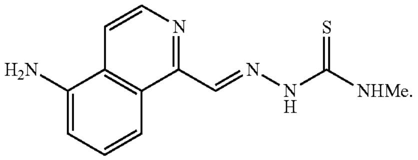

9. A pharmaceutical composition comprising the compound of claim 1 and a pharmaceutically acceptable excipient.

10. A composition comprising: (i) the compound of claim 1, and (ii) copper, a copper salt, zinc, a zinc salt, cobalt, a cobalt salt, nickel, a nickel salt, magnesium, a magnesium salt, iron, an iron salt, manganese, a manganese salt, gallium, a gallium salt, germanium, a germanium salt, calcium, a calcium salt, or a combination of two or more thereof.

11. A method of treating cancer in a subject in need thereof, the method comprising administering to the subject a therapeutically effective amount of the compound of claim 1, wherein the cancer is prostate cancer, small cell lung carcinoma, pancreatic ductal adenocarcinoma, or leukemia.

12. A method of treating cancer in a subject in need thereof, the method comprising administering to the subject a therapeutically effective amount of the compound of claim 1.

13. A method of treating cancer in a subject in need thereof, the method comprising administering to the subject a therapeutically effective amount of the composition of claim 1, wherein the cancer is prostate cancer, small cell lung carcinoma, pancreatic ductal adenocarcinoma, or leukemia.

* * * * *